US008389500B2

(12) United States Patent
Abelman et al.

(10) Patent No.: US 8,389,500 B2
(45) Date of Patent: Mar. 5, 2013

(54) FUSED HETEROCYCLIC COMPOUNDS AS ION CHANNEL MODULATORS

(75) Inventors: Matthew Abelman, Mountain View, CA (US); Elfatih Elzein, Fremont, CA (US); Robert Jiang, Milpitas, CA (US); Rao Kalla, Sunnyvale, CA (US); Tetsuya Kobayashi, Sunnyvale, CA (US); Xiaofen Li, Mountain View, CA (US); Thao Perry, San Jose, CA (US); Jeff Zablocki, Los Altos, CA (US)

(73) Assignee: Gilead Sciences, Inc., Foster City, CA (US)

( * ) Notice: Subject to any disclaimer, the term of this patent is extended or adjusted under 35 U.S.C. 154(b) by 343 days.

(21) Appl. No.: 12/607,833

(22) Filed: Oct. 28, 2009

(65) Prior Publication Data

US 2010/0113449 A1    May 6, 2010

Related U.S. Application Data

(60) Provisional application No. 61/109,857, filed on Oct. 30, 2008, provisional application No. 61/152,701, filed on Feb. 14, 2009.

(51) Int. Cl.
| | |
|---|---|
| A61K 31/18 | (2006.01) |
| A61K 31/196 | (2006.01) |
| A61K 31/24 | (2006.01) |
| A61K 31/41 | (2006.01) |
| A61K 31/44 | (2006.01) |
| A61K 31/445 | (2006.01) |
| A61K 31/495 | (2006.01) |
| A61K 31/5375 | (2006.01) |
| A61K 31/662 | (2006.01) |
| A61P 3/10 | (2006.01) |
| A61P 9/00 | (2006.01) |
| A61P 25/02 | (2006.01) |
| A61P 25/08 | (2006.01) |
| C07C 311/08 | (2006.01) |
| C07C 311/14 | (2006.01) |
| C07D 213/42 | (2006.01) |
| C07D 213/82 | (2006.01) |
| C07D 257/04 | (2006.01) |
| C07D 295/13 | (2006.01) |
| C07F 9/40 | (2006.01) |

(52) U.S. Cl. .............. 514/117; 514/238.2; 514/252.12; 514/331; 514/355; 514/357; 514/381; 514/524; 514/530; 514/531; 514/535; 514/536; 514/537; 514/539; 514/562; 514/601; 514/605

(58) Field of Classification Search ........................ None
See application file for complete search history.

(56) References Cited

U.S. PATENT DOCUMENTS 6,849,632 B2 *   2/2005   Zablocki et al. .......... 514/254.02

FOREIGN PATENT DOCUMENTS

| DE | 4238233 A1 | 5/1994 |
| WO | WO 2004/084824 | * 10/2004 |
| WO | WO-2004113279 A1 | 12/2004 |
| WO | WO-2005066166 A2 | 7/2005 |
| WO | WO-2007025575 A1 | 3/2007 |
| WO | WO-2007146824 A2 | 12/2007 |

OTHER PUBLICATIONS

Souillac, Pierre et al., "Characterization of Delivery Systems, Differential Scanning Calorimetry", pp. 217-218 (in Encyclopedia of Controlled Drug Delivery, 1999, John Wiley & Sons, pp. 212-227).*
Vippagunta, Sudha et al., "Crystalline Solids", Advanced Drug Delivery Reviews, 48, 3-26, 2001.*
Scirica, Benjamin M. et al, "Effect of Ranolazine, an Antianginal Agent With Novel Electrophysiological Properties, on the Incidence of Arrhythmias in Patients With Non-ST-Segment-Elevation Acute Coronary Syndrome", Circulation, 116(15), 1647-1652, 2007.*
Christohper, J. et al (2007) "The discovery of 2-amino-e, 5-diarylbenzamide inhibitors of IKK-a and IKK-b kinases" *Bioorganic & Medicinal Chemistry Letters*, 17:3972-3977.
Johnson, M. et al (2005) "Metabotropic glutamate 2 receptor potentiators: receptor modulation, frequency-dependent synaptic activity, and efficacy in preclinical anxiety and pyschosis model(s)" *Psychopharmacology* 179:271-283.
Parrish, C. et al (2007) "Novel ATP-Competitive Kinesin Spindle Protein Inhibitors" *"Journal of Medicinal Chemistry"* 50:4939-4952.
Zaza, A. et al (2008) "Pathophysiology and pharmacology of the cardiac late sodium current" *Pharmacology & Therapeutics* 119:326-339.
International search report and written opinion for PCT US2009/062381, completion date Apr. 21, 2010.

* cited by examiner

*Primary Examiner* — Fiona T Powers
(74) *Attorney, Agent, or Firm* — Francis O. Ginah; J. Ellin Hartrum

(57) ABSTRACT

The present invention relates to compounds that are sodium channel inhibitors and to their use in the treatment of various disease states, including cardiovascular diseases and diabetes. In particular embodiments, the structure of the compounds is given by Formula (IA) or (IB):

Formula (IA)

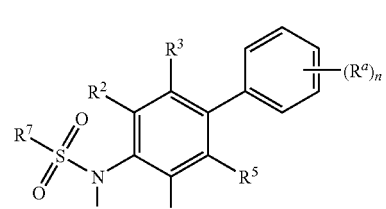

Formula (IB)

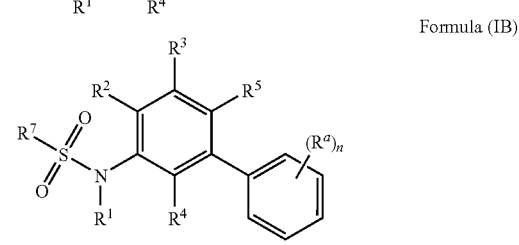

as further described herein. The invention also relates to methods for the preparation of the compounds, and to pharmaceutical compositions containing such compounds.

24 Claims, No Drawings

FUSED HETEROCYCLIC COMPOUNDS AS ION CHANNEL MODULATORS

CROSS-REFERENCE TO RELATED APPLICATIONS

This application claims priority to U.S. Provisional Patent Application Ser. No. 61/152,701, filed Feb. 14, 2009 and U.S. Provisional Patent Application Ser. No. 61/109,857, filed Oct. 30, 2008, the entireties of each of which is incorporated herein by reference.

FIELD OF THE INVENTION

The present invention relates to novel compounds and to their use in the treatment of various disease states, including cardiovascular diseases and diabetes. The invention also relates to methods for their preparation, and to pharmaceutical compositions containing such compounds.

BACKGROUND

The late sodium current (INaL) is a sustained component of the fast Na+ current of cardiac myocytes and neurons. Many common neurological and cardiac conditions are associated with abnormal (INaL) enhancement, which contributes to the pathogenisis of both electrical and contactile dysfunction in mammals. See, for example, Pathophysiology and Pharmacology of the Cardiac "Late Sodium Current", Pharmacology and Therapeutics 119 (2008) 326-339. Accordingly, pharmaceutical compounds that selectively inhibit (INaL) in mammals are useful in treating such disease states.

One example of a selective inhibitor of (INaL) is RANEXA®, a compound approved by the FDA for the treatment of chronic stable angina pectoris. RANEXA® has also been shown to be useful for the treatment of a variety of cardiovascular diseases, including ischemia, reperfusion injury, arrhythmia and unstable angina, and also for the treatment of diabetes. It would be desirable to provide novel compounds that selectively inhibit (INaL) in mammals and that have the same selectivity over peak IN a inhibition as RANEXA®, but with a lower potential for blocking the potassium hERG channel.

SUMMARY OF THE INVENTION

Provided are methods of using compounds of Formula (IA) or (IB):

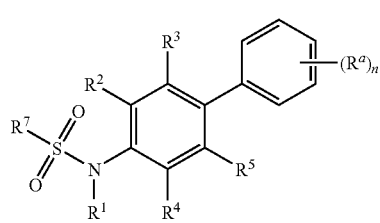

Formula (IA)

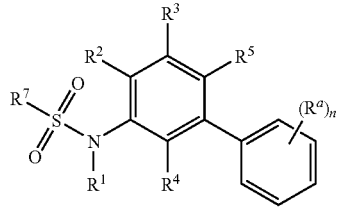

Formula (IB)

wherein:
R$^1$ is hydrogen, C$_{1-4}$ alkyl, —R$^{25}$—O—R$^{20}$, —R$^{25}$—C(O)—O—R$^{20}$, —R$^{25}$—C(O)NHS(O)$_2$R$^{20}$, —R$^{25}$-optionally substituted monocyclic heterocyclyl, —R$^{25}$-optionally substituted monocyclic cycloalkyl —R$^{25}$-optionally substituted monocyclic heteroaryl, —R$^{25}$-optionally substituted monocyclic aryl,
wherein the heterocyclyl, cycloalkyl, aryl, and heteroaryl are optionally substituted with one, two, or three substituents independently selected from halo, hydroxyl, alkyl, —R$^{25}$—C(O)—R$^{20}$, —R$^{25}$—S(O)$_2$—R$^{20}$, lower alkoxy, —CF$_3$, —CN, amino, —NO$_2$, mono- or dialkylamino, and heteroaryl;
R$^2$ and R$^3$ are each independently selected from the group consisting of hydrogen, C$_{1-4}$ alkyl, halo, CN, —CF$_3$, —O—R$^{20}$, —S—R$^{20}$, —C(O)—O—R$^{20}$, —C(O)—N(R$^{20}$)(R$^{22}$), and —P(O)(OR$^{20}$)$_2$;
R$^3$ and R$^4$ are hydrogen;
R$^7$ is C$_{1-4}$ alkyl or cycloalkyl;
R$^a$ are each independently selected from the group consisting of C$_{1-4}$ alkyl, halo, CN, —NO$_2$, CF$_3$, —O—R$^{20}$, —C(O)—O—R$^{20}$, —C(O)—N(R$^{20}$), (R$^{22}$), —N(R$^{20}$)(R$^{22}$)—C(O)—R$^{22}$, —P(O)(OR$^{20}$)$_2$, —R$^{25}$-optionally substituted monocyclic heteroaryl, R$^{25}$-optionally substituted monocyclic aryl;
wherein the aryl and heteroaryl are optionally substituted with one, two, or three substituents independently selected from halo, hydroxyl, alkyl, mono- or dialkylamino, alkyl or aryl or heteroaryl amide, —CN, lower alkoxy, —CF$_3$, aryl, and heteroaryl;
n is 0, 1, 2, or 3;
R$^{20}$ and R$^{22}$ are in each instance independently selected from the group consisting of hydrogen, C$_1$-C$_{15}$ alkyl, C$_2$-C$_{15}$ alkenyl, C$_2$-C$_{15}$ alkynyl, heterocyclyl, aryl, and heteroaryl, wherein the alkyl, alkenyl, alkynyl, heterocyclyl, aryl, and heteroaryl are optionally substituted with one, two, or three substituents independently selected from halo, hydroxyl, alkyl, mono- or dialkylamino, alkyl or aryl or heteroaryl amide, —CN, lower alkoxy, —CF$_3$, aryl, and heteroaryl;
R$^{25}$ is in each instance independently a covalent bond or selected from C$_1$-C$_3$ alkylene optionally substituted with one or two C$_1$-C$_3$ alkyl groups;
or a pharmaceutically acceptable salt, ester, prodrug, or solvate thereof,
in the treatment of a disease or condition in a mammal that is amenable to treatment by a late sodium channel blocker.

The compounds of the invention and their therapeutically acceptable salts, esters, tautomeric forms are potentially of use as medicaments for the treatment of certain diseases, such as, cardiovascular diseases such as atrial and ventricular arrhythmias, heart failure (including congestive heart failure, diastolic heart failure, systolic heart failure, acute heart failure), Prinzmetal's (variant) angina, stable and unstable angina, exercise induced angina, congestive heart disease, ischemia, recurrent ischemia, reperfusion injury, myocardial infarction, acute coronary syndrome, peripheral arterial disease, and intermittent claudication. Such diseases may also include diabetes, and conditions related to diabetes, e.g. diabetic peripheral neuropathy. Such diseases may also include conditions affecting the neuromuscular system resulting in pain, seizures, or paralysis.

Accordingly, in typical embodiments the present invention provides novel compounds that function as late sodium channel blockers. In typical embodiments the invention provides compounds of Formula (IA) or (TB) as described above however with the provisos that when the compounds have the structure of Formula (IA) and $R^7$ is $C_{1-4}$ alkyl and:
1) $R^1$ is $CH_2COOH$, heteroaryl, or halo-substituted benzyl, then not all of $R^2$-$R^5$ can be hydrogen;
2) $R^1$ is $CH(CH_3)COOCH_2CH_3$, then at least one of n or m is not 0;
3) $R^1$ is hydrogen or methyl, then
   a) at least one of $R^a$ and $R^b$ is —$OR^{26}$ where
      $R^{26}$ is heterocyclyl, aryl, or heteroaryl,
      wherein the heterocyclyl, aryl, and heteroaryl are optionally substituted with one, two, or three substituents independently selected from halo, hydroxyl, alkyl, mono- or dialkylamino, alkyl or aryl or heteroaryl amide, —CN, lower alkoxy, —$CF_3$, aryl, and heteroaryl; and
   b) when n is 1 and $R^a$ is unsubstituted phenoxy, then $R^a$ is not attached at the meta position or a pharmaceutically acceptable salt, ester, prodrug, or solvate thereof.

In certain embodiments the invention provides pharmaceutical formulations comprising a therapeutically effective amount of a compound of the invention (e.g. a compound of Formula (IA) or (TB) and at least one pharmaceutically acceptable excipient.

DETAILED DESCRIPTION OF THE INVENTION

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:
1) an alkyl group as defined above, having 1, 2, 3, 4 or 5 substituents, (typically 1, 2, or 3 substituents) selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2 or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or 2) an alkyl group as defined above that is interrupted by 1-10 atoms (e.g. 1, 2, 3, 4, or 5 atoms) independently chosen from oxygen, sulfur and NRa—, where Ra is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, $CF_3$, amino, substituted amino, cyano, or —$S(O)_nR$, in which R is alkyl, aryl, or heteroaryl and n is 0, 1 or 2; or
3) an alkyl group as defined above that has both 1, 2, 3, 4 or 5 substituents as defined above and is also interrupted by 1-10 atoms (e.g. 1, 2, 3, 4, or 5 atoms) as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents (typically 1, 2, or 3 substituents), as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, typically having from 1 to 20 carbon atoms (e.g. 1-10 carbon atoms, or 1, 2, 3, 4, 5 or 6 carbon atoms). This term is exemplified by groups such as methylene (—$CH_2$—), ethylene (—$CH_2CH_2$—), the propylene isomers (e.g., —$CH_2CH_2CH_2$— and —$CH(CH_3)CH_2$—), and the like.

The term "lower alkylene" refers to a diradical of a branched or unbranched saturated hydrocarbon chain, typically having 1, 2, 3, 4, 5, or 6 carbon atoms.

The term "substituted alkylene" refers to:
(1) an alkylene group as defined above having 1, 2, 3, 4, or 5 substituents (typically 1, 2, or 3 substituents) selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or
(2) an alkylene group as defined above that is interrupted by 1-10 groups (e.g. 1, 2, 3, 4, or 5 groups) independently chosen from —O—, —S—, sulfonyl, —C(O)—, —C(O)O—, —C(O)N—, and —NRa—, where Ra is chosen from hydrogen, optionally substituted alkyl, cycloalkyl, cycloalkenyl, aryl, heteroaryl and heterocyclyl; or
(3) an alkylene group as defined above that has both 1, 2, 3, 4 or 5 substituents as defined above and is also interrupted by 1-10 groups as defined above. Examples of substituted alkylenes are chloromethylene (—CH(Cl)—), aminoethylene (—$CH(NH_2)CH_2$—), methylaminoethylene (—$CH(NHMe)CH_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$C$_{1-12}$—N(C$_{1-13}$)—CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Typical alkoxy groups are alkyl-O— and include, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "lower alkoxy" refers to the group R—O— in which R is optionally substituted lower alkyl as defined above. This term is exemplified by groups such as methoxy, ethoxy, n-propoxy, iso-propoxy, n-butoxy, iso-butoxy, t-butoxy, n-hexyloxy, and the like.

The tem, "alkylthio" refers to the group R—S—, where R is as defined for alkoxy.

The term "alkenyl" refers to a monoradical of a branched or unbranched unsaturated hydrocarbon group typically having from 2 to 20 carbon atoms (more typically from 2 to 10 carbon atoms, e.g. 2 to 6 carbon atoms) and having from 1 to 6 carbon-carbon double bonds, e.g. 1, 2, or 3 carbon-carbon double bonds. Typical alkenyl groups include ethenyl (or vinyl, i.e. —CH=CH$_2$), 1-propylene (or allyl, —CH$_2$CH=CH$_2$), isopropylene (—C(CH$_3$)=CH$_2$), bicyclo [2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocylooxy, hydroxyamino, alkoxyamino, nitro, —SO-alkyl, —SO-aryl, —SO-heteroaryl SOS alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The tee in "alkynyl" refers to a monoradical of an unsaturated hydrocarbon, typically having from 2 to 20 carbon atoms (more typically from 2 to 10 carbon atoms, e.g. 2 to 6 carbon atoms) and having from 1 to 6 carbon-carbon triple bonds e.g. 1, 2, or 3 carbon-carbon triple bonds. Typical alkynyl groups include ethynyl propargyl (or propynyl, —C≡CCH3), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocylooxy, hydroxyamino, alkoxyamino, nitro, —SO-alkyl, —SO-aryl, —SO-heteroaryl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, cycloalkyl, aryl, heteroaryl, heterocyclyl or where both R groups are joined to form a heterocyclic group (e.g., morpholino). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "ester" or "carboxyester" refers to the group —C(O)OR, where R is alkyl, cycloalkyl, aryl, heteroaryl, or heterocyclyl, which may be optionally further substituted by alkyl, alkoxy, halogen, CF$_3$, amino, substituted amino, cyano, or —S(O)$_n$Ra, in which Ra is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acyloxy" refers to the groups —OC(O)-alkyl, —OC(O)-cycloalkyl, —OC(O)-aryl, —OC(O)-heteroaryl, and —OC(O)-heterocyclyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl, fluorenyl, and anthryl). Typical aryls include phenyl, fluorenyl, naphthyl, anthryl, and the like.

Unless otherwise constrained by the definition for the aryl substituent, such aryl groups can optionally be substituted with 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, amino sulfonyl, aminocarbonyl amino, heteroaryloxy, heterocyclyl, heterocylooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, aryl, heteroaryl and heterocyclyl provided that both R groups are not hydrogen, or a group —Y-Z, in which Y is optionally substituted alkylene and Z is alkenyl, cycloalkenyl, or alkynyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl are as defined herein, and may be optionally further substituted by alkyl, alkenyl, alkynyl, alkoxy, halogen, CF$_3$, amino, substituted amino, cyano, or —S(O)$_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. The term "substituted cycloalkyl" also includes cycloalkyl groups wherein one or more of the annular carbon atoms of the cycloalkyl group is a carbonyl group (i.e. an oxygen atom is oxo to the ring). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to a group comprising 1 to 15 carbon atoms and 1 to 4 heteroatoms selected from oxygen, nitrogen, and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic. Examples of aromatic heteroaryls include pyrrole, thiophene, pyridine, quinoline, pteridine. The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyn-ole, dihydropyridine.

Unless otherwise constrained by the definition for the heteroaryl substituent, such heteroaryl groups can be optionally substituted with 1 to 5 substituents (typically 1, 2, or 3 substituents) selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl (an alkyl ester), arylthio, heteroaryl, heteroarylthio, heterocyclylthio, thiol, alkylthio, aryl, aryloxy, aralkyl, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, SOS alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "heterocyclyl" refers to a monoradical saturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonyl amino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Heterocyclic groups can have a single ring or multiple condensed rings.

Preferred heterocyclics include tetrahydrofuranyl, morpholino, piperidinyl, and the like.

The term "thiol" refers to the group —SH.

The term "substituted alkylthio" refers to the group S-substituted alkyl.

The term "heteroarylthiol" refers to the group S-heteroaryl wherein the heteroaryl group is as defined above including optionally substituted heteroaryl groups as also defined above.

The term "sulfoxide" refers to a group —S(O)$_n$R, in which R is alkyl, aryl, or heteroaryl. "Substituted sulfoxide" refers to a group —S(O)$_n$R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

A compound of a given Formula (e.g. the "compound of Formula (IA) or (IB)") is intended to encompass the compounds of the invention as disclosed, and the pharmaceutically acceptable salts, pharmaceutically acceptable esters, hydrates, polymorphs, and prodrugs of such compounds. Additionally, the compounds of the invention may possess one or more asymmetric centers, and can be produced as a racemic mixture or as individual enantiomers or diastereoisomers. The number of stereoisomers present in any given compound of a given Formula depends upon the number of asymmetric centers present (there are 2n stereoisomers possible where n is the number of asymmetric centers). The individual stereoisomers may be obtained by resolving a racemic or non-racemic mixture of an intermediate at some appropriate stage of the synthesis, or by resolution of the compound by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

The term "therapeutically effective amount" refers to an amount that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
  (i) preventing the disease, that is, causing the clinical symptoms of the disease not to develop;
  (ii) inhibiting the disease, that is, arresting the development of clinical symptoms; and/or
  (iii) relieving the disease, that is, causing the regression of clinical symptoms.

In many cases, the compounds of this invention are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Coronary diseases" or "cardiovascular diseases" refer to diseases of the cardiovasculature arising from any one or more than one of, for example, heart failure (including congestive heart failure, diastolic heart failure and systolic heart failure), acute heart failure, ischemia, recurrent ischemia, myocardial infarction, arrhythmias, angina (including exercise-induced angina, variant angina, stable angina, unstable angina), acute coronary syndrome, diabetes, and intermittent claudication.

"Intermittent claudication" means the pain associated with peripheral artery disease. "Peripheral artery disease" or PAD is a type of occlusive peripheral vascular disease (PVD). PAD affects the arteries outside the heart and brain. The most common symptom of PAD is a painful cramping in the hips, thighs, or calves when walking, climbing stairs, or exercising. The pain is called intermittent claudication. When listing the symptom intermittent claudication, it is intended to include both PAD and PVD Arrhythmia refers to any abnormal heart rate. Bradycardia refers to abnormally slow heart rate whereas tachycardia refers to an abnormally rapid heart rate. As used herein, the treatment of arrhythmia is intended to include the treatment of supra ventricular tachycardias such as atrial fibrillation, atrial flutter, AV nodal reentrant tachycardia, atrial tachycardia, and the ventricular tachycardias (VTs), including idiopathic ventricular tachycardia, ventricular fibrillation, pre-excitation syndrome, and Torsade de Pointes (TdP), Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

Compounds of Formula (IA) and (IB) are described herein with reference to various chemical variable groups, e.g. those designated $R^1$, $R^2$, $R^3$, $R^4$, $R^5$, $R^6$, $R^7$, $R^{20}$, $R^{22}$, $R^{25}$, $R^{26}$, or $R^a$. In general, each of the chemical variable groups may be independently selected with respect to each of the other chemical variable groups. The descriptions of each of these groups herein include many possible named or described chemical fragments. In some cases, one or more of the named or described chemical fragments in a list of named or described chemical fragments that is part of a description of a chemical variable group may be omitted from the list of named or described chemical fragments. In certain cases, possible identity of a chemical variable group (e.g. those listed at the beginning of this paragraph) may be limited to only portions of a list of named or described chemical fragments associated with that chemical variable group.

Nomenclature

Names of compounds of the present invention are provided using ACD/Name software for naming chemical compounds (Advanced Chemistry Development, Inc., Toronto). Other compounds or radicals may be named with common names, or systematic or non-systematic names. The naming and numbering of the compounds of the invention is illustrated with a representative compound of Formula (IA)

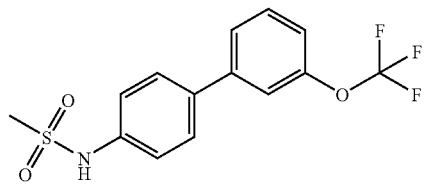 [SMILES: CS(=O)(=O)Nc1ccc(-c2cccc(OC(F)(F)F)c2)cc1]

which is named N-[3'-(trifluoromethoxy)biphenyl-4-yl] methanesulfonamide.

Compounds of Formula (IA) and (IB)

Accordingly, in typical embodiments the present invention provides compounds that function as sodium channel blockers. In typical embodiments the invention relates to compounds of Formula (IA) or (IB):

Formula (IA)

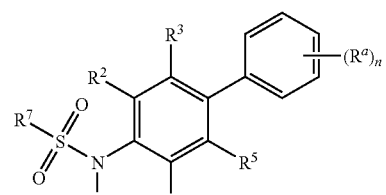

Formula (IB)

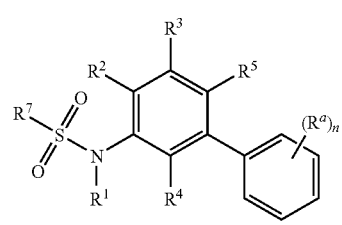

wherein:
$R^1$ is hydrogen, $C_{1-4}$ alkyl, $-R^{25}-O-R^{20}$, $-R^{25}-C(O)-O-R^{20}$, $-R^{25}-C(O)NHS(O)_2R^{20}$, $-R^{25}$-optionally substituted monocyclic heterocyclyl, $-R^{25}$-optionally substituted monocyclic cycloalkyl $-R^{25}$-optionally substituted monocyclic heteroaryl, $-R^{25}$-optionally substituted monocyclic aryl,
  wherein the heterocyclyl, cycloalkyl, aryl, and heteroaryl are optionally substituted with one, two, or three substituents independently selected from halo, hydroxyl, alkyl, $-R^{25}-C(O)-O-R^{20}$, $-R^{25}-S(O)_2-R^{20}$, lower alkoxy, $-CF_3$, $-CN$, amino, $-NO_2$, mono- or dialkylamino, and heteroaryl;
$R^2$ and $R^5$ are each independently selected from the group consisting of hydrogen, $C_{1-4}$ alkyl, halo, CN, $-CF_3$, $-O-R^{20}$, $-S-R^{20}$, $-C(O)-O-R^{20}$, $-C(O)-N(R^{20})(R^{22})$, and $-P(O)(OR^{20})_2$;
$R^3$ and $R^4$ are hydrogen;
$R^7$ is $C_{1-4}$ alkyl or cycloalkyl;
$R^a$ are each independently selected from the group consisting of $C_{1-4}$ alkyl, halo, CN, $-NO_2$, $CF_3$, $-O-R^{20}$, —S—$R^{20}$, —C(O)—O—$R^{20}$, —C(O)—N($R^{20}$)($R^{22}$), —N($R^{20}$)($R^{22}$), —N($R^{20}$)($R^{22}$), —N($R^{20}$)—C(O)—$R^{22}$, —P(O)(O$R^{20}$)$_2$, —$R^{25}$-optionally substituted monocyclic heteroaryl, —$R^{25}$-optionally substituted monocyclic aryl;
  wherein the aryl and heteroaryl are optionally substituted with one, two, or three substituents independently selected from halo, hydroxyl, alkyl, mono- or dialkylamino, alkyl or aryl or heteroaryl amide, —CN, lower alkoxy, —CF$_3$, aryl, and heteroaryl;

n is 0, 1, 2, or 3;

$R^{20}$ and $R^{22}$ are in each instance independently selected from the group consisting of hydrogen, $C_1$-$C_{15}$ alkyl, $C_2$-$C_{15}$ alkenyl, $C_2$-$C_{15}$ alkynyl, heterocyclyl, aryl, and heteroaryl,
  wherein the alkyl, alkenyl, alkynyl, heterocyclyl, aryl, and heteroaryl are optionally substituted with one, two, or three substituents independently selected from halo, hydroxyl, alkyl, mono- or dialkylamino, alkyl or aryl or heteroaryl amide, —CN, lower alkoxy, —CF$_3$, aryl, and heteroaryl;

$R^{25}$ is in each instance independently a covalent bond or selected from $C_1$-$C_3$ alkylene optionally substituted with one or two $C_1$-$C_3$ alkyl groups;

with the provisos that when the compound has the structure of Formula (IA) and $R^7$ is $C_{1-4}$ alkyl and:
  1) $R^1$ is CH$_2$COOH, heteroaryl, or halo-substituted benzyl, then not all of $R^2$-$R^5$ can be hydrogen;
  2) $R^1$ is CH(CH$_3$)COOCH$_2$CH$_3$, then at least one of n or m is not 0;
  3) $R^1$ is hydrogen or methyl, then
    a) at least one of $R^a$ and $R^b$ is —O$R^{26}$ where
      $R^{26}$ is heterocyclyl, aryl, or heteroaryl,
        wherein the heterocyclyl, aryl, and heteroaryl are optionally substituted with one, two, or three substituents independently selected from halo, hydroxyl, alkyl, mono- or dialkylamino, alkyl or aryl or heteroaryl amide, —CN, lower alkoxy, —CF$_3$, aryl, and heteroaryl; and
    b) when n is 1 and $R^a$ is unsubstituted phenoxy, then $R^a$ is not attached at the meta position or a pharmaceutically acceptable salt, ester, prodrug, or solvate thereof.

In typical embodiments, $R^1$ is hydrogen or —$R^{25}$—C(O)—O—$R^{20}$, —$R^{25}$-optionally substituted monocyclic heteroaryl, or optionally substituted aryl. When not a covalent bond, $R^{25}$ is typically methylene. Common optionally substituted cycloalkyl, heteroaryl, heterocyclyl, and aryl substituents include, but are not limited to, methylpiperazinyl, morpholinyl, piperidnyl, tetrazolyl, hydroxycylopentyl, pyridinyl, and phenyl.

In many embodiments $R^1$ is —$R^{25}$—O—$R^{20}$, —$R^{25}$—C(O)—O—$R^{20}$, —$R^{25}$-optionally substituted monocyclic heterocyclyl, —$R^{25}$-optionally substituted monocyclic cycloalkyl —$R^{25}$-optionally substituted monocyclic heteroaryl, —$R^{25}$-optionally substituted monocyclic aryl, wherein the heterocyclyl, cycloalkyl, aryl, and heteroaryl are optionally substituted with one, two, or three substituents independently selected from halo, hydroxyl, alkyl, —$R^{25}$—C(O)—O—$R^{20}$, —$R^{25}$—S(O)$_2$—$R^{20}$, lower alkoxy, —CF$_3$, —CN, amino, —NO$_2$, mono- or dialkylamino, and heteroaryl; and $R^{25}$ is $C_1$-$C_3$ alkylene optionally substituted with one or two $C_1$-$C_3$ alkyl groups.

In many common embodiments $R^1$ is $R^{25}$-phenyl, wherein the phenyl ring is optionally substituted with one, two, or three substituents independently selected from halo, hydroxyl, alkyl, —$R^{25}$—C(O)—O—$R^{20}$, —$R^{25}$—S(O)$_2$—$R^{20}$, lower alkoxy, —CF$_3$, —CN, amino, —NO$_2$, mono- or dialkylamino, and heteroaryl.

$R^2$ and $R^5$ moieties are commonly hydrogen, methyl, Cl, F, CF$_3$, CN, NH$_2$, OCH$_3$, —COOH, —COOCH$_3$, —CONHCH$_3$, —CONHCH/CH$_2$OH, —COHNCH(CH$_3$)$_2$, NHCO pyridinyl, or tetrazolyl.

$R^7$ is commonly cycloalkyl and typically $R^7$ moieties include, but are not limited to, methyl, ethyl, and cyclopropyl.

$R^a$ may commonly be Cl, F, CN, CF$_3$, —OCF$_3$, —OCH$_3$, methyl, ethyl, NO$_2$, optionally substituted phenoxy, —COOCH$_3$, tetrazolyl, or isopropoxy.

In those embodiments when $R^1$ is substituted aryl, such as substituted phenyl, common substituents include, but are not limited to, halo, hydroxyl, alkyl, mono- or dialkylamino, alkyl or aryl or heteroaryl amide, —CN, lower alkoxy, —CF$_3$, aryl, and heteroary.

Further Embodiments

In typical embodiments, the compounds provided by the present invention are effective in the treatment of conditions known to respond to administration of late sodium channel blockers, including but not limited to cardiovascular diseases such as atrial and ventricular arrhythmias, including atrial fibrillation, Prinzmetal's (variant) angina, stable angina, unstable angina, ischemia and reperfusion injury in cardiac, kidney, liver and the brain, exercise induced angina, congestive heart disease including diastolic and systolic heart failure, and myocardial infarction. In some embodiments, compounds provided by the present invention which function as late sodium channel blockers may be used in the treatment of diseases affecting the neuromuscular system resulting in pain, itching, seizures, or paralysis, or in the treatment of diabetes or reduced insulin sensitivity, and disease states related to diabetes, such as diabetic peripheral neuropathy.

Certain compounds of the invention may also possess a sufficient activity in modulating neuronal sodium channels and may have appropriate pharmacokinetic properties such that they may active with regard to the central and/or peripheral nervous system. Consequently, some compounds of the invention may also be of use in the treatment of pain or itching of a neuropathic origin.

In typical embodiments, the present invention is intended to encompass the compounds disclosed herein, and the pharmaceutically acceptable salts, pharmaceutically acceptable esters, tautomeric forms, polymorphs, and prodrugs of such compounds. In some embodiments, the present invention includes a pharmaceutically acceptable addition salt, a pharmaceutically acceptable ester, a hydrate of an addition salt, a tautomeric form, a polymorph, an enantiomer, a mixture of enantiomers, a stereoisomer or mixture of stereoisomers (pure or as a racemic or non-racemic mixture) of a compound described herein, e.g. a compound of Formula (I); such as a compound of Formula (I) named herein.

Pharmaceutical Compositions and Administration

Compounds provided in accordance with the present invention are usually administered in the form of pharmaceutical compositions. This invention therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G.S. Banker & C.T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g of a compound described herein, and for parenteral administration, preferably from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Combination Therapy

Coronary patients being treated for an acute cardiovascular disease event by administration of ranolazine often exhibit diseases or conditions that benefit from treatment with other therapeutic agents. These diseases or conditions can be of the cardiovascular nature or can be related to pulmonary disorders, metabolic disorders, gastrointestinal disorders and the like. Additionally, some coronary patients being treated for an acute cardiovascular disease event by administration of ranolazine exhibit conditions that can benefit from treatment with therapeutic agents that are antibiotics, analgesics, and/or anti-depressants and anti-anxiety agents.

Cardiovascular Agent Combination Therapy

Cardiovascular related diseases or conditions that can benefit from a combination treatment of ranolazine with other therapeutic agents include, without limitation, angina including stable angina, unstable angina (UA), exercised-induced angina, variant angina, arrhythmias, intermittent claudication, myocardial infarction including non-STE myocardial infarction (NSTEMI), heart failure including congestive (or chronic) heart failure, acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of ranolazine with therapeutic agents suitable for treating cardiovascular related conditions allows enhancement in the standard of care therapy the patient is currently receiving.

Anti-Anginals

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral), atenolol (Tenormin), betaxolol (Kerlone), bisoprolol/hydrochlorothiazide (Ziac), bisoprolol (Zebeta), carteolol (Cartrol), esmolol (Brevibloc), labetalol (Normodyne, Trandate), metoprolol (Lopressor, Toprol XL), nadolol (Corgard), propranolol (Inderal), sotalol (Betapace), and timolol (Blocadren).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc, Lotrel), bepridil (Vascor), diltiazem (Cardizem, Tiazac), felodipine (Plendil), nifedipine (Adalat, Procardia), nimodipine (Nimotop), nisoldipine (Sular), verapamil (Calan, Isoptin, Verelan), and nicardipine.

Heart Failure Agents

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn), furosemide (Lasix), bumetanide (Bumex), spironolactone (Aldactone), and eplerenone (Inspra).

Angiotensin converting enzyme (ACE) inhibitors reduce the workload on the heart by expanding the blood vessels and decreasing resistance to blood flow. Examples of ACE inhibitors include benazepril (Lotensin), captopril (Capoten), enalapril (Vasotec), fosinopril (Monopril), lisinopril (Prinivil, Zestril), moexipril (Univasc), perindopril (Aceon), quinapril (Accupril), ramipril (Altace), and trandolapril (Mavik).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotic Agents

Antithrombotics inhibit the clotting ability of the blood. There are three main types of antithrombotics—platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (plavix), dipyridamole, cilostazol, persantine sulfinpyrazone, dipyridamole, indomethacin, and glycoprotein llb/llla inhibitors, such as abciximab, tirofiban, and eptifibatide (Integrelin). Beta blockers and calcium channel blockers also have a platelet-inhibiting effect.

Anticoagulants prevent blood clots from growing larger and prevent the formation of new clots. Examples of anticoagulants include bivalirudin (Angiomax), warfarin (Coumadin), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic Agents

Antiarrhythmic agents are used to treat disorders of the heart rate and rhythm. Examples of antiarrhythmic agents include amiodarone, quinidine, procainamide, lidocaine, and propafenone. Cardiac glycosides and beta blockers are also used as antiarrhythmic agents.

Antihypertensive Agents

Antihypertensive agents are used to treat hypertension, a condition in which the blood pressure is consistently higher than normal. Hypertension is associated with many aspects of cardiovascular disease, including congestive heart failure, atherosclerosis, and clot formation. Examples of antihypertensive agents include alpha-1-adrenergic antagonists, such as prazosin (Minipress), doxazosin mesylate (Cardura), prazosin hydrochloride (Minipress), prazosin, polythiazide (Minizide), and terazosin hydrochloride (Hytrin); beta-adrenergic antagonists, such as propranolol (Inderal), nadolol (Corgard), timolol (Blocadren), metoprolol (Lopressor), and pindolol (Visken); central alpha-adrenoceptor agonists, such as clonidine hydrochloride (Catapres), clonidine hydrochloride and chlorthalidone (Clorpres, Combipres), guanabenz Acetate (Wytensin), guanfacine hydrochloride (Tenex), methyldopa (Aldomet), methyldopa and chlorothiazide (Aldoclor), methyldopa and hydrochlorothiazide (Aldoril); combined alpha/beta-adrenergic antagonists, such as labetalol (Normodyne, Trandate), Carvedilol (Coreg); adrenergic neuron blocking agents, such as guanethidine (Ismelin), reserpine (Serpasil); central nervous system-acting antihypertensives, such as clonidine (Catapres), methyldopa (Aldomet), guanabenz (Wytensin); anti-angiotensin II agents; ACE inhibitors, such as perindopril (Aceon) captopril (Capoten), enalapril (Vasotec), lisinopril (Prinivil, Zestril); angiotensin-II receptor antagonists, such as Candesartan (Atacand), Eprosartan (Teveten), Irbesartan (Avapro), Losartan (Cozaar), Telmisartan (Micardis), Valsartan (Diovan); calcium channel blockers, such as verapamil (Calan, Isoptin), diltiazem (Cardizem), nifedipine (Adalat, Procardia); diuretics; direct vasodilators, such as nitroprusside (Nipride), diazoxide (Hyperstat IV), hydralazine (Apresoline), minoxidil (Loniten), verapamil; and potassium channel activators, such as aprikalim, bimakalim, cromakalim, emakalim, nicorandil, and pinacidil.

Lipid Lowering Agents

Lipid lowering agents are used to lower the amounts of cholesterol or fatty sugars present in the blood. Examples of lipid lowering agents include bezafibrate (Bezalip), ciprofibrate (Modalim), and statins, such as atorvastatin (Lipitor), fluvastatin (Lescol), lovastatin (Mevacor, Altocor), mevastatin, pitavastatin (Livalo, Pitava) pravastatin (Lipostat), rosuvastatin (Crestar), and simvastatin (Zocor).

In this invention, the patient in need of the late sodium channel blocker often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient the compounds of the invention in combination with at least one therapeutic agent.

Pulmonary Disorders

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire, Bricanyl), albuterol (Proventil), salmeterol (Serevent, Serevent Diskus), theophylline, ipratropium bromide (Atrovent), tiotropium (Spiriva), methylprednisolone (Solu-Medrol, Medrol), magnesium, and potassium.

Metabolic Disorders

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral Vascular Disorders

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal Disorders

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix), lansoprazole (Prevacid), esomeprazole (Nexium), omeprazole (Prilosec), rabeprazole; H2 blockers, such as cimetidine (Tagainet), ranitidine (Zantac), famotidine (Pepcid), nizatidine (Axid); prostaglandins, such as misoprostoL (Cytotec); sucralfate; and antacids.

Antibiotics, Analgesics, Antidepressants and Anti-Anxiety Agents

Patients presenting with an acute coronary disease event may exhibit conditions that benefit from administration of therapeutic agent or agents that are antibiotics, analgesics, antidepressant and anti-anxiety agents in combination with ranolazine.

Antibiotics

Antibiotics are therapeutic agents that kill, or stop the growth of microorganisms, including both bacteria and fungi. Example of antibiotic agents include β-Lactam antibiotics, including penicillins (amoxicillin), cephalosporins, such as cefazolin, cefuroxime, cefadroxil (Duricef), cephalexin (Keflex), cephradine (Velosef), cefaclor (Ceclor), cefuroxime axtel (Ceftin), cefprozil (Cefzil), loracarbef (Lorabid), cefixime (Suprax), cefpodoxime proxetil (Vantin), ceftibuten (Cedax), cefdinir (Omnicef), ceftriaxone (Rocephin), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinoes, such as linezolid; and sulfa antibiotics, such as sulfisoxazole.

Analgesics

Analgesics are therapeutic agents that are used to relieve pain. Examples of analgesics include opiates and morphinomimetics, such as fentanyl and morphine; paracetamol; NSAIDs, and COX-2 inhibitors.

Antidepressant and Anti-Anxiety Agents

Antidepressant and anti-anxiety agents include those agents used to treat anxiety disorders, depression, and those used as sedatives and tranquillers. Examples of antidepressant and anti-anxiety agents include benzodiazepines, such as diazepam, lorazepam, and midazolam; enzodiazepines; barbiturates; glutethimide; chloral hydrate; meprobamate; sertraline (Zoloft, Lustral, Apo-Sertral, Asentra, Gladem, Serlift, Stimuloton); escitalopram (Lexapro, Cipralex); fluoxetine (Prozac, Sarafem, Fluctin, Fontex, Prodep, Fludep, Lovan); venlafaxine (Effexor XR, Efexor); citalopram (Celexa, Cipramil, Talohexane); paroxetine (Paxil, Seroxat, Aropax); trazodone (Desyrel); amitriptyline (Elavil); and bupropion (Wellbutrin, Zyban).

Synthesis of Example Compounds

The compounds of the invention may be prepared using methods disclosed herein and routine modifications thereof which will be apparent given the disclosure herein and methods well known in the art. Conventional and well-known synthetic methods may be used in addition to the teachings herein. The synthesis of typical compounds described herein, e.g. compounds having structures described by one or more of Formula (IA) or (IB), may be accomplished as described in the following examples. If available, reagents may be purchased commercially, e.g. from Sigma Aldrich or other chemical suppliers.

General Syntheses:

Typical embodiments of compounds in accordance with the present invention may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments of the present invention, inspection of the structure of the compound to be synthesized will provide the identity of each substituent group. The identity of the final product will generally render apparent the identity of the necessary starting materials by a simple process of inspection, given the examples herein.

Synthetic Reaction Parameters

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present invention are inert organic solvents, and the reactions are carried out under an inert gas, preferably nitrogen.

The term "q.s." means adding a quantity sufficient to achieve a stated function, e.g., to bring a solution to the desired volume (i.e., 100%).

Synthesis of the Compounds of Formula (I)

The compounds of Formula (IA) and (IB) are typically prepared by first reacting an aniline starting material (1); which may be commercially obtained, for example 4-bromoaniline, and the like, or synthesized de novo, with a sulfonyl chloride compound, $ClS(O)_2R^7$ to form intermediate sulfonamide compound (2). Once the sulfonamide group has been added, a suitably substituted second phenyl ring is then attached using conditions known as Suzuki coupling. This is process is show below in Reaction Scheme I for a compound of Formula (IA).

REACTION SCHEME I

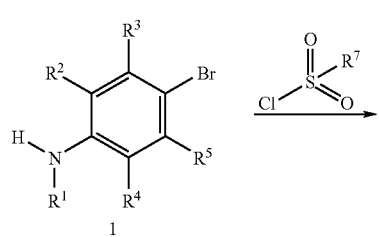

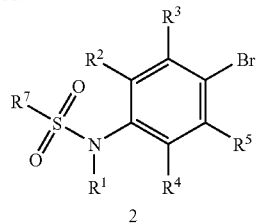

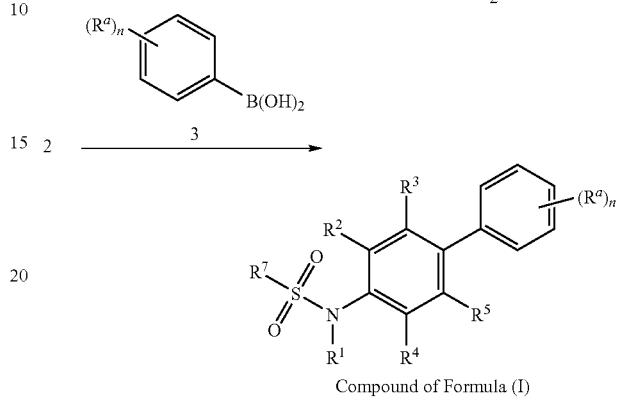

Compound of Formula (I)

Referring to the above Scheme I, aniline 1 is first dissolved in an organic solvent, preferably $CH_2Cl_2$ or DMF, to which is then added a base such as pyridine at a temperature between −30° C. and 50° C., followed by the substituted sulfonyl chloride. The resulting mixture is then stirred at a temperature between −30° C. and 70° C. for 1 to 48 hrs, and concentrated. The residue may be purified by column chromatography via silica gel, or by precipitating out of water, followed by washing with water and organic solvent such as ethyl ether to provide the intermediate (2).

Once synthesized, the halogenated intermediate (2), in this case a brominated compound, is reacted with an appropriately substituted boronic acid derivative (3) in an inert solvent, for example aqueous N,N-dimethylformamide, in the presence of a mild base, for example sodium bicarbonate. The reaction is typically conducted in the presence of a metal catalyst with an appropriate ligand, for example dichlorobis(triphenylphosphine) palladium(II), at a temperature of about 25° C. and 150° C. for 1 to 24 hrs, or microwave heating at a temperature between 100° C. and 200° C., preferably at around 140° C. for 5 to 30 min. When the reaction is substantially complete, the product of Formula (IA) or (IB) is isolated by conventional means.

It will be appreciated that various R substituents can be modified or added either before or after the addition of either the sulfonamide moiety or the second phenyl ring. For example, in certain embodiments when $R^1$ is H, an $R^1$ cyanomethyl group may be added by reaction with iodoacetonitrile in $CH_3CN$. The resulting compound of Formula I may then be further reacted with $NaN_3$ and $ZnBr_2$ to convert the terminal cyano moiety into a tetrazol ring.

Another possible modification of the $R^1$ moiety when R' is initially hydrogen involves reaction with a hydroxyl substituted reactant having the desired $R^1$ moiety. This type of reaction is generally conducted using diethylazodicarboxylate and is typically conducted using ice-bath conditions. Other possible routes of modification will be readily apparent to one of ordinary skill in the art and additional examples are present in the Examples that follow.

It will also be appreciated that the addition of any substituent may result in the production of a number of isomeric products any or all of which may be isolated and purified using conventional techniques.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of a Compound of Formula (Ia)

A. Preparation of a Compound of Formula I in which $R^1$, $R^2$, $R^3$, and $R^4$ are hydrogen, $R^5$ is Cl, $R^7$ is $CH_3$, n is 2, and $R^a$ are Cl and F

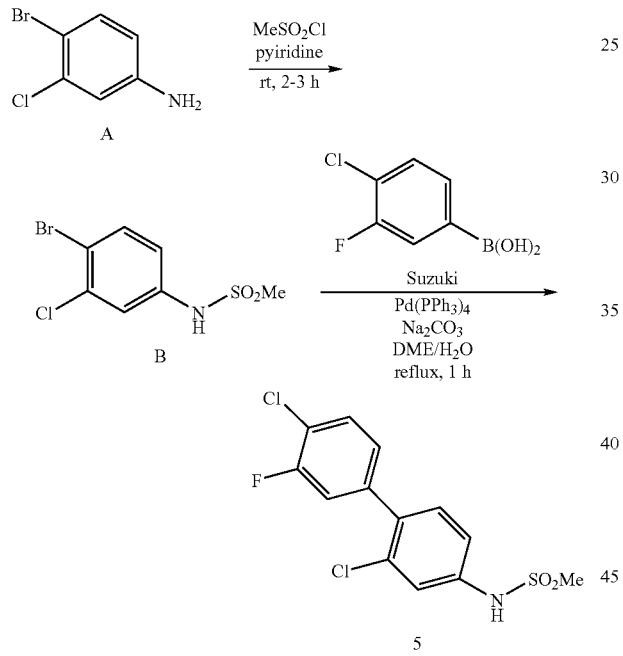

Step 1. Preparation of N-(4-bromo-3-chlorophenyl)methanesulfonamide, a compound of formula (2)

In a 100 mL round bottomed flask 4-bromo-3-chloroaniline (A, 2.06 g, 10.0 mmol) was dissolve in pyridine (30 mL) at room temperature. Methanesulfonyl chloride (1.72 g, 15.0 mmol, 1.5 equiv) was added under an ice-water bath cooling. The ice bath was removed immediately after addition of the reagent. After stirring for 1.5 h, another methanesulfonyl chloride (0.57 g, 5.0 mmol, 0.5 equiv) was added at room temperature for the reaction to go to completion. After stirring for 0.5 h, the mixture was treated with $H_2O$ (50 mL) and extracted with EtOAc (50 mL×3). Combined organic layers were washed with brine (50 mL×2) and dried over $Na_2SO_4$. The solvent was removed in vacuo to give the crude material (very light brown solid, 5.32 g). The crude product was purified by a silica gel column chromatography ($SiO_2$=80 g, EtOAc/hexane=1:1, Rf=0.3) to give the desired product as colorless crystals. The obtained crystals were recrystallized from EtOAc/hexane=1:2 (24 mL) to give the desired material [N-(4-bromo-3-chlorophenyl)methanesulfonamide (B)].

TLC: Rf=0.3 ($SiO_2$, EtOAc/hexane=1:1),

LCMS (EI: 70 eV) 357 ($M^+$+Na), 334 ($M^+$).

Step 2. Preparation of N-(2,4'-dichloro-3'-fluorobiphenyl-4-yl)methanesulfonamide N-(4-bromo-3-chlorophenyl)methanesulfonamide (B, 100.0 mg, 0.351 mmol), 4-chloro-3-fluorophenylboronic acid (73.4 mg, 0.421 mmol, L2 equiv.) and $Pd(PPh_3)_4$ (20.3 mg, 0.0176 mmol, 0.05 equiv.) was placed in a 50 mL round bottomed flask under a nitrogen atmosphere. To the flask were added 2M-$Na_1CO_3$ (1.0 mL, 2.0 mmol, 5.7 equiv.) and DME (4 mL) subsequently at ambient temperature. The mixture was heated under reflux conditions for 1 hours. The mixture was filtered through Celite (3 g) and the Celite was washed with EtOAc (70 mL). The solvent was removed under a reduced pressure. Obtained crude mixture was purified by column chromatography ($SiO_2$=80 g, EtOAc/hexane=1:3~1:1, Rf=0.4) to give the desired product as colorless crystals (compound 5 (designated PT-017).

TLC: Rf=0.4 ($SiO_2$, EtOAc/hexane—-1:1),

LCMS (EI: 70 eV) 307 ($M^+$+Na).

B. Preparation of Compounds of Formula I varying $R^5$ and $R^a$

Similarly, following the procedure of Example 1A above, but optionally substituting other boronic acids for 4-chloro-3-fluorophenylboronic acid and/or substituting other compounds of formula (1), either commercially obtained or prepared using different analines or other sulfonyl chlorides, the following compounds of Formula (IA) were prepared:

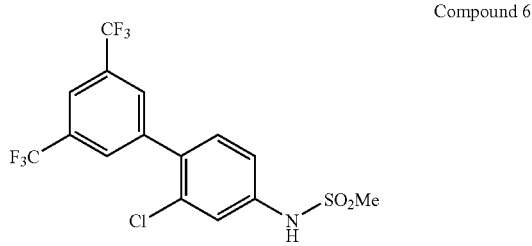

Compound 6

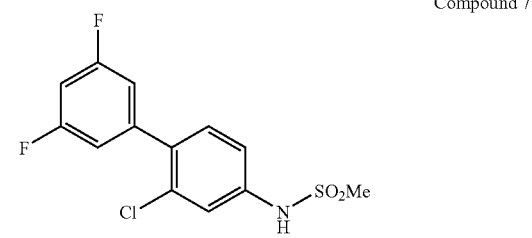

Compound 7

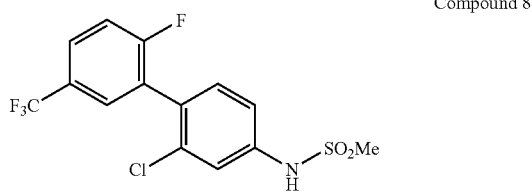

Compound 8

-continued

Compound 9

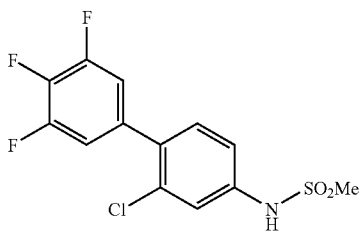

Compound 10

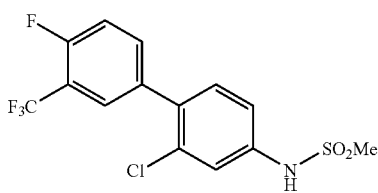

Compound 6 is designated PT-065, Compound 7 is designated PT-068, Compound 8 is designated PT-070, Compound 9 is designated PT-071, and Compound 10 is designated PT-069.

PT-010:

[PT-010 structure]

$^{1}$H-NMR (CD$_{3}$OD) δ 3.02 (s, 3H), 3.82 (s, 3H), 6.92-6.95 (m, 1H), 7.01 (d, 1H, J=4.00 Hz), 7.18-7.21 (m, 1H), 7.29 (d, 1H, J=8.00 Hz), 7.38-7.40 (m, 1H), 7.45-7.47 (m, 2H)

PT-022:

[PT-022 structure]

$^{1}$H-NMR (CD$_{3}$OD) δ 3.05 (s, 3H), 7.24-7.29 (m, 2H), 7.35-7.44 (m, 4H), 7.51 (td, 1H, J=8.00, 2.00 Hz)

TABLE 1

| (PT-nnn) | Name of compound |
|---|---|
| PT-003 | N-(4'-chloro-3'-fluoro-2-methoxybiphenyl-4-yl)methanesulfonamide |
| PT-004 | N-[2-methoxy-4'-(trifluoromethyl)biphenyl-4-yl]methanesulfonamide |
| PT-005 | N-(4'-chloro-3'-fluorobiphenyl-4-yl)methanesulfonamide |
| PT-006 | N-[4'-(trifluoromethyl)biphenyl-4-yl]methanesulfonamide |
| PT-007 | N-(3'-chloro-4'-fluorobiphenyl-4-yl)methanesulfonamide |
| PT-008 | N-[3'-(trifluoromethoxy)biphenyl-4-yl]methanesulfonamide |
| PT-009 | N-[2-methoxy-4'-(trifluoromethoxy)biphenyl-4-yl]methanesulfonamide |
| PT-010 | N-[2-methoxy-3'-(trifluoromethoxy)biphenyl-4-yl]methanesulfonamide |
| PT-011 | N-[2-methoxy-2'-(trifluoromethoxy)biphenyl-4-yl]methanesulfonamide |
| PT-012 | N-[4'-chloro-3'-fluoro-2-(trifluoromethyl)biphenyl-4-yl]methanesulfonamide |
| PT-013 | N-[2,4'-bis(trifluoromethyl)biphenyl-4-yl]methanesulfonamide |
| PT-014 | N-[4'-(trifluoromethoxy)-2-(trifluoromethyl)biphenyl-4-yl]methanesulfonamide |
| PT-015 | N-[3'-(trifluoromethoxy)-2-(trifluoromethyl)biphenyl-4-yl]methanesulfonamide |
| PT-016 | N-[2'-(trifluoromethoxy)-2-(trifluoromethyl)biphenyl-4-yl]methanesulfonamide |
| PT-017 | N-(2,4'-dichloro-3'-fluorobiphenyl-4-yl)methanesulfonamide |
| PT-018 | N-[2-chloro-4'-(trifluoromethyl)biphenyl-4-yl]methanesulfonamide |
| PT-021 | N-[2-chloro-3'-(trifluoromethoxy)biphenyl-4-yl]methanesulfonamide |
| PT-022 | N-[2-chloro-2'-(trifluoromethoxy)biphenyl-4-yl]methanesulfonamide |
| PT-023 | N-(2-chloro-3',4'-difluorobiphenyl-4-yl)methanesulfonamide |
| PT-024 | N-(2-chloro-2',4'-difluorobiphenyl-4-yl)methanesulfonamide |
| PT-026 | N-(2,4'-dichloro-3'-fluorobiphenyl-4-yl)ethanesulfonamide |
| PT-027 | N-(2,4'-dichloro-3'-fluorobiphenyl-4-yl)propane-1-sulfonamide |
| PT-031 | N-(4'-fluoro-2-methoxybiphenyl-4-yl)methanesulfonamide |
| PT-032 | N-(4'-chloro-2-methoxybiphenyl-4-yl)methanesulfonamide |
| PT-035 | N-(2-chloro-2'-fluorobiphenyl-4-yl)methanesulfonamide |
| PT-036 | N-[2-chloro-3'-(trifluoromethyl)biphenyl-4-yl]methanesulfonamide |
| PT-037 | N-(2-chloro-4'-fluorobiphenyl-4-yl)methanesulfonamide |
| PT-038 | N-(2,3'-dichloro-4'-fluorobiphenyl-4-yl)methanesulfonamide |
| PT-043 | N-(2,4'-dichlorobiphenyl-4-yl)methanesulfonamide |
| PT-044 | methyl 2'-chloro-4'-[(methylsulfonyl)amino]biphenyl-4-carboxylate |
| PT-045 | N-(2,2'-dichloro-4'-fluorobiphenyl-4-yl)methanesulfonamide |
| PT-051 | N-(2-chloro-4'-methoxybiphenyl-4-yl)methanesulfonamide |
| PT-052 | N-(2-chloro-3'-fluorobiphenyl-4-yl)methanesulfonamide |
| PT-053 | N-(2,3'-dichlorobiphenyl-4-yl)methanesulfonamide |
| PT-054 | N-(2-chloro-3'-nitrobiphenyl-4-yl)methanesulfonamide |
| PT-058 | N-[2,4'-dichloro-3'-(trifluoromethyl)biphenyl-4-yl]methanesulfonamide |
| PT-059 | N-(4'-chloro-2,3'-difluorobiphenyl-4-yl)methanesulfonamide |
| PT-065 | N-[2-chloro-3',5'-bis(trifluoromethyl)biphenyl-4-yl]methanesulfonamide |
| PT-067 | N-[2-fluoro-3'-(trifluoromethoxy)biphenyl-4-yl]methanesulfonamide |
| PT-068 | N-(2-chloro-3',5'-difluorobiphenyl-4-yl)methanesulfonamide |
| PT-069 | N-[2-chloro-4'-fluoro-3'-(trifluoromethyl)biphenyl-4-yl]methanesulfonamide |
| PT-070 | N-[2-chloro-2'-fluoro-5'-(trifluoromethyl)biphenyl-4-yl]methanesulfonamide |

TABLE 1-continued

| (PT-nnn) | Name of compound |
|---|---|
| PT-071 | N-(2-chloro-3',4',5'-trifluorobiphenyl-4-yl)methanesulfonamide |
| PT-078 | N-[2-fluoro-4'-(trifluoromethoxy)biphenyl-4-yl]methanesulfonamide |
| PT-079 | N-[2-fluoro-3'-(trifluoromethyl)biphenyl-4-yl]methanesulfonamide |
| PT-080 | N-[2-fluoro-4'-(trifluoromethyl)biphenyl-4-yl]methanesulfonamide |
| PT-086 | N-[4'-(trifluoromethoxy)biphenyl-4-yl]methanesulfonamide |
| PT-094 | N-[2-chloro-4'-(trifluoromethoxy)biphenyl-4-yl]methanesulfonamide |

C. Preparation of Compounds of Formula (IA) and (IB) varying $R^1$, $R^2$, and $R^3$ Similarly, following the procedure of Example 1A above, but optionally substituting other boronic acids for 4-chloro-3-fluorophenylboronic acid and/or substituting other compounds of formula (1), either commercially obtained or prepared using different analines or other sulfonyl chlorides, other compounds of Formula (IA) or (IB) may be prepared.

Example 2

Preparation of a Compound of Formula (Ia)

A. Preparation of a Compound of Formula I in which $R^1$, $R^2$, $R^3$, and $R^4$ are Hydrogen, $R^5$ and $R^7$ are $CH_3$, n is 1, and $R^a$ is —$OCF_3$

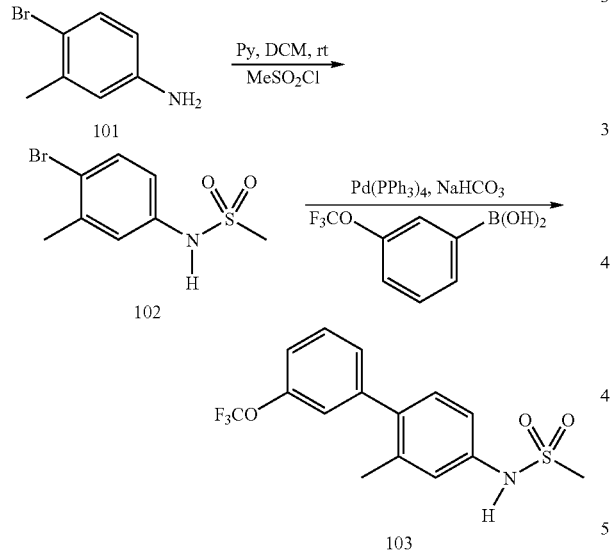

Step 1. Preparation of N-(4-bromo-3-methylphenyl)methanesulfonamide, a compound of formula (1)

To a stirred solution of 4-bromo-3-methylaniline 4 (7.442 g, 40.0 mmol) in $CH_2Cl_2$ (40 mL) was added pyridine (4.86 mL, 60.0 mmol), followed by methanesulfonyl chloride (4.65 mL, 60.0 mmol). The resulting mixture was stirred at room temperature for 15 hrs. The pink yellow solution was concentrated in vacuo, 0.5N aqueous HCl (60 mL) was added, stirred and sonicated, filtered, washed with 0.5N HCl (100 mL), $H_2O$ (100 mL) and n-hexane (80 mL), dried to give pink solid 102.

LCMS mz 285.8 (M+Na), 287.9 (M+Na+2).

$^1$H NMR (400 MHz; $CDCl_3$) δ7.50 (d, J=8.6 Hz, 1H); 7.11 (d, J=2.5 Hz, 1H); 6.94 (dd, J=8.4 and 2.5 Hz, 1H); 6.47 (s, 1H); 3.01 (s, 3H); 2.39 (s, 3H).

Step 2. Preparation of N-(2-methyl-3'-(trifluoromethoxy)biphenyl-4-yl)methanesulfonamide, a compound of Formula (IA)

To a solution of 102 (264 mg, 1.00 mmol) and 3-(trifluoromethoxy)phenylboronic acid (248 mg, 1.20 mmol) in DMF (2.5 mL) was added $NaHCO_3$ (252 mg, 3.00 mmol) and $H_2O$ (0.5 mL). The reaction mixture was stirred for 5 min under an atmosphere of dry $N_2$. $Pd(PPh_3)_4$ (59 mg, 0.05 mmol) was added, and the resulting mixture was irradiated with microwave at 140° C. for 25 min. After the reaction was completed, the mixture was filtered through celite, eluted with EtOAc (40 mL). The organic phase was washed with $H_2O$ (30 mL), 30% $NH_4Cl$ (30 mL), brine (40 mL), and concentrated. The crude product was purified by preparative HPLC with a gradient MeCN in $H_2O$ (5-98%) to give compound 103 (designated PT-040).

MS mz 346.1 (M+H).

$^1$H NMR (400 MHz; $CDCl_3$) δ7.44 (t, J=7.8 Hz, 1H); 7.18-7.25 (m, 3H); 7.06-7.17 (m, 3H); 6.40 (s, 1H); 3.07 (s, 3H); 2.67 (s, 3H).

B. Preparation of a Compound of Formula I in which $R^1$, $R^2$, $R^3$, $R^4$, and $R^5$ are hydrogen, $R^7$ is $CH_3$, n is 1, and $R^a$ is —$CF_3$ using alternative Step 2

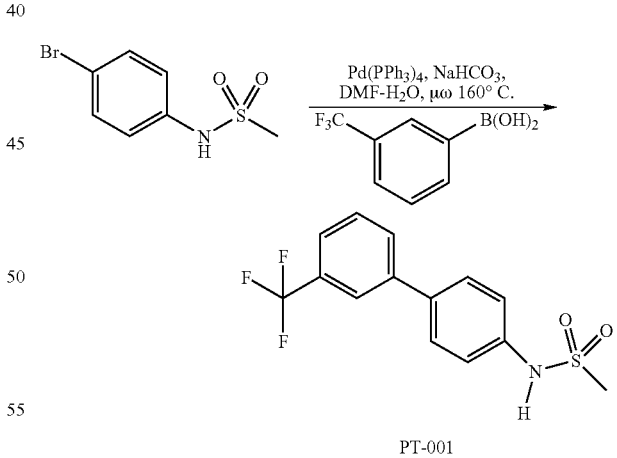

PT-001

To a solution of N-(4-bromophenyl)methanesulfonamide (250 mg, 1.00 mmol) and 3-(trifluoromethyl)phenylboronic acid (285 mg, 1.50 mmol) in DMF (2.5 mL) was added $NaHCO_3$ (252 mg, 3.00 mmol) and $H_2O$ (0.5 mL). The reaction mixture was stirred for 5 min under an atmosphere of dry $N_2$. $Pd(PPh_3)_4$ (59 mg, 0.05 mmol) was added, and the mixture was subjected to a Personal Chemistry microwave irradiation at 160° C. for 25 min. The resulting mixture was cooled, diluted with EtOAc (20 mL), filtered through a layer of celite, washed with 10% DMF in EtOAc (60 mL), transferred to a separation funnel, organic phase was washed with H₂O (30 mL), 30% aqueous NH₄Cl (30 mL), and brine (40 mL), and dried to give gel-like solid. To the crude product was added MeOH (2 mL), sonicated, filtered, washed with MeOH (3 mL), dried to afford white solid. The filtrate was concentrated, subjected to preparative HPLC with a gradient MeCN/H₂O (20% to 98%) to afford the compound designated PT-001.

MS mz 338.0 (M+Na), 379.0 (M+64).

$^1$H NMR (400 MHz; CDCl₃) δ7.79 (s, 1H); 7.43 (d, J=7.4 Hz, 1H); 7.52-7.64 (m, 4H); 7.32 (m, 2H); 6.42 (s, 1H); 3.07 (s, 3H).

C. Preparation of a Compound of Formula I in which $R^1$, $R^2$, $R^3$, and $R^4$ are Hydrogen, $R^5$ and $R^7$ are CH₃, n is 1, and $R^a$ is Phenoxy Using Alternative Step 2

140° C. for 20 min. After the reaction was completed, the mixture was filtered through celite, eluted with EtOAc (40 mL). The organic phase was washed with H₂O (30 mL), 30% NH₄Cl (30 mL), brine (40 mL), and concentrated. To the crude product was added anhydrous ethyl ether (8 mL), sonicated, filtered, washed with diethyl ether (10 mL), dried to give compound 104 (designated PT-046).

MS mz 376.0 (M+Na), anal HPLC >98% in purity.

$^1$H NMR (400 MHz; CDCl₃) δ7.32-7.42 (m, 2H); 7.20-7.30 (m, 4H); 7.00-7.18 (m, 6H); 6.28 (s, 1H); 3.06 (s, 3H); 2.89 (s, 3H).

D. Preparation of Compounds of Formula (IA)

Similarly, by following essentially the procedure of Examples 2A, 2B, or 2C above, but optionally substituting other bromoaniline compounds for 4-bromo-3-chloroaniline, optionally substituting other phenylboronic acids for 4-chloro-3-fluorophenylboronic acid, and optionally substituting other sulfonyl chlorides for the methanesulfonyl chloride, the following compounds of Formula (IA) were prepared.

TABLE 2

| (PT-nnn) | Name of compound |
|---|---|
| PT-001 | N-[3'-(trifluoromethyl)biphenyl-4-yl]methanesulfonamide |
| PT-002 | N-(3',4'-difluorobiphenyl-4-yl)methanesulfonamide |
| PT-030 | N-(3,3'-dichloro-4'-fluorobiphenyl-4-yl)methanesulfonamide |
| PT-039 | N-(3'-chloro-4'-fluoro-2-methylbiphenyl-4-yl)methanesulfonamide |
| PT-040 | N-[2-methyl-3'-(trifluoromethoxy)biphenyl-4-yl]methanesulfonamide |
| PT-056 | N-(4'-fluoro-2-methylbiphenyl-4-yl)methanesulfonamide |
| PT-057 | N-(3',4'-difluoro-2-methylbiphenyl-4-yl)methanesulfonamide |
| PT-098 | N-(2',3-dichloro-4'-fluorobiphenyl-4-yl)methanesulfonamide |
| PT-033 | N-(4'-phenoxybiphenyl-4-yl)methanesulfonamide |
| PT-034 | N-(3-chloro-4'-phenoxybiphenyl-4-yl)methanesulfonamide |
| PT-041 | N-(2-chloro-5-methyl-4'-phenoxybiphenyl-4-yl)methanesulfonamide |
| PT-042 | N-(3-methyl-4'-phenoxybiphenyl-4-yl)methanesulfonamide |
| PT-046 | N-(2-methyl-4'-phenoxybiphenyl-4-yl)methanesulfonamide |
| PT-118 | methyl 4-[(methylsulfonyl)amino]-4'-phenoxybiphenyl-3-carboxylate |
| PT-119 | N-[4'-phenoxy-3-(trifluoromethoxy)biphenyl-4-yl]methanesulfonamide |
| PT-120 | 4-[(methylsulfonyl)amino]-4'-phenoxybiphenyl-3-carboxylic acid |

E. Preparation of Compounds of Formula (IA) and IB

Similarly, by following essentially the procedure of Examples 2A, 2B, or 2C above, but optionally substituting other bromoaniline compounds for 4-bromo-3-chloroaniline, optionally substituting other phenylboronic acids for 4-chloro-3-fluorophenylboronic acid, and optionally substituting other sulfonyl chlorides for the methanesulfonyl chloride, other compounds of Formula (IA) or (IB) may be prepared.

Example 3

Preparation of Compounds of Formula (Ia)

A. Preparation of Compound of Formula I in which $R^1$, $R^2$, $R^3$, and $R^4$ are hydrogen, $R^5$ is hydrogen or Cl, $R^7$ is Cyclopropyl, n is 1, and $R^a$ is —OCF₃

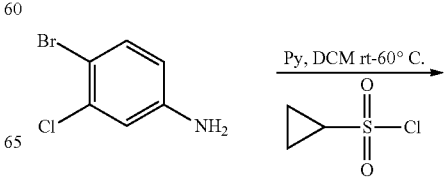

To a solution of 102 (264 mg, 1.00 mmol) and 4-phenoxyphenylboronic acid (257 mg, 1.20 mmol) in DMF (2.5 mL) was added NaHCO₃ (252 mg, 3.00 mmol) and H₂O (0.5 mL). The reaction mixture was stirred for 5 min under an atmosphere of dry N₂. Pd(PPh₃)₄ (59 mg, 0.05 mmol) was added, and the resulting mixture was irradiated with microwave at

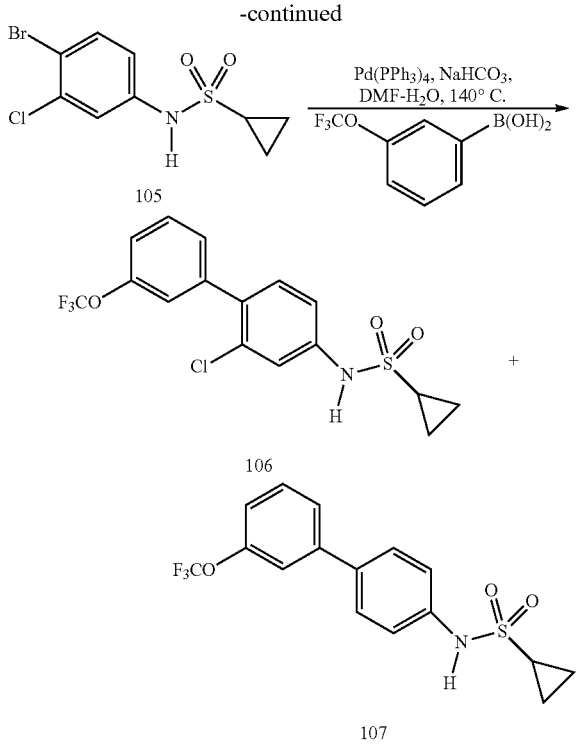

Step 1. Preparation of N-(4-bromo-3-chlorophenyl)cyclopropanesulfonamide, a compound of formula (2)

To a stirred solution of 4-bromo-3-chloroaniline (5.245 g, 25.4 mmol) in $CH_2Cl_2$ (30 mL) was added pyridine (3.2 mL, 39.1 mmol), followed by cyclopropanesulfonyl chloride (5.00 g, 35.6 mmol). The resulting mixture was stirred at room temperature for 30 min, and then heated at 60° C. for 60 h. The reaction mixture was concentrated in vacuo, dissolved in a mixture of EtOAc (100 mL) and $H_2O$ (15 mL), the organic phase was washed with $H_2O$ (50 mL), 0.5N HCl (60 mL), brine (60 mL), dried and concentrated to afford 105. Without further purification, compound 105 was used in the next step.

LCMS mz 307.8 (M−H), 309.8 (M+H).

$^1$H NMR (400 MHz; $CDCl_3$) δ7.56 (d, J=8.6 Hz, 1H); 7.38 (d, J=2.7 Hz, 1H); 7.04 (dd, J=8.6 and 2.7 Hz, 1H); 6.48 (s, 1H); 2.45 (m, 1H); 1.21 (m, 2H); 1.05 (m, 2H).

Step 2. Preparation of N-(2-chloro-3'-(trifluoromethoxy)biphenyl-4-cyclopropanesulfonamide, a Compound of Formula IA To a solution of 105 (311 mg, 1.00 mmol) and 3-(trifluoromethoxy)phenylboronic acid (248 mg, 1.20 mmol) in DMF (2.5 mL) was added $NaHCO_3$ (252 mg, 3.00 mmol) and $H_2O$ (0.5 mL). The reaction mixture was stirred for 5 min under an atmosphere of dry N2. $Pd(PPh_3)_4$ (59 mg, 0.05 mmol) was added, and the resulting mixture was irradiated with microwave at 140° C. for 25 min. The reaction mixture was cooled, diluted with EtOAc (10 mL), filtered through celite, eluted with 10% DMF in EtOAc (90 mL). The organic phase was washed with $H_2O$ (50 mL), 30% $NH_4Cl$ (50 mL) and brine (50 mL), dried over $Na_2SO_4$, and concentrated. The crude product was purified by preparative HPLC with a gradient $MeCN/H_2O$ (5-98%) to give 106 (designated PT-047).

LCMS mz 392.0.1 (M+H).

$^1$HNMR (400 MHz; $CDCl_3$) δ7.46 (t, J=6.8 Hz, 1H); 7.39 (d, J=2.0 Hz, 1H); 7.35 (m, 1H); 7.30 (m, 2H); 7.24 (m, 3H); 6.38 (s, 1H); 2.57 (m, 1H); 1.26 (m, 2H); 1.05 (m, 2H).

Preparative HPLC also afforded compound 107 (designated PT-060)

LCMS mz 358.0.1 (M+H), $^1$HNMR (400 MHz; $CDCl_3$) δ7.54 (m, 2H); 7.42-7.52 (m, 2H); 7.40 (s, 1H); 7.35 (m, 2H); 7.20 (m, 1H); 6.50 (s, 1H); 2.57 (m, 1H); 1.26 (m, 2H); 1.05 (m, 2H).

B. Preparation of Compounds of Formula IA

Similarly, by following essentially the procedure of Examples 3A above, but optionally substituting other bromoaniline compounds for 4-bromo-3-chloroaniline, optionally substituting other phenylboronic acids for 4-chloro-3-fluorophenylboronic acid, and optionally substituting other sulfonyl chlorides for the methanesulfonyl chloride, the following compounds of Formula (IA) were prepared.

TABLE 3

| (PT-nnn) | Name of compound |
| --- | --- |
| PT-047 | N-[2-chloro-3'-(trifluoromethoxy)biphenyl-4-yl]cyclopropanesulfonamide |
| PT-048 | N-(2-chloro-4'-phenoxybiphenyl-4-yl)cyclopropanesulfonamide |
| PT-049 | N-(2,3'-dichloro-4'-fluorobiphenyl-4-yl)cyclopropanesulfonamide |
| PT-050 | N-[2-chloro-4'-(trifluoromethoxy)biphenyl-4-yl]cyclopropanesulfonamide |
| PT-060 | N-[3'-(trifluoromethoxy)biphenyl-4-yl]cyclopropanesulfonamide |
| PT-072 | N-(4'-phenoxybiphenyl-4-yl)cyclopropanesulfonamide |
| PT-074 | N-[4'-chloro-3'-fluoro-3-(trifluoromethoxy)biphenyl-4-yl]methanesulfonamide |
| PT-075 | N-[3-(trifluoromethoxy)-4'-(trifluoromethyl)biphenyl-4-yl]methanesulfonamide |
| PT-076 | N-[3-(trifluoromethoxy)-3'-(trifluoromethyl)biphenyl-4-yl]methanesulfonamide |
| PT-099 | N-[3,4'-bis(trifluoromethoxy)biphenyl-4-yl]methanesulfonamide |
| PT-100 | N-[3,3'-bis(trifluoromethoxy)biphenyl-4-yl]methanesulfonamide |
| PT-114 | N-[4'-phenoxy-3-(trifluoromethoxy)biphenyl-4-yl]cyclopropanesulfonamide |
| PT-115 | N-(3-cyano-4'-phenoxybiphenyl-4-yl)cyclopropanesulfonamide |
| PT-116 | methyl 4-[(cyclopropylsulfonyl)amino]-4'-phenoxybiphenyl-3-carboxylate |
| PT-117 | 4-[(cyclopropylsulfonyl)amino]-4'-phenoxybiphenyl-3-carboxylic acid |
| PT-121 | methyl 4-[(methylsulfonyl)amino]-4'-(trifluoromethyl)biphenyl-3-carboxylate |
| PT-122 | 4-[(methylsulfonyl)amino]-4'-(trifluoromethyl)biphenyl-3-carboxylic acid |

C. Preparation of Compounds of Formula (IA) or (IB)

Similarly, by following essentially the procedure of Example 7A above, but optionally substituting other bromoaniline compounds for 4-bromo-3-chloroaniline, optionally substituting other sulfonyl chlorides for cyclopropanesulfonyl chloride, and optionally substituting other phenylboronic acids for 3-(trifluoromethoxy)phenylboronic acid, other compounds of Formula (I) are prepared.

Example 4

Preparation of a Compound of Formula (Ia)

A. Preparation of a Compound of Formula I in which $R^1$ is $CH_2CN$, $R^2$, $R^3$, and $R^4$ are hydrogen, $R^5$ is Cl, $R^7$ is $CH_3$, n is 2, and $R^a$ are Cl and F

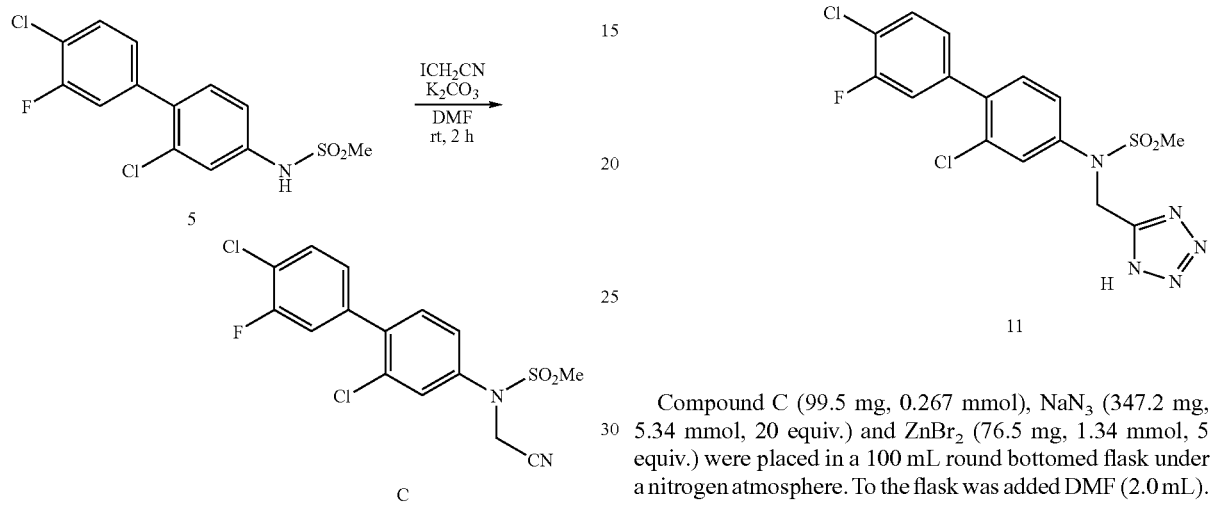

Compound 5 (93.1 mg, 0.279 mmol) and $K_2CO_3$ (77.1 mg, 0.558 mmol, 2.0 equiv.) were placed in a 100 mL round bottomed flask under a nitrogen atmosphere. To the flask was added a solution of iodoacetonitrile (93.2 mg, 0.558 mmol, 2.0 equiv.) in $CH_3CN$ (2.0 mL). The mixture was stirred at room temperature for 2 hours. To the mixture was added $H_2O$ (30 mL) and the reaction mixture was extracted with EtOAc (30 mL×3). Combined organic layers were washed with brine (30 mL) and dried with $Na_2SO_4$. The solvent was removed in vacuo to give a crude mixture (brown oil, 162.1 mg). The crude mixture was purified by a silica gel column chromatography ($SiO_2$=80 g, EtOAc/hexane=1:1, Rf=0.5) to give the desired product C as colorless crystals.

TLC: Rf=0.5 ($SiO_2$, EtOAc/hexane=1:1).

B. Preparation of Compounds of Formula

Similarly, following the procedure of Example 4A above, but optionally substituting other compounds of Formula (IA) or (IB), prepared as described in Examples 1 to 3 above or other halogenated $R^1$ reactants (e.g. bromoacetonitrile, bromobenzonitrile, iodobenzonitrile), other compounds of Formula (IA) may be prepared:

Example 5

Preparation of a Compound of Formula (Ia)

A. Preparation of a Compound of Formula I in which $R^1$ is $CH_2$-Tetrazolyl, $R^2$, $R^3$, and $R^4$ are Hydrogen, $R^5$ is Cl, $R^7$ is $CH_3$, n is 2, and $R^a$ are Cl and F Compound C (99.5 mg, 0.267 mmol), $NaN_3$ (347.2 mg, 5.34 mmol, 20 equiv.) and $ZnBr_2$ (76.5 mg, 1.34 mmol, 5 equiv.) were placed in a 100 mL round bottomed flask under a nitrogen atmosphere. To the flask was added DMF (2.0 mL). The mixture was heated at 110° C. for 17 hours. To the mixture was added $H_2O$ (30 mL) and the reaction mixture was extracted with EtOAc (30 mL×3). Combined organic layers were washed with brine (30 mL) and dried with $Na_2SO_4$. The solvent was removed in vacuo to give a crude mixture (light brown oil, 134.9 mg). The crude mixture was purified by a silica gel column chromatography ($SiO_2$=80 g, using 0-25% MeOH/$CHCl_3$ gradient) to give the desired product, N-(2,4'-dichloro-3'-fluorobiphenyl-4-yl)-N-(2H-tetrazol-5-ylmethyl)methanesulfonamide, as colorless crystals (Compound II, designated. PT-064).

TLC: Rf=0.1 ($SiO_2$, 15% MeOH/$CHCl_3$),

LCMS (EI: 70 eV) 416 ($M^+$).

$^1$H-NMR (400 MHz, DMSO d-6) d 3.12 (3H, s, $SO_2Me$), 5.16 (2H, s, $NCH_2$), 7.20 (1H, dd, J=8.0, 1.6 Hz), 7.30 (1H, dd, J=9.9, 1.6 Hz), 7.34 (1H, d, J=8.0 Hz), 7.39 (1H, dd, J=8.0, 1.6 Hz), 7.52 (1H, t, J==8.0 Hz), 7.54 (1H, d, J=1.6 Hz); LCMS (EI): 438 ($M^+$+Na), 416 (100, $M^+$).

B. Preparation of Compounds of Formula

Similarly, following the procedure of Example 4A above, but optionally substituting other compounds of Formula (IA) or (IB), prepared as described in Example 4 above, other compounds of Formula (IA) may be prepared.

Example 6

Preparation of a Compound of Formula (Ia)

A. Preparation of a Compound of Formula I in which $R^1$ is $CH_2CH_2$-Heterocycle, $R^2$, $R^3$, and $R^4$ are Hydrogen, $R^5$ is Cl, $R^7$ is $CH_3$, n is 2, and $R^a$ are Cl and F

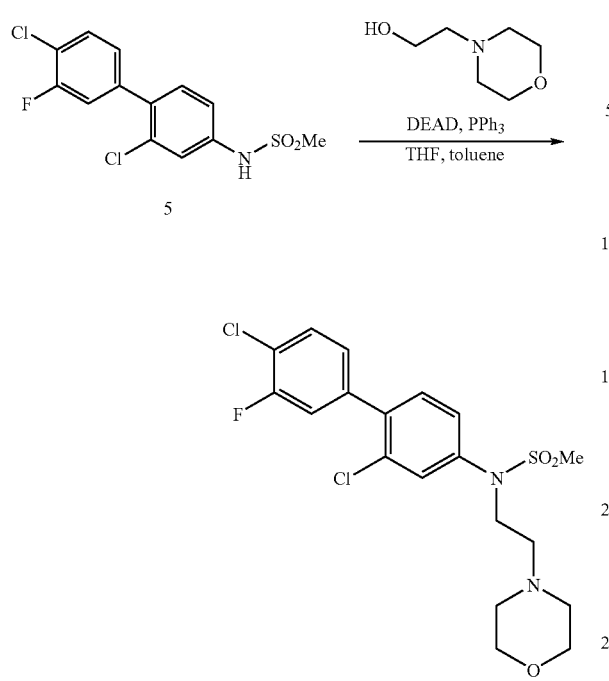

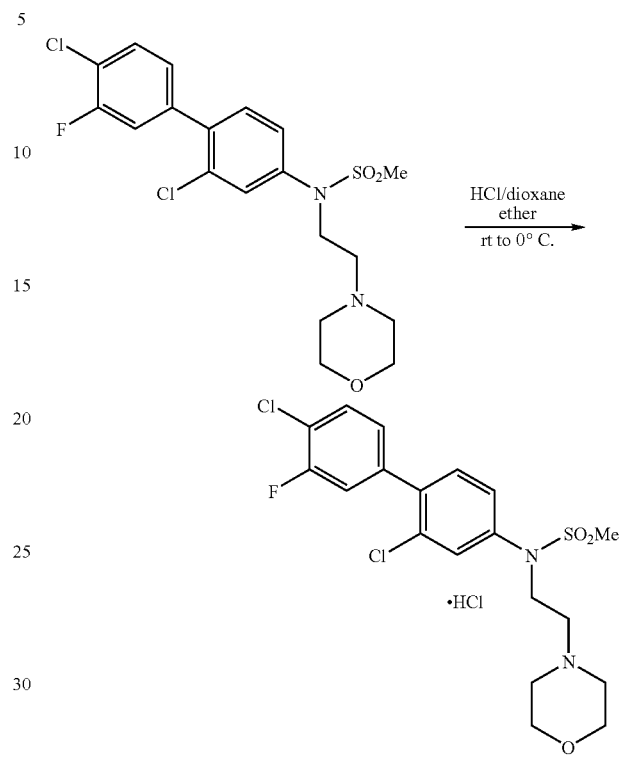

C. Preparation of a HCl Salt of a Compound of Formula I in which $R^1$ is $CH_2CH_2$-Heterocycle, $R^2$, $R^3$, and $R^4$ are hydrogen, $R^5$ is Cl, $R^7$ is $CH_3$, n is 2, and $R^a$ are Cl and F Compound 5 (105.8 mg, 0.317 mmol) and PPh$_3$ (149.8 mg, 0.571 mmol, 1.8 equiv.) were placed in a 50 mL round bottomed flask under a nitrogen atmosphere. To the flask was added a solution of 2-hydroxyethylmorpholine (74.9 mg, 0.571 mmol, 1.8 equiv.) in THF (2 mL) at room temperature. To the mixture was added diethylazodicarboxylate (40% solution in toluene from Aldrich, 0.26 mL, 0.571 mmol, 1.8 equiv.) under ice-water bath cooling. After stirring the mixture at 0° C. for 1 hour, the solvent was removed under reduced pressure to give a crude mixture. The crude mixture was purified by a silica gel column chromatography (SiO$_2$=80 g, using EtOAe/hexane=1:1 to EtOAc to 5% MeOH/EtOAc gradient) to give the desired product, Compound 12 (designated PT-061) as colorless oil.

TLC: Rf=0.05 (SiO$_2$, EtOAc/hexane=1:1)

B. Preparation of Compounds of Formula IA

Similarly, by following essentially the procedure of Examples 6A above, but optionally substituting other hydroxyethyl compounds for 2-hydroxyethylmorpholine, the following compounds of Formula (IA) were prepared.

Compound 12 (140.5 mg, 0.314 mmol) was dissolved in ether (1 mL) in a 100 mL round bottomed flask. To the flask was added 4M-HCl/1,4-dioxane (1.0 mL, 4.0 mmol, 12.7 equiv.) at room temperature. The mixture became a light yellow suspension. After 5 min, ether (6 mL) was added to the suspension. The suspension was cooled with ice-water bath for 20 min with stirring. The suspension was filtered through a glass filter and the desired hydrochloric acid salt was washed with ether (10 mL). The product was collected and dried under a reduced pressure to give the hydrochloric acid salt as a light yellow powder Compound 12 (HCl Salt):

LCMS (EI: 70 eV) 447 (M$^+$-HCl)

D. Preparation of Compounds and Salts of Formula (IA) or (IB)

Similarly, following the procedure of Example 4A above, but optionally substituting other compounds of Formula (IA) or (IB), prepared as described in Example 4 above, other compounds or salts of compounds of Formula (IA) or (IB) may be prepared.

TABLE 4

| (PT-nnn) | Name of compound |
| --- | --- |
| PT-061 | N-(2,4'-dichloro-3'-fluorobiphenyl-4-yl)-N-[2-(morpholin-4-yl)ethyl]methanesulfonamide |
| PT-062 | N-(2,4'-dichloro-3'-fluorobiphenyl-4-yl)-N-[2-(piperidin-1-yl)ethyl]methanesulfonamide |
| PT-063 | N-(2,4'-dichloro-3'-fluorobiphenyl-4-yl)-N-[2-(4-methylpiperazin-1-yl)ethyl]methanesulfonamide |
| PT-077 | N-(2,4'-dichloro-3'-fluorobiphenyl-4-yl)-N-(2-methoxyethyl)methanesulfonamide |

Example 7

Preparation of a Compound of Formula (Ia)

A. Preparation of a Compound of Formula I in which $R^1$ is $CH_2$-Heteroaryl, $R^2$, $R^3$, and $R^4$ are Hydrogen, $R^5$ is $CH_3$, $R^7$ is $CH_3$, n is 1, and $R^a$ is —$OCF_3$

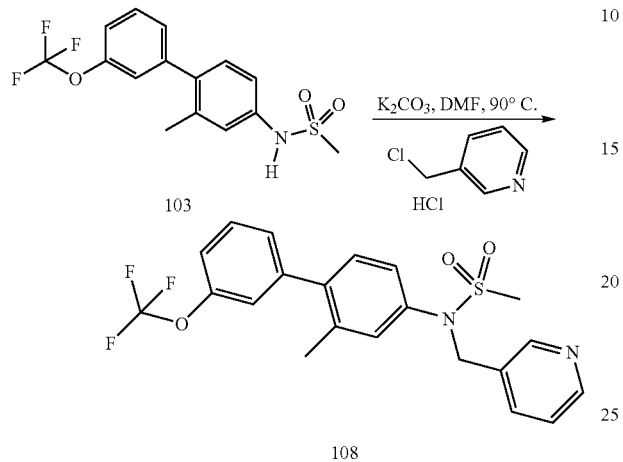

To a solution of 103 (69 mg, 0.20 mmol) in anhydrous DMF (2 ml) was added $K_2CO_3$ (346 mg, 2.5 mmol), stirred at room temperature for 5 min. To the above mixture was added 3-(chloromethyl)pyridine hydrochloride (164 mg, 1.00 mmol), then heated at 90° C. until majority of 103 was converted. The reaction was cooled, poured into $H_2O$ (20 mL), extracted with EtOAc (3×40 mL), combine dorganic phase washed with $H_2O$ (20 mL), 2N $Na_2CO_3$ (10 mL), brine (40 mL), dried over $Na_2SO_4$, and concentrated. To the crude product was added $Et_2O$ (5 mL), sonicated, filtered, washed with $Et_2O$ (20 mL), the combined filtrate was concentrated, subjected to reverse phase HPLC with a gradient of MeCN/$H_2O$ (2% to 98%) to afford 108 (designated PT-073).

LCMS mz 437.0 (M+H), 459.0 (M+Na), $^1$H NMR (400 MHz; $CDCl_3$) δ8.52 (dd, J=4.9 and 1.8 Hz, 1H); 8.45 (d, J=1.8 Hz, 1H); 7.78 (m, 1H); 7.43 (t, J=8.0 Hz, 1H); 7.28 (m, 1H); 7.16-7.24 (m, 4H); 7.00-7.16 (m, 2H); 4.90 (s, 2H); 3.02 (s, 3H); 2.20 (s, 3H).

B. Preparation of Compounds of Formula IA

Similarly, by following essentially the procedure of Example 7A above, but optionally replacing 103 with other compounds of Formula (IA) or (IB)) wherein $R_1$ is hydrogen, and optionally substituting other chloromethylheteroaryl or chloromethylaryl compounds for the 3-(chloromethyl)pyridine hydrochloride, other compounds of Formula (IA) were prepared. Example compounds that were prepared are in the following table:

TABLE 5

| (PT-nnn) | Name of compound |
|---|---|
| PT-073 | N-[2-methyl-3'-(trifluoromethoxy)biphenyl-4-yl]-N-(pyridin-3-ylmethyl)methanesulfonamide |
| PT-081 | N-[2-chloro-3'-(trifluoromethoxy)biphenyl-4-yl]-N-(pyridin-3-ylmethyl)cyclopropanesulfonamide |

C. Preparation of Compounds of Formula (IA) or (IB)

Similarly, following the procedure of Example 7A above, optionally replacing 103 with other compounds of Formula (IA) or (IB)) wherein $R_1$ is hydrogen, and optionally substituting other chloromethylheteroaryl or chloromethylaryl compounds for the 3-(chloromethyl)pyridine hydrochloride, other compounds of Formula (IA) or (IB) may be prepared.

Example 8

Preparation of a Compound of Formula (IA)

A. Preparation of a Compound of Formula I in which $R^1$ is $CH_2COOH$, $R^2$, $R^3$, and $R^4$ are Hydrogen, $R^5$ is $CH_3$, $R^7$ is $CH_3$, n is 1, and $R^a$ is 4-Phenoxy

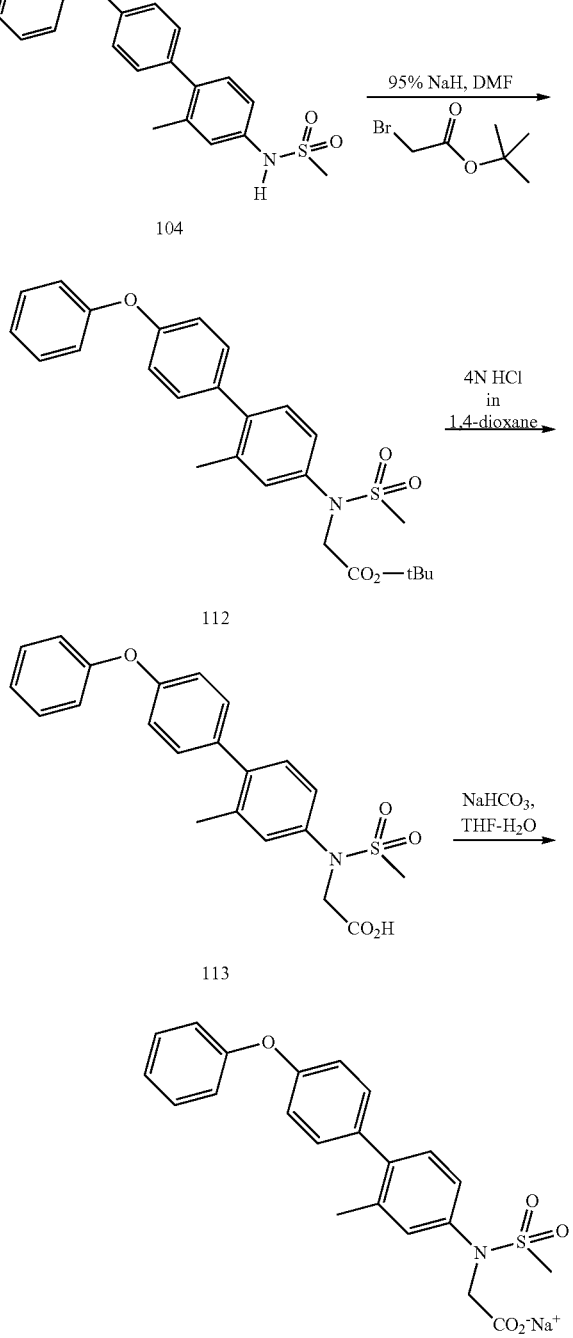

To a mixture of 95% dry NaH (12 mg, 0.48 mmol) in anhydrous DMF (4 mL) at room temperature was added a solution of 104 (PT-046) (106 mg, 0.30 mmol) in anhydrous DMF (1 mL). The reaction mixture was stirred for 30 min under an atmosphere of dry $N_2$, followed by addition of a solution of tert-butyl bromoacetate (0.45 mL, 2.98 mmol) in DMF (1.0 mL). The reaction mixture was stirred at room temperature until majority of 104 was converted (checked by LCMS), then it was quenched by MeOH (5 mL). The reaction mixture was concentrated under a reduced pressure, anhydrous toluene (10 mL) was added, concentrated again in vacuo. To this crude product 112 (designated PT-125) was added 4N HCl in 1,4-dioxane (10 mL, 40 mmol). The reaction mixture was stirred at room temperature for 4 h, and concentrated in vacuo. A second portion of 4N HCl in 1,4-dioxane (10 mL, 40 mmol) and anhydrous DMF (2 mL) were added with stir for another 13 h, and concentrated again in vacuo. The crude reaction product was subjected to reverse phase HPLC with a gradient of $MeCN/H_2O$ (2% to 98%) to afford 113 (designated PT-082).

LCMS mz 433.9 (M+Na),
$^1$H NMR (400 MHz; $CDCl_3$) δ7.32-7.40 (m, 4H); 7.22-7.27 (m, 2H); 7.14 (m, 1H); 7.02-7.10 (m, 4H); 4.56 (s, 2H); 3.15 (s, 3H), 2.29 (s, 3H).

B. Preparation of a HCl Salt of a Compound of Formula I in which $R^1$ is $CH_2COOH$, $R^2$, $R^3$, and $R^4$ are Hydrogen, $R^5$ is $CH_3$, $R^7$ is $CH_3$, n is 1, and $R^a$ is 4-Phenoxy To a solution of 113 (80.0 mg, 0.194 mmol) in THF (1 mL) was added $NaHCO_3$ (16.3 mg, 0.194 mmol) and $H_2O$ (2 mL). The reaction mixture was stirred at room temperature for 1 h, then dried in freeze dryer to give water-soluble powder as the sodium salt of 113.

C. Preparation of Further Compounds of Formula (IA)

Similarly, by following essentially the procedures of Examples 8A above, but replacing 104 (PT-046) with another compound of Formula (IA) wherein $R^1$ is $CH_2COOH$, $R^2$, $R^3$, and $R^4$ are hydrogen, $R^5$ is $CH_3$, $R^7$ is $CH_3$, n is 1, and $R^a$ is 4-Phenoxy —$OCF_3$, the following compound of Formula (I), designated PT-029, was prepared.

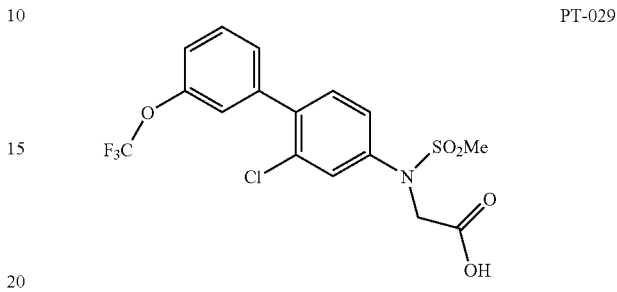

PT-029

$^1$H-NMR ($CD_3OD$) δ 3.14 (s, 3H), 4.52 (s, 2H), 7.31-7.36 (m, 2H), 7.43-7.45 (m, 2H), 7.54-7.58 (m, 2H), 7.73 (d, 1H, J=4.00 Hz)

D. Preparation of Further Compounds of Formula (IA)

Similarly, by following essentially the procedures of Examples 8A, and 8B above, but optionally replacing 104 (PT-046) with other compounds of Formula (I) wherein $R_1$ is hydrogen, and optionally substituting other alkylcarboxyester compounds having a bromo functional group for tert-butyl bromoacetate in Example 8A, the following compounds of Formula (I) were prepared.

TABLE 6

| (PT-nnn) | Name of compound |
|---|---|
| PT-019 | ethyl N-(4'-chloro-3'-fluoro-2-methoxybiphenyl-4-yl)-N-(methylsulfonyl)glycinate |
| PT-020 | ethyl N-[2-methoxy-3'-(trifluoromethoxy)biphenyl-4-yl]-N-(methylsulfonyl)glycinate |
| PT-025 | ethyl N-(2,4'-dichloro-3'-fluorobiphenyl-4-yl)-N-(methylsulfonyl)glycinate |
| PT-028 | ethyl N-[2-chloro-3'-(trifluoromethoxy)biphenyl-4-yl]-N-(methylsulfonyl)glycinate |
| PT-029 | N-[2-chloro-3'-(trifluoromethoxy)biphenyl-4-yl]-N-(methylsulfonyl)glycine |
| PT-082 | N-(2-methyl-4'-phenoxybiphenyl-4-yl)-N-(methylsulfonyl)glycine |
| PT-089 | N-[2-methoxy-3'-(trifluoromethoxy)biphenyl-4-yl]-N-(methylsulfonyl)glycine |
| PT-092 | N-(2,4'-dichloro-3'-fluorobiphenyl-4-yl)-N-(methylsulfonyl)glycine |
| PT-101 | tert-butyl N-[2-fluoro-3'-(trifluoromethoxy)biphenyl-4-yl]-N-(methylsulfonyl)glycinate |
| PT-102 | tert-butyl N-(2,3'-dichloro-4'-fluorobiphenyl-4-yl)-N-(methylsulfonyl)glycinate |
| PT-103 | N-[2-fluoro-3'-(trifluoromethoxy)biphenyl-4-yl]-N-(methylsulfonyl)glycine |
| PT-104 | N-(2,3'-dichloro-4'-fluorobiphenyl-4-yl)-N-(methylsulfonyl)glycine |
| PT-106 | N-(2-chloro-5-methyl-4'-phenoxybiphenyl-4-yl)-N-(methylsulfonyl)glycine |
| PT-111 | N-[2-chloro-4'-(trifluoromethyl)biphenyl-4-yl]-N-(methylsulfonyl)glycine |
| PT-125 | tert-butyl N-(2-methyl-4'-phenoxybiphenyl-4-yl)-N-(methylsulfonyl)glycinate |

E. Preparation of Further Compounds of Formula (IA) and (IB)

Similarly, by following essentially the procedures of Examples 8A, and 8B above, but optionally replacing 104 (PT-046) with other compounds of Formula (I) wherein $R_1$ is hydrogen, and optionally substituting other alkylcarboxyester compounds having a bromo functional group for tert-butyl bromoacetate in Example 8A, other compounds of Formula (IA) and (IB) are prepared.

Example 9

Preparation of a Compound of Formula (Ia)

A. Preparation of a Compound of Formula I in which $R^1$ is $CH_2(CH_3)COOH$, $R^2$, $R^3$, and $R^4$ are Hydrogen, $R^5$ is $CH_3$, $R^7$ is $CH_3$, n is 1, and $R^a$ is 4-Phenoxy Step 1—Addition of the Protected R¹ Moiety

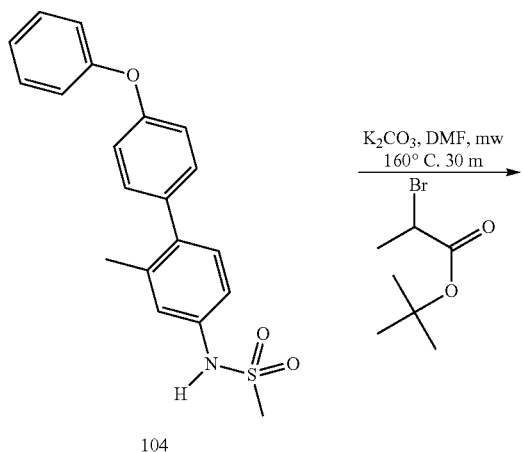

104

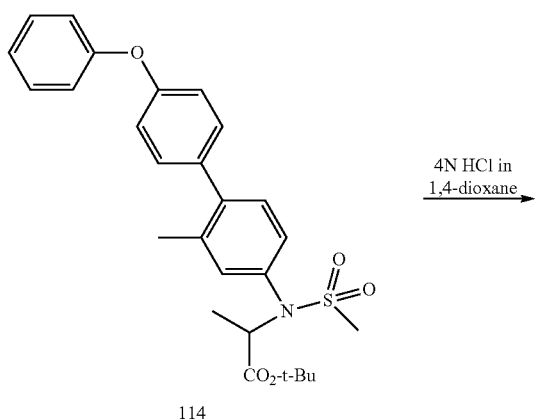

114

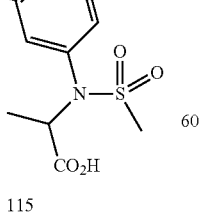

115

To a solution of 104 (PT-046) (71 mg, 0.20 mmol) in anhydrous DMF (2.5 ml) was added $K_2CO_3$ (69 mg, 0.50 mmol), stirred at room temperature for 5 min in a 5 ml Personal Chemistry microwave reaction vial. To the above mixture was added tert-butyl 2-bromopropanoate (105 mg, 0.50 mmol), sealed, subjected to microwave irradiation at 160° C. for 30 min. The reaction was cooled, diluted with EtOAc (10 mL), filtered, the insoluble solid was washed with EtOAc (10 mL), combined organic phase was concentrated in vacuo. The crude product was dissolved in a mixture of DMF-MeOH (1 and 2 mL respectively), subjected to reverse phase HPLC with a gradient of $MeCN/H_2O$ (2% to 98%) to afford 114.

LCMS mz 505.2 (M+Na), $^1$H NMR (400 MHz; $CDCl_3$) δ7.32-7.40 (m, 4H); 7.20-7.30 (m, 3H); 7.13 (m, 1H); 7.02-7.10 (m, 4H); 4.94 (q, J=7.4 Hz, 1H); 3.12 (S, 3H); 2.28 (S, 3H); 1.52 (s, 9H); 1.30 (d, J=7.4 Hz, 3H).

Step 2—Deprotection

To a solution of 114 (48 mg, 0.10 mmol) in anhydrous DMF (1 mL) was added 4N HCl in 1,4-dioxane (10 mL, 40 mmol). The reaction mixture was stirred at room temperature for 4 h, and concentrated in vacuo. A second portion of 4N HCl in 1,4-dioxane (10 mL, 40 mmol) and anhydrous DMF (1 mL) were added with stir for another 13 h, and concentrated again in vacuo, and further freeze dried to afford N-(2-methyl-4'-phenoxybiphenyl-4-yl)-N-(methylsulfonyl)alanine, 115 (designated PT-105) (41 mg, 0.096 mmol, 96%).

LCMS mz 448.0 (M+Na), $^1$H NMR (400 MHz; $CDCl_3$) δ7.53 (d, J=8.2 Hz, 2H); 7.44 (t, J=8.2 Hz, 2H); 7.38 (d, J=8.6 Hz, 2H); 7.19 (t, J=8.2 Hz, 2H); 7.11 (d, J=7.8 Hz, 2H); 7.05 (d, J=8.2 Hz, 2H); 4.43 (q, J=7.4 Hz, 1H); 3.21 (S, 3H); 2.24 (S, 3H); 1.06 (d, J=7.4 Hz, 3H).

C. Preparation of Further Compounds of Formula (IA) and (IB)

Similarly, by following essentially the procedures of Examples 9A, and 9B above, but optionally replacing 104 (PT-046) with other compounds of Formula (IA) or (IB) wherein $R_1$ is hydrogen, and optionally substituting other alkylcarboxyester compounds having a bromo functional group for tert-butyl bromoacetate in Example 9A, other compounds of Formula (IA) and (IB) are prepared.

Example 10

Preparation of a Compound of Formula (Ia)

A. Preparation of a Compound of Formula I in which R¹ is COOH-Phenoxy, $R^2$, $R^3$, and $R^4$ are hydrogen, $R^5$ is $CH_3$, $R^7$ is $CH_3$, n is 1, and $R^a$ is 4-Phenoxy

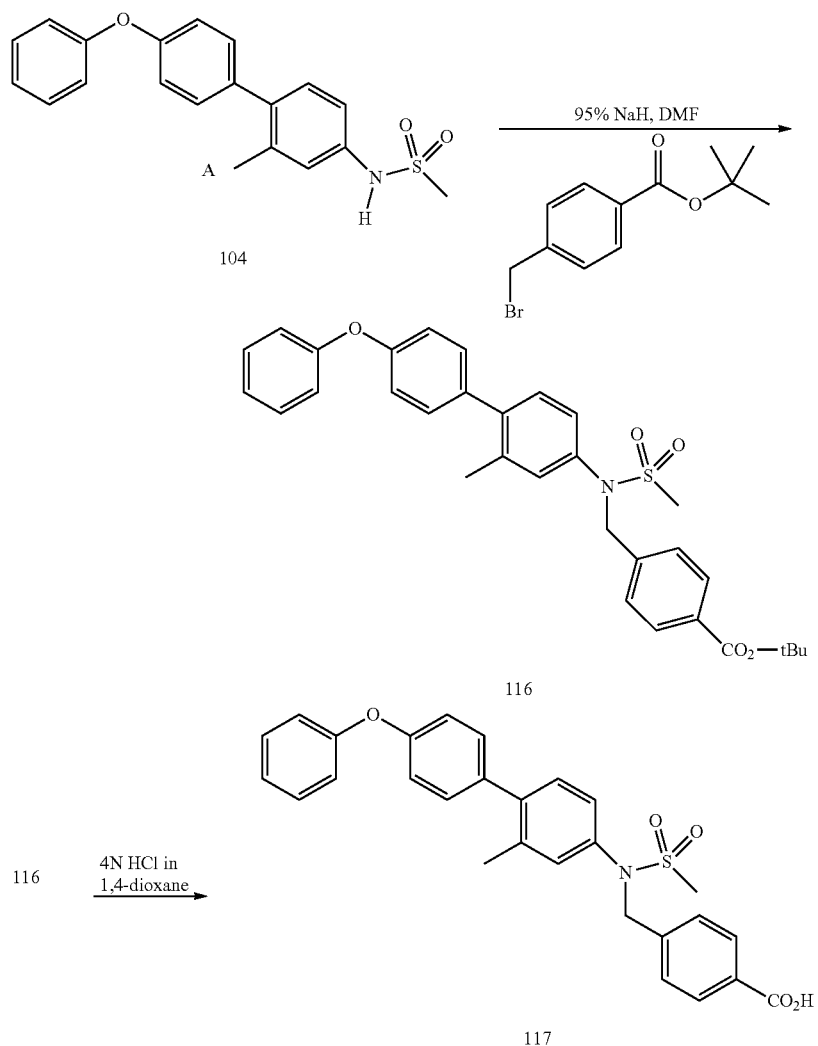

To a mixture of 95% dry NaH (10 mg, 0.40 mmol) in anhydrous DMF (4 mL) at room temperature was added a solution of 104 (71 mg, 0.20 mmol) in anhydrous DMF (1 mL). The reaction mixture was stirred for 30 min under an atmosphere of dry $N_2$, followed by addition of a solution of tort-butyl 4-(bromomethyl)benzoate (271 mg, 1.00 mmol) in DMF (1.0 mL). The reaction mixture was stirred at room temperature until majority of 104 was converted (checked by LCMS), then it was quenched by MeOH (5 mL). The reaction mixture was concentrated at a reduced pressure, anhydrous toluene (10 mL) was added, concentrated again in vacuo. To this crude product 116 (designated PT-107) was added 4N HCl in 1,4-dioxane (10 mL, 40 mmol). The reaction mixture was stirred at room temperature for 4 h, and concentrated in vacuo. A second portion of 4N HCl in 1,4-dioxane (10 mL, 40 mmol) was added with stirring at room temperature for another 13 h, and concentrated again in vacuo. The crude reaction product was subjected to reverse phase HPLC with a gradient of MeCN/$H_2O$ (2% to 98%) to afford 117 (designated PT-108) a compound of Formula (I).

LCMS mz 488.0 (M±H), 510.0 (M+Na), $^1$H NMR (400 MHz; CDCl$_3$) δ8.03 (d, J=8.6 Hz, 2H); 7.45 (d, T=8.6 Hz, 2H); 7.36 (m, 2H); 7.10-7.25 (m, 6H); 7.06 (m, 2H); 7.02 (m, 2H); 4.95 (s, 2H); 3.01 (s, 3H), 2.23 (s, 3H).

B. Preparation of Further Compounds of Formula (IA)

Similarly, by following essentially the procedures of Example 12A above, but optionally replacing 104 (PT-046) with other compounds of Formula (I) wherein $R^1$ is hydrogen, and optionally substituting other arylcarboxyester compounds having a bromoalkyl functional group for tert-butyl 4-(bromomethyl)benzoate in Example 12A, the following compounds of Formula (I) were prepared.

TABLE 7

| (PT-nnn) | Name of compound |
|---|---|
| PT-107 | tert-butyl 4-{[(2-methyl-4'-phenoxybiphenyl-4-yl)(methylsulfonyl)amino]methyl}benzoate |
| PT-108 | 4-{[(2-methyl-4'-phenoxybiphenyl-4-yl)(methylsulfonyl)amino]methyl}benzoic acid |
| PT-112 | 3-{[(2-methyl-4'-phenoxybiphenyl-4-yl)(methylsulfonyl)amino]methyl}benzoic acid |
| PT-113 | 4-{[(2-chloro-5-methyl-4'-phenoxybiphenyl-4-yl)(methylsulfonyl)amino]methyl}benzoic acid |

C. Preparation of Further Compounds of Formula (IA) or (IB)

Similarly, by following essentially the procedures of Example 10A above, but optionally replacing 104 (PT-046) with other compounds of Formula (IA) or (IB) wherein $R^1$ is hydrogen, and substituting other arylcarboxyester compounds having a bromoalkyl functional group for tert-butyl 4-(bromomethyl)benzoate in Example 10A, other compounds of Formula (I) are prepared.

Example 11

Preparation of a Compound of Formula (Ia)

A. Preparation of a Compound of Formula I in which $R^1$ is 2-Hydroxy Cyclopentyl, $R^2$, $R^3$, and $R^4$ are Hydrogen, $R^5$ is $CH_3$, $R^7$ is $CH_3$, n is 1, and $R^a$ is 4-Phenoxy

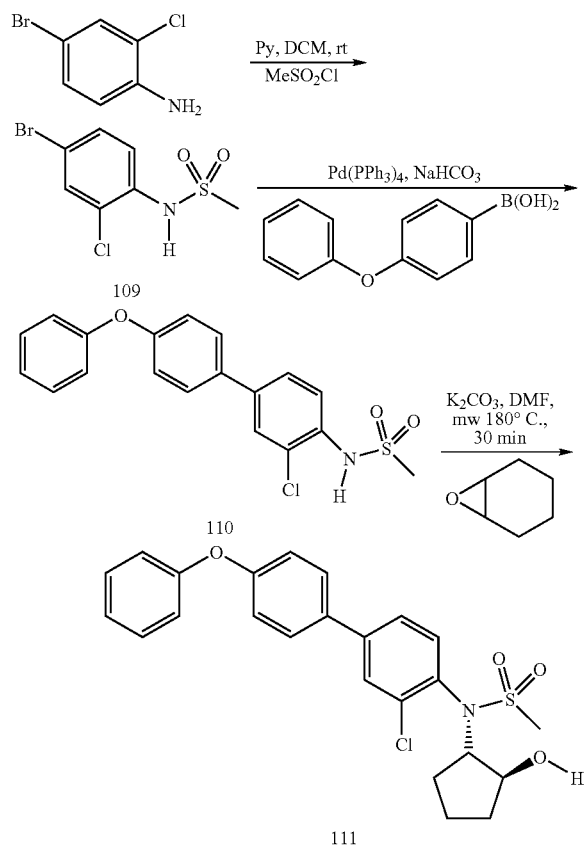

Step 1—Formation of Sulfonamid Moiety

To a stirred solution of 4-bromo-2-chloroaniline 8.260 g, 40.0 mmol) in $CH_2Cl_2$ (40 mL) was added pyridine (4.86 mL, 60.0 mmol), followed by methanesulfonyl chloride (4.65 mL, 60.0 mmol). The resulting mixture was stirred at room temperature for 21 hrs. The reaction solution was concentrated in vacuo, 0.5N aqueous HCl (60 mL) was added, stirred and sonicated, filtered, washed with 0.5N HCl (100 mL), $H_2O$ (100 mL) and n-hexane (80 mL), dried to give 109.

LCMS mz 307.8 (M+Na).

$^1$H NMR (400 MHz; $CDCl_3$) δ7.60 (d, T=2.3 Hz, 1H); 7.55 (d, 9.0 Hz, 1H); 7.44 (dd. J=9.0 and 2.3 Hz, 1H); 6.76 (s, 1H) 3.02 (s, 3H).

Step 2—Coupling of Second Phenyl Ring

To a solution of 109 (285 mg, 1.00 mmol) and 4-phenoxyphenylboronic acid (257 mg, 1.20 mmol) in DMF (5 mL) was added $NaHCO_3$ (252 mg, 3.00 mmol) and $H_2O$ (0.5 mL). The reaction mixture was stirred for 5 min under an atmosphere of dry $N_2$. $Pd(PPh_3)_4$ (59 mg, 0.05 mmol) was added, and the resulting mixture was heated at 86° C. for 30 h. Cooled, diluted with EtOAc (20 mL), filtered through a layer of celite, washed with EtOAc (60 mL), transferred to a separation funnel, organic phase was washed with 2N $K_2CO_3$ (20 mL), 30% $NH_4Cl$ (40 mL) and brine (50 mL), concentrated. The crude product was purified by preparative HPLC with a gradient MeCN in $H_2O$ (5-98%) to give compound 110.

LCMS mz 395.9 (M+Na).

$^1$H NMR (400 MHz; $CDCl_3$) δ7.71 (d, J=8.2 Hz, 1H); 7.62 (d, J=2.3 Hz, 1H); 7.46-7.54 (m, 3H); 7.37 (m, 2H); 7.15 (m, 1H); 7.02-7.10 (m, 4H); 6.77 (s, 1H); 3.05 (s, 3H).

Step 3—Coupling of $R^1$ Moiety

To a solution of 110 (27 mg, 0.07 mmol) in anhydrous DMF (2 ml) was added $K_2CO_3$ (55 mg, 0.4 mmol), stirred at room temperature for 5 min in a 5 ml Personal Chemistry microwave reaction vial. To the above mixture was added 6-oxabicyclo[3.1.0]hexane (336 mg, 4.0 mmol), sealed, subjected to microwave irradiation at 180° C. for 30 min. The reaction was cooled, poured into $H_2O$ (10 mL), extracted with EtOAc (2×30 mL), combined dorganic phase washed with $H_2O$ (30 mL), 2N $Na_2CO_3$ (30 mL), brine (40 mL), dried over $Na_2SO_4$, and concentrated. The crude product was separated using column chromatograph via silica gel eluting with MeOH in $CH_2Cl_2$ (0% to 10%) to afford 111

LCMS mz 479.9 (M+Na), $^1$H NMR (400 MHz; $CDCl_3$) δ8.02 (s, 1H); 7.70 (d, =1.9 Hz, 1H); 6.88 (m, 1H); 7.46-7.56 (m, 4H); 7.35-7.42 (m, 2H); 7.16 (t, J=7.4 Hz, 1H); 7.04-7.12 (m, 4H); 4.00-4.40 (m, 2H); 2.78 (m, 1H); 1.82-2.20 (m, 3H), 1.40-1.80 (m, 2H).

B. Preparation of Further Compounds of Formula (IA) or (IB)

Similarly, by following essentially the procedures of Examples 11A above, but optionally substituting other bromoaniline compounds for 4-bromo-2-chloroaniline and optionally substituting other sulfonyl chlorides for methanesulfonyl chloride in Step 1, optionally substituting other phenylboronic acids for 4-phenoxyphenylboronic acid in Step 2, and optionally substituting other epoxide compounds in Step 3, other compounds of Formula (IA) or (IB) are prepared.

Example 12

Preparation of a Compound of Formula (Ia)

A. Preparation of a Compound of Formula I in which $R^1$, $R^2$, $R^3$, $R^4$, and $R^5$ are Hydrogen, $R^7$ is Cyclopropyl, n is 1, and $R^a$ is 4-Phenoxy

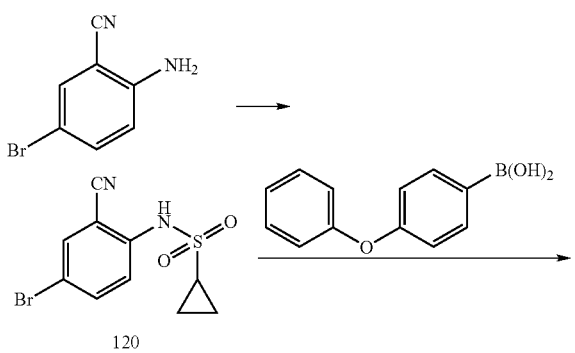

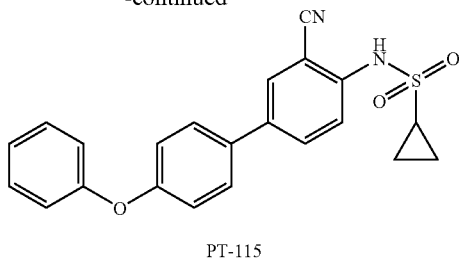

PT-115

Step 1—Formation of the Sulfonamide Moiety

To a stirred solution of 2-amino-5-bromobenzonitrile (1 g, 5.08 mmole) in pyridine (6 mL) at room temperature was added cyclopropylsulfonyl chloride (1.57 g, 11.2 mmol), dropwise. The resulting mixture was stirred at room temperature for 48 hours. Then it was heated at 80° C. for 3 hours. The reaction mixture was concentrated in vacuo and purified by biotage column chromatography eluting with 1:4 ethyl acetate/hexane to afford 120.

Step 2—Coupling of Second Phenyl Ring

To a solution of Compound 120 (230 mg, 0.764 mmol) and 4-phenoxyphenylboronic acid (196 mg, 0.917 mmol) in DME (8 mL) was added Pd(PPh$_3$)$_4$ (0.0382 mg, 0.05 mmol) followed by 2M aqueous Na$_2$CO$_3$ (2 mL). The resulting mixture was heated at 80° C. for 1 hour. The mixture was cooled, diluted with ethyl acetate, and filtered through a plug of celite. The filtrate was concentrate down and purified by preparative TLC eluting with CH$_2$Cl$_2$ to give N-(3-cyano-4'-phenoxybiphenyl-4-yl)cyclopropanesulfonamide, PT-115.

$^1$HNMR (400 MHz; CDCl$_3$) δ 1.09-1.14 (m, 2H); 1.27-1.30 (m, 2H); 2.61-2.65 (m, 1H); 6.86 (s, 1H); 7.09-7.14 (m, 4H); 7.18-7.21 (m, 1H); 7.40-7.44 (m, 2H); 7.51-7.54 (m, 2H); 7.81-7.86 (m, 3H).

B. Preparation of a Compound of Formula I in which R$^1$, R$^2$, R$^3$ and R$^4$ are Hydrogen R$^5$, is CN, R$^7$ is Cyclopropyl, n is 1, and R' is 4-Phenoxy

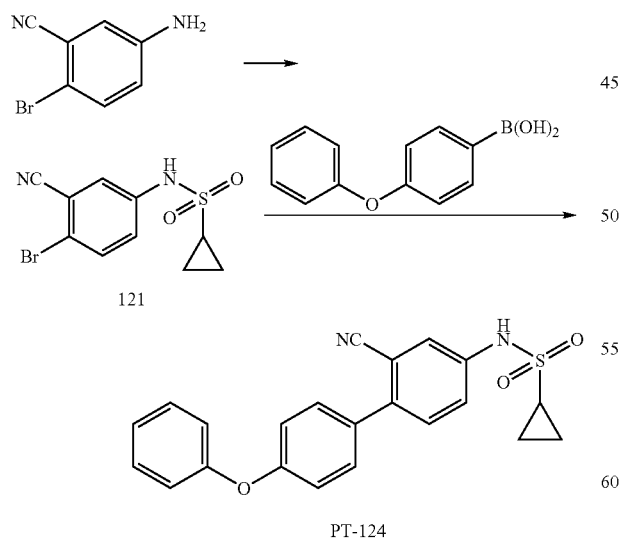

121

PT-124

Step 1—Formation of the Sulfonamide Moiety

To a stirred solution of 5-amino-2-bromobenzonitrile (1 g, 5.08 mmol) in CH$_2$Cl$_2$ (18 L) was added pyridine (1.5 g, 15.2 mmol) followed by dropwise addition of cyclopropylsulfonyl chloride. The resulting mixture was stirred at room temperature for 15 hours. The mixture was diluted with CH$_2$Cl$_2$, washed with NaHCO$_3$ and brine. The organic extract was dried over Na$_2$SO$_4$ and purified by biotage column chromatography eluting with 1:1 ethyl acetate/hexane mixture to give 121.

Step 2—Coupling of Second Phenyl Ring

To a solution of Compound 121 (430 mg, 1.44 mmol) and 4-phenoxyphenylboronic acid (369 mg, 1.73 mmol) in DME (8 mL) was added Pd(PPh$_3$)$_4$ (0.0719 mg, 0.05 mmol) followed by 2M aqueous Na$_2$CO$_3$ (2 mL). The resulting mixture was heated at 80° C. for 1 hour. The mixture was cooled, diluted with ethyl acetate, and filtered through a plug of celite. The filtrate was concentrate down and purified by preparative TLC eluting with 5% MeOH/CH$_2$Cl$_2$ mixture to give N-(2-cyano-4'-phenoxybiphenyl-4-yl)cyclopropanesulfonamide, PT-124.

$^1$HNMR (400 MHz; CDCl$_3$) δ1.05-1.10 (m, 2H): 1.25-1.29 (m, 2H); 2.53-2.60 (m, 1H); 6.49 (s, 1H); 7.09-7.12 (m, 3); 7.16-7.20 (m, 1); 7.38-7.42 (m, 2H); 7.49-7.56 (m, 4H); 7.62-7.63 (m, 2H).

C. Preparation of Further Compounds of Formula (IA) or (IB)

Similarly, by following essentially the procedures of Example 12A above, but optionally substituting other bromoaniline compounds for the bromoaniline compounds used in Examples 12A and 12B, optionally substituting other sulfonyl chlorides for the cyclopropylsulfonyl chloride used in Examples 12A and 12B, and optionally substituting other phenylboronic acids for the 4-phenoxyphenylboronic acid used in Examples 12A and 12B, other compounds of Formula (IA) or (TB) may be prepared.

Example 13

Preparation of a Compound of Formula (IA)

A. Preparation of a Compound of Formula I in which R$^1$, R$^3$, R$^4$ and R$^5$ are hydrogen, R$^2$ is COOCH$_3$, R$^7$ is CH$_3$, n is 1, and R$^a$ is —CF$_3$

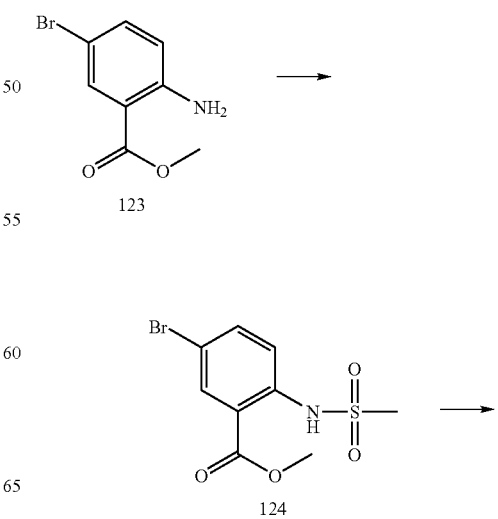

123

124

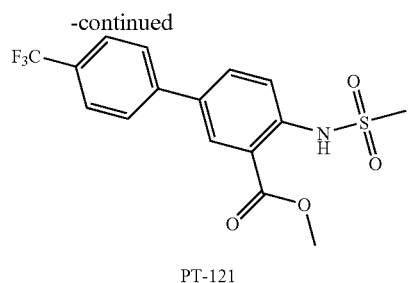

PT-121

Step 1—Formation of the Sulfonamide Moiety

To a solution of the bromoaniline compound 123 (1.0 g, 4.37 mmol) in toluene (20 mL), methanesulfonyl chloride (2.5 g, 22 mmol, 5 eq) was added followed by pyridine (5 mL) and the reaction mixture was heated at 90° C. for 24 h. The reaction mixture was cooled to room temperature, diluted with ethyl acetate (50 mL). The combined organic solvents were washed with water, dil. HCl, water, brine, and dried over sodium sulfate. Solvent was distilled off, and the residue was charged on a silica gel column and eluted with dichloromethane to get the methyl sulfonamide derivative 124.

$^1$HNMR (400 MHz; CDCl$_3$) δ 10.40 (s, 1H); 8.25 (d, J=4.0 Hz, 1H); 7.70 (d, 8 Hz, 1H); 7.62 (dd, J$_1$=8 Hz, J$_2$=4 Hz, 1H), 3.96 (s, 3H); 3.12 (s, 3H)

Step 2—Coupling of Second Phenyl Ring

To a solution of methane sulfonamide (308 mg, 1 mmol) in DMF:H$_2$O (10 mL; 9:1), 4-trifluoromethyl phenylboronic acid (227 mg, 1.2 mmol) was added followed by sodium bicarbonate (252 mg, 3 mmol) and stirred under nitrogen for 5 min. To the reaction mixture Pd(PPh$_3$)$_4$ (55 mg, 0.05 mmol) was added and heated at 90° C. for 90 min. The reaction mixture was cooled, filtered through celite, washed with EtOAc (50 mL). The combined organics were washed with water, brine, dried over Na$_2$SO$_4$ and concentrated. The product (180 mg, 49%) was purified by preparative TLC by eluting with CH$_2$Cl$_2$.to give methyl 4-[(methylsulfonyl)amino]-4'-(trifluoromethyl)biphenyl-3-carboxylate, PT-121.

LCMS mz 395.9 (M+Na),
$^1$HNMR (400 MHz; CDCl$_3$) δ 10.51 (s, 1H); 8.30 (d, J=4.0 Hz, 1H); 7.87 (d, 8 Hz, 1H); 7.80 (dd, J$_1$=8 Hz, J$_2$=4 Hz, 1H), 7.72 (d, J=8 Hz, 2H); 7.68 (d, J=8 Hz, 2 h); 3.99 (s, 3H); 3.12 (s, 3H)

B. Alternate Step 1—Preparation of a Compound of Formula 1 in which R$^1$, R$^2$, R$^3$, and R$^4$ are hydrogen, R$^5$, is CN, R$^7$ is Cyclopropyl

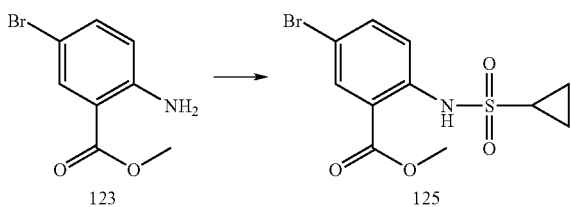 [SMILES: COC(=O)c1cc(Br)ccc1N ; COC(=O)c1cc(Br)ccc1NS(=O)(=O)C1CC1]

To a solution of the bromoaniline compound 123 (1.0 g, 4.37 mmol) in toluene (20 mL), cyclopropanesulfonyl chloride (6 g, 44 mmol, 10 eq) was added followed by pyridine (10 mL) and the reaction mixture was heated at 100° C. for 72 h. The reaction mixture was cooled to room temperature, diluted with ethyl acetate (50 mL). The combined organic solvents were washed with water, dil HCl, water, brine, and dried over sodium sulfate. Solvent was distilled off, and the residue was charged on a silica gel column and eluted with dichloromethane to get the methyl sulfonamide derivative 125.

$^1$HNMR (400 MHz; CDCl$_3$) δ 10.27 (s, 1H); 8.16 (d, J=4.0 Hz, 1H); 7.72 (d, 8 Hz, 1H); 7.63 (dd, J$_1$=8 Hz, J$_2$=4 Hz, 1H), 3.95 (s, 3H); 2.52 (m, 1H); 1.26 (m, 2H); 0.99 (m, 2H)

C. Preparation of Compounds of Formula (I)

Similarly, by essentially following the procedures of Example 13A, Steps 1 and 2 above, but optionally substituting other bromoaniline compounds for compound 123, and optionally substituting other sulfonyl chlorides for the sulfonyl chloride used in the Example 13A, Step 1, or Example 13B and optionally substituting other phenylboronic acids for the 4-trifluoromethyl phenylboronic acid used in the Example 13A, Step 2, other compounds of Formula (IA) or (IB) may be prepared.

For examples, the following compounds of Formula (IA) was prepared, methyl 4-[(methylsulfonyl)amino]-4'-phenoxybiphenyl-3-carboxylate, PT-118.

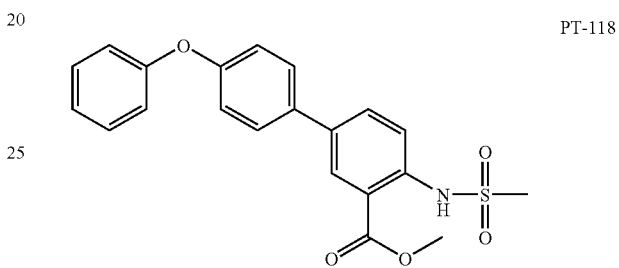

PT-118

LCMS mz 420 (M+Na)
$^1$HNMR (400 MHz; CDCl$_3$) δ 10.41 (s, 1H); 8.26 (d, J=4.0 Hz, 1H); 7.82 (d, 8 Hz, 1H); 7.76 (dd, J$_1$=8 Hz, J$_2$=4 Hz, 1H), 7.53 (d, J=8 Hz, 2H); 7.40-7.34 (m, 2H); 7.09 (d, ±8 Hz, 2H); 7.16-7.04 (m, 3H); 3.97 (s, 3H); 3.09 (s, 3H)

The compound of Formula (I) designated 4-[(cyclopropylsulfonyl)amino]-4'-phenoxybiphenyl-3-carboxylate, PT-116 was also prepared:

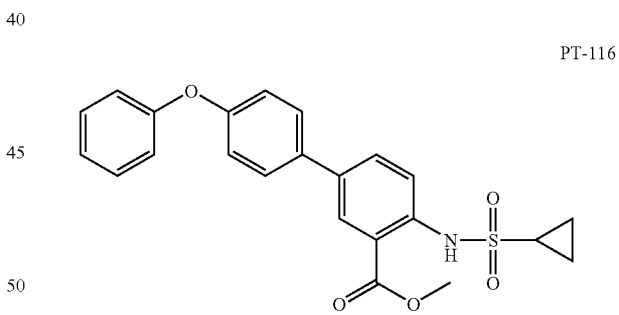

PT-116

LCMS mz 446 (M+Na), anal HPLC 96%,
$^1$HNMR (400 MHz; DMSO-d6) δ 10.09 (s, 1H): 8.23 (s, 1H); 7.96 (d, 8 Hz, 1H); 7.72 (d, J=8 Hz, 1H); 7.71 (d, J=8 Hz, 2H); 7.43 (t, J=8 Hz, 2H); 7.19 (t, J=8 Hz, 1H), 7.11 (d, J=8 Hz, 2H); 7.09 (d, J=8 Hz, 2H); 3.94 (s, 3H); 2.87 (quintent, 1H); 1.02 (d, J=8 Hz, 4H).

Example 14

Preparation of a Compound of Formula (IA) having R$^2$ Acid Groups

A. Preparation of a Compound of Formula I in which R$^1$, R$^3$, R$^4$, and R$^5$ are Hydrogen, R$^2$ is COOH, R$^7$ is Methyl, n is 1, and R$^a$ is —CF$_3$

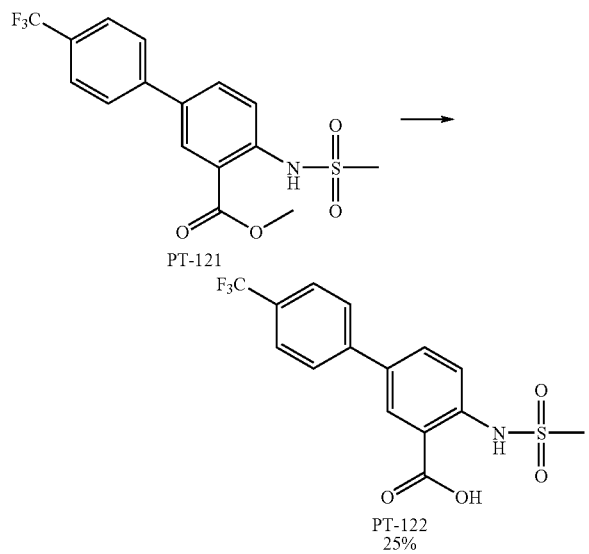

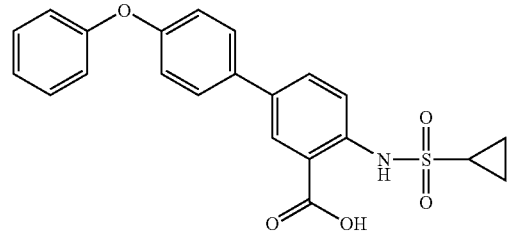

LCMS mz 431.9 (M+Na),

¹HNMR (400 MHz; DMSO-d6) δ 8.22 (d, J=8 Hz, 1H); 7.64 (d, J=8 Hz, 3H); 7.59 (d, J=4 Hz, 1H), 7.56 (d, J=8 Hz, 1H); 7.43 (t, J=8 Hz, 2H); 7.17 (t, J=8 Hz, 1H), 7.09 (d, J=8 Hz, 4H); 2.57 (m, 1H); 0.96-0.84 (m, 4H).

To a suspension of methyl ester PT-121 (50 mg) in methanol (5 mL) and water (1 mL), 50% NaOH solution (1 mL) was added and heated at 90° C. for 3 h. The reaction mixture was diluted with ethyl acetate (50 mL), washed with water, dil. HCl, water, brine, dried over Na₂SO₄ and concentrated. The residue was treated with CH₂Cl₂ and hexane, and the precipitate thus formed was filtered and dried to get the acid derivative 4-[(methylsulfonyl)amino]-4'-(trifluoromethyl)biphenyl-3-carboxylic acid, designated PT-122:

LCMS mz 381.8 (M+Na),

¹HNMR (400 MHz; DMSO-d6) δ 10.83 (s, 1H); 8.33 (d, J=4.0 Hz, 1H); 8.06 (dd, J=8 Hz, J₂=4 Hz, 1H), 7.93 (d, J=8 Hz, 2H); 7.84 (d, J=8 Hz, 2H); 7.74 (d, 8 Hz, 1H); 3.28 (s, 3H).

B. Preparation of Compounds of Formula (IA)

Similarly, by essentially following the procedures of Example 14A above, but substituting other compounds of Formula (I) that are carboxylate esters for compound PT-121, the corresponding carboxylic acids may be prepared. For examples, the following compounds of Formula (I) were prepared.

The compound of Formula (IA) 4-[(methylsulfonyl)amino]-4'-phenoxybiphenyl-3-carboxylic acid, designated PT-120 was prepared:

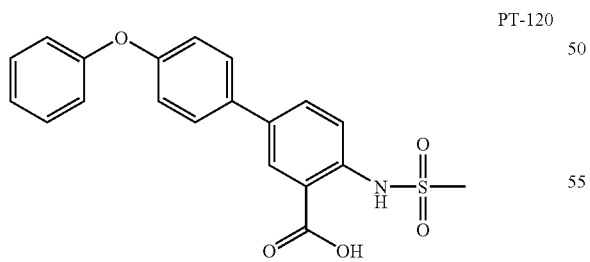

LCMS mz 406 (M+Na),

¹HNMR (400 MHz; DMSO-d6) δ 10.71 (s, 1H); 8.23 (s, 1H); 7.95 (d, J=8 Hz, 1H); 7.70 (d, J=8 Hz, 1H); 7.69 (d, J=8 Hz, 2H), 7.44 (t, J=8 Hz, 2H); 7.19 (t, J=8 Hz, 1H), 7.11 (d, J=8 Hz, 2H); 7.09 (d, J=8 Hz, 2H); 3.24 (s, 3H)

The compound of Formula (I) 4-[(cyclopropylsulfonyl)amino]-4'-phenoxybiphenyl-3-carboxylic acid, designated PT-117 was also prepared:

Example 15

Preparation of a Compound of Formula (IA) having R² Amido Groups

A. Preparation of a Compound of Formula I in which R¹, R³, R⁴, and R⁵ are Hydrogen, R² is COOH, R⁷ is Methyl, n is 1, and Rᵃ is —CF₃

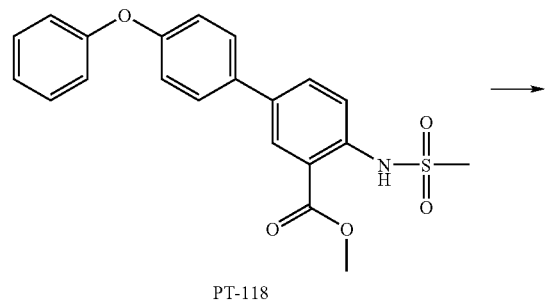

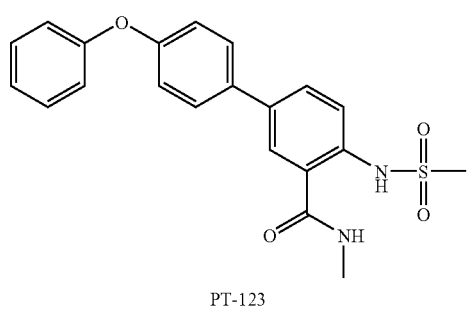

To a solution of the methyl ester PT-118 (70 mg, 0.17 mmol) in ethanol (10 ml), methyl amine (2 mL) was added and heated at 90° C. for 24 h. Ethanol was distilled off, the residue was dissolved in ethyl acetate (50 mL), washed with water, brine, dried over Na₂SO₄ and concentrated. The product was purified by preparative TLC by eluting with 2% MeOH—CH₂Cl₂ to give the amide compound N-methyl-4-

(methylsulfonamido)-4'-phenoxybiphenyl-3-carboxamide, designated PT-123:

LCMS m/z 418.2 (M+Na), $^1$HNMR (400 MHz; DMSO-d6) δ 11.32 (s, 1H); 9.03 (s, 1H); 8.09 (d, J=4 Hz, 1H); 7.85 (dd, $J_1$=8 Hz, $J_2$=4 Hz, 1H); 7.79 (d, J=8 Hz, 2H), 7.64 (d, J=8 Hz, 1H); 7.44 (t, J=8 Hz, 2H), 7.19 (7, J=8 Hz, 1H); 7.14 (d, J=8 Hz, 2H); 7.08 (d, J=8 Hz, 2H); 3.17 (s, 3H); 2.86 (d, J=4 Hz, 3H).

B. Preparation of Compounds of Formula (IA) or (IB)

Similarly, by essentially following the procedures of Example 15A above, but substituting other compounds of Formula (IA) or (IB) that are carboxylate esters for compound PT-118, or optionally substituting other amines for the methylamine, the corresponding amides may be prepared.

Example 15

Preparation of Compounds of Formula (IB)

Similarly, by essentially following the procedure of Examples 1-14 above, but optionally substituting 3-bromoaniline compounds for the 4-bromoaniline compounds used in the Examples, optionally substituting other sulfonyl chlorides for the sulfonyl chlorides used in the Examples, and optionally substituting other phenylboronic acids for the phenylboronic acids used in the Examples, other compounds of Formula (IB) may be prepared. For examples, the following compounds of Formula (IB) were prepared.

TABLE 8

| (PT-nnn) | Name of compound |
| --- | --- |
| PT-109 | N-[6-methoxy-3'-(trifluoromethoxy)biphenyl-3-yl]methanesulfonamide |
| PT-110 | N-(4'-chloro-3'-fluoro-6-methoxybiphenyl-3-yl)methanesulfonamide |
| PT-127 | N-(4'-chlorobiphenyl-3-yl)-3-methoxybenzenesulfonamide |
| PT-131 | 4-(3'-(methylsulfonamido)biphenyl-4-yloxy)benzoic acid |
| PT-132 | N-(3'-fluoro-4'-(trifluoromethyl)biphenyl-3-yl)methanesulfonamide |
| PT-154 | 4-((N-(3'-fluoro-4'-(trifluoromethyl)biphenyl-3-yl)methylsulfonamido)methyl)benzoic acid |
| PT-155 | tert-butyl 4-((N-(3'-fluoro-4'-(trifluoromethyl)biphenyl-3-yl)methylsulfonamido)methyl)benzoate |

Example 16

Preparation of Compounds of Formula (IA) and (IB)

Compounds of Formula (IA) or (IB) may be made by essentially following the procedures set out in Examples 1 through 15 above, but optionally altering the selection of the starting materials to select compounds having the necessary substituents to result in the desired products (e.g. the products in the table below), or using other synthetic methods known in the art. The following compounds were prepared:

TABLE 9

| ID (PT-nnn) | Name of Compound |
| --- | --- |
| PT-001 | N-[3'-(trifluoromethyl)biphenyl-4-yl]methanesulfonamide |
| PT-002 | N-(3',4'-difluorobiphenyl-4-yl)methanesulfonamide |
| PT-003 | N-(4'-chloro-3'-fluoro-2-methoxybiphenyl-4-yl)methanesulfonamide |
| PT-004 | N-[2-methoxy-4'-(trifluoromethyl)biphenyl-4-yl]methanesulfonamide |
| PT-005 | N-(4'-chloro-3'-fluorobiphenyl-4-yl)methanesulfonamide |
| PT-006 | N-[4'-(trifluoromethyl)biphenyl-4-yl]methanesulfonamide |
| PT-007 | N-(3'-chloro-4'-fluorobiphenyl-4-yl)methanesulfonamide |
| PT-008 | N-[3'-(trifluoromethoxy)biphenyl-4-yl]methanesulfonamide |
| PT-009 | N-[2-methoxy-4'-(trifluoromethoxy)biphenyl-4-yl]methanesulfonamide |
| PT-010 | N-[2-methoxy-3'-(trifluoromethoxy)biphenyl-4-yl]methanesulfonamide |
| PT-011 | N-[2-methoxy-2'-(trifluoromethoxy)biphenyl-4-yl]methanesulfonamide |
| PT-012 | N-[4'-chloro-3'-fluoro-2-(trifluoromethyl)biphenyl-4-yl]methanesulfonamide |
| PT-013 | N-[2,4'-bis(trifluoromethyl)biphenyl-4-yl]methanesulfonamide |
| PT-014 | N-[4'-(trifluoromethoxy)-2-(trifluoromethyl)biphenyl-4-yl]methanesulfonamide |
| PT-015 | N-[3'-(trifluoromethoxy)-2-(trifluoromethyl)biphenyl-4-yl]methanesulfonamide |
| PT-016 | N-[2'-(trifluoromethoxy)-2-(trifluoromethyl)biphenyl-4-yl]methanesulfonamide |
| PT-017 | N-(2,4'-dichloro-3'-fluorobiphenyl-4-yl)methanesulfonamide |
| PT-018 | N-[2-chloro-4'-(trifluoromethyl)biphenyl-4-yl]methanesulfonamide |
| PT-019 | ethyl N-(4'-chloro-3'-fluoro-2-methoxybiphenyl-4-yl)-N-(methylsulfonyl)glycinate |
| PT-020 | ethyl N-[2-methoxy-3'-(trifluoromethoxy)biphenyl-4-yl]-N-(methylsulfonyl)glycinate |
| PT-021 | N-[2-chloro-3'-(trifluoromethoxy)biphenyl-4-yl]methanesulfonamide |
| PT-022 | N-[2-chloro-2'-(trifluoromethoxy)biphenyl-4-yl]methanesulfonamide |
| PT-023 | N-(2-chloro-3'-4'-difluorobiphenyl-4-yl)methanesulfonamide |
| PT-024 | N-(2-chloro-2'-4'-difluorobiphenyl-4-yl)methanesulfonamide |
| PT-025 | ethyl N-(2,4'-dichloro-3'-fluorobiphenyl-4-yl)-N-(methylsulfonyl)glycinate |
| PT-026 | N-(2,4'-dichloro-3'-fluorobiphenyl-4-yl)ethanesulfonamide |
| PT-027 | N-(2,4'-dichloro-3'-fluorobiphenyl-4-yl)propane-1-sulfonamide |
| PT-028 | ethyl N-[2-chloro-3'-(trifluoromethoxy)biphenyl-4-yl]-N-(methylsulfonyl)glycinate |
| PT-029 | N-[2-chloro-3'-(trifluoromethoxy)biphenyl-4-yl]-N-(methylsulfonyl)glycine |
| PT-030 | N-(3,3'-dichloro-4'-fluorobiphenyl-4-yl)methanesulfonamide |

TABLE 9-continued

| ID (PT-nnn) | Name of Compound |
|---|---|
| PT-031 | N-(4'-fluoro-2-methoxybiphenyl-4-yl)methanesulfonamide |
| PT-032 | N-(4'-chloro-2-methoxybiphenyl-4-yl)methanesulfonamide |
| PT-033 | N-(4'-phenoxybiphenyl-4-yl)methanesulfonamide |
| PT-034 | N-(3-chloro-4'-phenoxybiphenyl-4-yl)methanesulfonamide |
| PT-035 | N-(2-chloro-2'-fluorobiphenyl-4-yl)methanesulfonamide |
| PT-036 | N-[2-chloro-3'-(trifluoromethyl)biphenyl-4-yl]methanesulfonamide |
| PT-037 | N-(2-chloro-4'-fluorobiphenyl-4-yl)methanesulfonamide |
| PT-038 | N-(2,3'-dichloro-4'-fluorobiphenyl-4-yl)methanesulfonamide |
| PT-039 | N-(3'-chloro-4'-fluoro-2-methylbiphenyl-4-yl)methanesulfonamide |
| PT-040 | N-[2-methyl-3'-(trifluoromethoxy)biphenyl-4-yl]methanesulfonamide |
| PT-041 | N-(2-chloro-5-methyl-4'-phenoxybiphenyl-4-yl)methanesulfonamide |
| PT-042 | N-(3-methyl-4'-phenoxybiphenyl-4-yl)methanesulfonamide |
| PT-043 | N-(2,4'-dichlorobiphenyl-4-yl)methanesulfonamide |
| PT-044 | methyl 2'-chloro-4'-[(methylsulfonyl)amino]biphenyl-4-carboxylate |
| PT-045 | N-(2,2'-dichloro-4'-fluorobiphenyl-4-yl)methanesulfonamide |
| PT-046 | N-(2-methyl-4'-phenoxybiphenyl-4-yl)methanesulfonamide |
| PT-047 | N-[2-chloro-3'-(trifluoromethoxy)biphenyl-4-yl]cyclopropanesulfonamide |
| PT-048 | N-(2-chloro-4'-phenoxybiphenyl-4-yl)cyclopropanesulfonamide |
| PT-049 | N-(2,3'-dichloro-4'-fluorobiphenyl-4-yl)cyclopropanesulfonamide |
| PT-050 | N-[2-chloro-4'-(trifluoromethoxy)biphenyl-4-yl]cyclopropanesulfonamide |
| PT-051 | N-(2-chloro-4'-methoxybiphenyl-4-yl)methanesulfonamide |
| PT-052 | N-(2-chloro-3'-fluorobiphenyl-4-yl)methanesulfonamide |
| PT-053 | N-(2,3'-dichlorobiphenyl-4-yl)methanesulfonamide |
| PT-054 | N-(2-chloro-3'-nitrobiphenyl-4-yl)methanesulfonamide |
| PT-056 | N-(4'-fluoro-2-methylbiphenyl-4-yl)methanesulfonamide |
| PT-057 | N-(3',4'-difluoro-2-methylbiphenyl-4-yl)methanesulfonamide |
| PT-058 | N-[2,4'-dichloro-3'-(trifluoromethyl)biphenyl-4-yl]methanesulfonamide |
| PT-059 | N-(4'-chloro-2,3'-difluorobiphenyl-4-yl)methanesulfonamide |
| PT-060 | N-[3'-(trifluoromethoxy)biphenyl-4-yl]cyclopropanesulfonamide |
| PT-061 | N-(2,4'-dichloro-3'-fluorobiphenyl-4-yl)-N-[2-(morpholin-4-yl)ethyl]methanesulfonamide |
| PT-062 | N-(2,4'-dichloro-3'-fluorobiphenyl-4-yl)-N-[2-(piperidin-1-yl)ethyl]methanesulfonamide |
| PT-063 | N-(2,4'-dichloro-3'-fluorobiphenyl-4-yl)-N-[2-(4-methylpiperazin-1-yl)ethyl]methanesulfonamide |
| PT-064 | N-(2,4'-dichloro-3'-fluorobiphenyl-4-yl)-N-(2H-tetrazol-5-ylmethyl)methanesulfonamide |
| PT-065 | N-[2-chloro-3',5'-bis(trifluoromethyl)biphenyl-4-yl]methanesulfonamide |
| PT-066 | N-(3-chloro-4'-phenoxybiphenyl-4-yl)-N-[(2S)-2-hydroxycyclopentyl]methanesulfonamide |
| PT-067 | N-[2-fluoro-3'-(trifluoromethoxy)biphenyl-4-yl]methanesulfonamide |
| PT-068 | N-(2-chloro-3',5'-difluorobiphenyl-4-yl)methanesulfonamide |
| PT-069 | N-[2-chloro-4'-fluoro-3'-(trifluoromethyl)biphenyl-4-yl]methanesulfonamide |
| PT-070 | N-[2-chloro-2'-fluoro-5'-(trifluoromethyl)biphenyl-4-yl]methanesulfonamide |
| PT-071 | N-(2-chloro-3',4',5'-trifluorobiphenyl-4-yl)methanesulfonamide |
| PT-072 | N-(4'-phenoxybiphenyl-4-yl)cyclopropanesulfonamide |
| PT-073 | N-[2-methyl-3'-(trifluoromethoxy)biphenyl-4-yl]-N-(pyridin-3-ylmethyl)methanesulfonamide |
| PT-074 | N-[4'-chloro-3'-fluoro-3-(trifluoromethoxy)biphenyl-4-yl]methanesulfonamide |
| PT-075 | N-[3-(trifluoromethoxy)-4'-(trifluoromethyl)biphenyl-4-yl]methanesulfonamide |
| PT-076 | N-[3-(trifluoromethoxy)-3'-(trifluoromethyl)biphenyl-4-yl]methanesulfonamide |
| PT-077 | N-(2,4'-dichloro-3'-fluorobiphenyl-4-yl)-N-(2-methoxyethyl)methanesulfonamide |
| PT-078 | N-[2-fluoro-4'-(trifluoromethoxy)biphenyl-4-yl]methanesulfonamide |
| PT-079 | N-[2-fluoro-3'-(trifluoromethyl)biphenyl-4-yl]methanesulfonamide |
| PT-080 | N-[2-fluoro-4'-(trifluoromethyl)biphenyl-4-yl]methanesulfonamide |
| PT-081 | N-[2-chloro-3'-(trifluoromethoxy)biphenyl-4-yl]-N-(pyridin-3-ylmethyl)cyclopropanesulfonamide |
| PT-082 | N-(2-methyl-4'-phenoxybiphenyl-4-yl)-N-(methylsulfonyl)glycine |
| PT-086 | N-[4'-(trifluoromethoxy)biphenyl-4-yl]methanesulfonamide |
| PT-089 | N-[2-methoxy-3'-(trifluoromethoxy)biphenyl-4-yl]-N-(methylsulfonyl)glycine |
| PT-092 | N-(2,4'-dichloro-3'-fluorobiphenyl-4-yl)-N-(methylsulfonyl)glycine |
| PT-094 | N-[2-chloro-4'-(trifluoromethoxy)biphenyl-4-yl]methanesulfonamide |
| PT-098 | N-(2',3-dichloro-4'-fluorobiphenyl-4-yl)methanesulfonamide |
| PT-099 | N-[3,4'-bis(trifluoromethoxy)biphenyl-4-yl]methanesulfonamide |
| PT-100 | N-[3,3'-bis(trifluoromethoxy)biphenyl-4-yl]methanesulfonamide |
| PT-101 | tert-butyl N-[2-fluoro-3'-(trifluoromethoxy)biphenyl-4-yl]-N-(methylsulfonyl)glycinate |
| PT-102 | tert-butyl N-(2,3'-dichloro-4'-fluorobiphenyl-4-yl)-N-(methylsulfonyl)glycinate |
| PT-103 | N-[2-fluoro-3'-(trifluoromethoxy)biphenyl-4-yl]-N-(methylsulfonyl)glycine |
| PT-104 | N-(2,3'-dichloro-4'-fluorobiphenyl-4-yl)-N-(methylsulfonyl)glycine |
| PT-105 | N-(2-methyl-4'-phenoxybiphenyl-4-yl)-N-(methylsulfonyl)alanine |
| PT-106 | N-(2-chloro-5-methyl-4'-chlorophenoxybiphenyl-4-yl)-N-(methylsulfonyl)glycine |
| PT-107 | tert-butyl 4-{[(2-methyl-4'-phenoxybiphenyl-4-yl)(methylsulfonyl)amino]methyl}benzoate |
| PT-108 | 4-{[(2-methyl-4'-phenoxybiphenyl-4-yl)(methylsulfonyl)amino]methyl}benzoic acid |
| PT-109 | N-[6-methoxy-3'-(trifluoromethoxy)biphenyl-3-yl]methanesulfonamide |
| PT-110 | N-(4'-chloro-3'-fluoro-6-methoxybiphenyl-3-yl)methanesulfonamide |
| PT-111 | N-[2-chloro-4'-(trifluoromethyl)biphenyl-4-yl]-N-(methylsulfonyl)glycine |
| PT-112 | 3-{[(2-methyl-4'-phenoxybiphenyl-4-yl)(methylsulfonyl)amino]methyl}benzoic acid |
| PT-113 | 4-{[(2-chloro-5-methyl-4'-phenoxybiphenyl-4-yl)(methylsulfonyl)amino]methyl}benzoic acid |
| PT-114 | N-[4'-phenoxy-3-(trifluoromethoxy)biphenyl-4-yl]cyclopropanesulfonamide |
| PT-115 | N-(3-cyano-4'-phenoxybiphenyl-4-yl)cyclopropanesulfonamide |
| PT-116 | methyl 4-[(cyclopropylsulfonyl)amino]-4'-phenoxybiphenyl-3-carboxylate |

TABLE 9-continued

| ID (PT-nnn) | Name of Compound |
|---|---|
| PT-117 | 4-[(cyclopropylsulfonyl)amino]-4'-phenoxybiphenyl-3-carboxylic acid |
| PT-118 | methyl 4-[(methylsulfonyl)amino]-4'-phenoxybiphenyl-3-carboxylate |
| PT-119 | N-[4'-phenoxy-3-(trifluoromethoxy)biphenyl-4-yl]methanesulfonamide |
| PT-120 | 4-[(methylsulfonyl)amino]-4'-phenoxybiphenyl-3-carboxylic acid |
| PT-121 | methyl 4-[(methylsulfonyl)amino]-4'-(trifluoromethyl)biphenyl-3-carboxylate |
| PT-122 | 4-[(methylsulfonyl)amino]-4'-(trifluoromethyl)biphenyl-3-carboxylic acid |
| PT-123 | N-methyl-4-(methylsulfonamido)-4'-phenoxybiphenyl-3-carboxamide |
| PT-124 | N-(2-cyano-4'-phenoxybipheny]-4-yl)cyclopropanesulfonamide |
| PT-125 | tert-butyl N-(2-methyl-4'-phenoxybiphenyl-4-yl)-N-(methylsulfonyl)glycinate |
| PT-126 | tert-butyl 2-(N-(2-methyl-4'-phenoxybiphenyl-4-yl)methylsulfonamido)propanoate |
| PT-127 | N-(4'-chlorobiphenyl-3-yl)-3-methoxybenzenesulfonamide |
| PT-128 | tert-butyl 2-(N-(2-chloro-4'-(trifluoromethyl)biphenyl-4-yl)methylsulfonamido)acetate |
| PT-129 | N-(2-ethynyl-4'-phenoxybiphenyl-4-yl)methanesulfonamide |
| PT-130 | N-(2-cyano-4'-(trifluoromethyl)biphenyl-4-yl)cyclopropanesulfonamide |
| PT-131 | 4-(3'-(methylsulfonamido)biphenyl-4-yloxy)benzoic acid |
| PT-132 | N-(3'-fluoro-4'-(trifluoromethyl)biphenyl-3-yl)methanesulfonamide |
| PT-133 | 2-(4-((N-(2-methyl-4'-phenoxybiphenyl-4-yl)cyclopropanesulfonamido)methyl)phenyl)acetic acid |
| PT-134 | 4-((N-(2-methoxy-4'-phenoxybiphenyl-4-yl)methylsulfonamido)methyl)benzoic acid |
| PT-135 | N-(4-(1H-tetrazol-5-yl)benzyl)-N-(2-chloro-4'-phenoxybiphenyl-4-yl)methanesulfonamide |
| PT-136 | 4-((N-(4'-(4-fluorophenoxy)-2-methylbiphenyl-4-yl)methylsulfonamido)methyl)benzoic acid |
| PT-137 | tert-butyl 4-((N-(4'-(4-fluorophenoxy)-2-methylbiphenyl-4-yl)methylsulfonamido)methyl)benzoate |
| PT-138 | N-methyl-4-(N-(4-(methylsulfonyl)benzyl)methylsulfonamido)-4'-phenoxybiphenyl-2-carboxamide |
| PT-139 | 4-(cyclopropanesulfonamido)-N-methyl-4'-phenoxybiphenyl-2-carboxamide |
| PT-140 | N-isopropyl-4-(methylsulfonamido)-4'-phenoxybiphenyl-2-carboxamide |
| PT-141 | 4-((N-(3'-fluoro-2-methyl-4'-phenoxybiphenyl-4-yl)methylsulfonamido)methyl)benzoic acid |
| PT-142 | 4-((N-(2-fluoro-5-methyl-4'-phenoxybiphenyl-4-yl)methylsulfonamido)methyl)benzoic acid |
| PT-143 | N-(2-methyl-4'-phenoxybiphenyl-4-yl)-N-(4-nitrobenzyl)methanesulfonamide |
| PT-144 | N-(4'-isopropoxy-2-methylbiphenyl-4-yl)methanesulfonamide |
| PT-145 | ethyl 4-((N-(4'-isopropoxy-2-methylbiphenyl-4-yl)methylsulfonamido)methyl)benzoate |
| PT-146 | 4-((N-(4'-isopropoxy-2-methylbiphenyl-4-yl)methylsulfonamido)methyl)benzoic acid |
| PT-147 | N-((2H-tetrazol-5-yl)methyl)-N-(2,4'-dichloro-3'-fluorobiphenyl-4-yl)methanesulfonamide |
| PT-148 | N-(3-chloro-4'-isopropoxybiphenyl-4-yl)methanesulfonamide |
| PT-149 | N-(3-chloro-4'-(4-fluorophenoxy)biphenyl-4-yl)methanesulfonamide |
| PT-150 | N-(4'-cyano-2-methylbiphenyl-4-yl)cyclopropanesulfonamide |
| PT-151 | N-(4'-isopropoxy-2-methylbiphenyl-4-yl)cyclopropanesulfonamide |
| PT-152 | N-(3-cyano-4'-isopropoxybiphenyl-4-yl)cyclopropanesulfonamide |
| PT-153 | tert-butyl 4-((N-(3-chloro-4'-phenoxybiphenyl-4-yl)methylsulfonamido)methyl)benzoate |
| PT-154 | 4-((N-(3'-fluoro-4'-(trifluoromethyl)biphenyl-3-yl)methylsulfonamido)methyl)benzoic acid |
| PT-155 | tert-butyl 4-((N-(3'-fluoro-4'-(trifluoromethyl)biphenyl-3-yl)methylsulfonamido)methyl)benzoate |
| PT-156 | 4-((N-(4'-phenoxybiphenyl-4-yl)methylsulfonamido)methyl)benzoic acid |
| PT-157 | N-(4'-isopropoxy-3-(2H-tetrazol-5-yl)biphenyl-4-yl)cyclopropanesulfonamide |
| PT-158 | N-(2-methyl-4'-(2H-tetrazol-5-yl)biphenyl-4-yl)cyclopropanesulfonamide |
| PT-159 | methyl hydrogen 4'-(4-fluorophenoxy)-4-(methylsulfonamido)biphenyl-3-ylphosphonate |
| PT-160 | tert-butyl 2-(4-((N-(2-chloro-4'-phenoxybiphenyl-4-yl)methylsulfonamido)methyl)phenyl)acetate |
| PT-161 | 2-(4-((N-(2-chloro-4'-phenoxybiphenyl-4-yl)methylsulfonamido)methyl)phenyl)acetic acid |
| PT-162 | 4-(cyclopropanesulfonamido)-N-(2-hydroxyethyl)-4'-(trifluoromethyl)biphenyl-3-carboxamide |
| PT-163 | N-(2-amino-4'-phenoxybiphenyl-4-yl)methanesulfonamide |
| PT-164 | N-(2-amino-4'-(trifluoromethyl)biphenyl-4-yl)methanesulfonamide |
| PT-165 | N-(4-(methylsulfonamido)-4'-(trifluoromethyl)biphenyl-2-yl)nicotinamide |

Example 17

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules.

Example 18

A tablet Formula (I)s prepared using the ingredients below:

| Ingredient | Quantity (mg/tablet) |
|---|---|
| Active Ingredient | 25.0 |
| Cellulose, microcrystalline | 200.0 |

-continued

| Ingredient | Quantity (mg/tablet) |
|---|---|
| Colloidal silicon dioxide | 10.0 |
| Stearic acid | 5.0 |

The components are blended and compressed to form tablets.

Example 19

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

Example 20

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Example 21

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Example 22

Suspensions, each containing 50 mg of active ingredient per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Example 23

A subcutaneous formulation may be prepared as follows:

| Ingredient | Quantity |
|---|---|
| Active Ingredient | 5.0 mg |
| Corn Oil | 1.0 mL |

Example 24

An injectable preparation is prepared having the following composition:

| Ingredients | Amount |
|---|---|
| Active ingredient | 2.0 mg/ml |
| Mannitol, USP | 50 mg/ml |
| Gluconic acid, USP | q.s. (pH 5-6) |
| water (distilled, sterile) | q.s. to 1.0 ml |
| Nitrogen Gas, NF | q.s. |

Example 25

A topical preparation is prepared having the following composition:

| Ingredients | grams |
|---|---|
| Active ingredient | 0.2-10 |
| Span 60 | 2.0 |
| Tween 60 | 2.0 |
| Mineral oil | 5.0 |

-continued

| Ingredients | grams |
|---|---|
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Example 26

Sustained Release Composition

| Ingredient | Weight Range % |
|---|---|
| Active ingredient | 50-95 |
| Microcrystalline cellulose (filler) | 1-35 |
| Methacrylic acid copolymer | 1-35 |
| Sodium hydroxide | 0.1-1.0 |
| Hydroxypropyl methylcellulose | 0.5-5.0 |
| Magnesium stearate | 0.5-5.0 |

The sustained release formulations of this invention are prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg, and 900-1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

Example 27

Activity testing is conducted in the Examples below using methods described herein and those well known in the art.

Sodium Current Screening Assays:

The late sodium current (Late INa) and peak sodium current (Peak INa) assays are performed on an automated electrophysiology platform, PatchXpress 7000A (MDS Analytical Technologies, Sunnyvale, Calif.), which uses the whole cell patch clamp technique to measure currents through the cell membrane of up to 16 cells at a time. The assay uses an HEK293 (human embryonic kidney) cell line heterologously expressing the wild-type human cardiac sodium channel, $hNa_v1.5$, purchased from Millipore (Billerica, Mass.). No beta subunits were coexpressed with the Na channel alpha subunit. Cells are maintained with standard tissue culture procedures and stable channel expression is maintained with 400 µg/ml Geneticin in the culture medium. Cells isolated for use on PatchXpress are incubated for 5 minutes in Versene 1λ and then for 2 minutes in 0.0125% Trypsin-EDTA (both at 37° C.) to ensure that 80-90% of the cells are single and not part of a cell cluster. Experiments are carried out at 24-27° C.

For both the Late INa and Peak INa assays, series resistance compensation is set to 50% and whole-cell compensation is performed automatically. Currents are low-pass filtered at 10 kHz and digitized at 31.25 kHz. Currents through open sodium channels are automatically recorded and stored in the DataXpress2 database (MDS Analytical Technologies, Sunnyvale, Calif.). Analysis is performed using DataXpress2 analysis software and data are compiled in Excel.

Compound stocks are routinely made in glass vials to 10 mM in dimethyl sulfoxide (DMSO). In some cases, when compounds are not soluble in DMSO, they are made in 100% ethanol. Stocks are sonicated as necessary. The extracellular solution for screening Late INa is composed of: 140 mM NaCl, 4 mM KCl, 1.8 mM $CaCl_2$, 0.75 mM $MgCl_2$, and 5 mM HEPES with pH adjusted to 7.4 using NaOH. The extracellular solution for screening Peak INa is composed of: 20 mM NaCl, 120 mM N-methyl-D glucamine, 4 mM KCl, 1.8 mM $CaCl_2$, 0.75 mM $MgCl_2$, and 5 mM HEPES with pH adjusted to 7.4 using HCl. The intracellular solution used to perfuse the inside of the cells for both the Late INa and Peak INa assays contains: 120 mM CsF, 20 mM CsCl, 5 mM EGTA, 5 mM HEPES and pH adjusted to 7.4 with CsOH. Compounds are diluted in extracellular solution to 10 µM in glass vials and then transferred to glass well plates before robotic addition to the cells. The 0Na extracellular solution used at the end of each experiment for the Late INa and Peak INa assays to measure baseline current contains: 140 mM N-methyl-D-glucamine; 4 mM KCl; 1.8 mM $CaCl_2$; 0.75 mM $MgCl_2$; 5 mM HEPES and pH was adjusted to 7.4 with HCl.

Late INa Screening Assay:

For the Late INa assay, sodium channels are activated every 10 seconds (0.1 Hz) by depolarizing the cell membrane to −20 mV for 250 milliseconds (ms) from a holding potential of −120 mV. In response to a −20 mV voltage step, typical $Na_v1.5$ sodium currents activate rapidly to a peak negative current and then inactivate nearly completely within 3-4 ins.

All compounds are tested to determine their activity in blocking the late sodium current. Late INa current is generated by adding 10 µM Tefluthrin (pyrethroid) to the extracellular solution while recording Na currents For some experiments, 50 nM ATX II (sea anemone toxin), another late Na activator, was used to generate the late component. Both activators generate late components that are large enough that block of the late component by compounds can be measured easily. For the purposes of the screening, late Na is defined as the mean current between 225 ms and 250 ms after stepping to −20 mV to activate Na channels. After establishing the whole cell recording configuration, late INa activators are added to each well 4 times over a 16-17 minute period so that the late component of the Na current reaches a stable value. Compounds are then added (typically at 10 μM), in the presence of late INa activator, with 3 additions over the course of 7 or 8 minutes. Measurements are made typically at the end of exposure to the third compound addition. Measurements are made at the end of exposure to the third compound addition and values are normalized to the current level when all Na$^+$ is removed from the extracellular solution after two additions of ONa-ECF. Results are reported as percent block of late INa Peak INa Screening Assay:

Compounds were also evaluated for their effect in several other assays, including their effect on Peak INa. After screening compounds against late INa, selected compounds are evaluated for their effect in several other assays, including their effect on peak INa. One goal of this program is to avoid significant block of peak INa. Since the peak INa in our cells can be very large, introducing artifacts in the recording, the concentration of Na$^+$ in the bath is reduced to 20 mM and a nonpermanent cation is added to compensate for the Na$^+$ that was removed to maintain the osmolarity and ionic strength of the solution (see solution details above). All measurements are normalized to the current level when all Na$^+$ is removed from the extracellular solution, after two additions of 0Na-ECF.

In some cases we measured the effect of compound on peak INa using data from the late INa assay. But often peak currents were too large to make this possible, requiring that we perform a separate assay to evaluate the effect on peak INa. For the original peak INa assay, we activate the channel every 10 seconds by depolarizing the cell membrane to −20 mV for 250 ms from a holding potential of −120 mV. After establishing the whole cell recording configuration, the recorded currents are allowed to stabilize for 6-7 minutes. Compound is added at 10 μM with three additions over an 8-9 minute period. Analysis of peak INa generally requires correction for rundown before determining the % block of peak current by the tested compound.

A new Peak INa screening assay was developed to allow assessment of the effect of compounds on peak INa at both low and high stimulation frequencies. The goal is to find compounds that are highly selective for block of late INa but do not block peak INa. A low stimulation frequency of 0.1 Hz is used to determine the effect of compound when the channel spends most of the time in the resting (closed) state and provides information about Tonic Block (TB). A higher stimulation frequency (3 Hz) is used to measure block of the channel when it spends more time in the activated and inactivated states, and provides a measure of Use-Dependent Block (UDB). The −100 mV holding potential and the 3 Hz stimulation frequency were chosen so that our benchmark compound would have a small but detectable effect under experimental conditions, allowing for direct comparison of new compounds with the benchmark.

For the new peak INa assay, Na$^+$ channels are activated by depolarizing the cell membrane to 0 mV for 20 ins from a holding potential of −100 mV. After establishing the whole cell recording configuration, channels are stimulated to open with low frequency stimulation (0.1 Hz) for 7 minutes so that we can monitor the recording and assess the extent to which the recording has stabilized. After this stabilization period the stimulation frequency is increased to 3 Hz for 2 minutes, and then returned to 0.1 Hz. Since 3 Hz stimulation causes a small decrease in the peak current even in the absence of compound, we use this internal control for each cell, when no compound is present, to correct the results from 3 Hz stimulation when compound is present. Following 3 Hz stimulation under control conditions, the cell is allowed to recover for 200 seconds before compound is added. Compound (10 μM) is added 3 times at 60 second intervals, while stimulating the channels to open at 0.1 Hz to monitor the progression of block. After the 3$^{rd}$ compound addition, a 320 second wait period is imposed to allow for equilibration before the second period of 3 Hz stimulation begins. TB is measured before the second period of 3 Hz stimulation. Both TB and UDB are analyzed by incorporating rundown correction for the peak INa and UDB is calculated by compensating for the small use-dependent effect of the stimulation protocol on peak INa in the absence of compound.

hERG Screening Assay:

Compounds were screened to test their activity in blocking the hERG potassium channel. The hERG channel is heterologously expressed in a CHO (Chinese Hamster Ovary) cell line. Cells are maintained with standard tissue culture procedures and stable channel expression is maintained with 500 μg/ml G418 in the culture medium. Cells are harvested for testing on the PatchXpress automated patch clamp with Accumax (Innovative Cell Technologies, San Diego, Calif.) to isolate single cells.

The following solutions are used for electrophysiological recordings. The external solution contains: 2 mM $CaCl_2$; 2 mM $MgCl_2$; 4 mM KCl; 150 mM NaCl; 10 mM Glucose; 10 mM HEPES (pH 7.4 with 1M NaOH, osmolarity). The internal solution contains: 140 mM KCl, 10 mM $MgCl_2$, 6 mM EGTA, 5 mM HEPES, 5 mM ATP (pH adjusted to 7.25 with KOH).

hERG channels are activated when the voltage is stepped to +20 mV from the −80 mV holding potential. During a 5 second step at +20 mV, the channels activate and then largely inactivate, so the currents are relatively small. Upon returning to −50 mV from +20 mV, hERG currents transiently become much larger as inactivation is rapidly removed and then the channel closes. The first step to −50 mV for 300 ms is used as a baseline for measuring the peak amplitude during the step to −50 mV after channel activation. The peak current at −50 mV is measured both under control conditions and after addition of compound.

All compounds are prepared as 10 mM DMSO stocks in glass vials. Stock solutions are mixed by vigorous vortexing and sonication for about 2 minutes at room temperature. For testing, compounds are diluted in glass vials using an intermediate dilution step in pure DMSO and then further diluted to working concentrations in external solution. Dilutions are prepared no longer than 20 minutes before use.

After achieving the whole-cell configuration, cells are monitored for 90 seconds to assess stability and washed with external solution for 66 seconds. The voltage protocol described above is then applied to the cells every 12 seconds and throughout the whole procedure. Only cells with stable recording parameters and meeting specified health criteria are allowed to enter the compound addition procedure.

External solution containing 0.1% DMSO (vehicle) is applied to the cells first to establish the control peak current amplitude. After allowing the current to stabilize for 3 to 5 minutes, 1 μM and then 10 μM test compounds are applied. Each compound concentration is added 4 times and cells are kept in test solution until the effect of the compound reaches steady state or for a maximum of 12 minutes. After addition of test compound, a positive control (1 μM Cisapride) is added and must block >95% of the current for the experiment to be considered valid. Washout in the external solution compartment is performed until the recovery of the current reaches steady state. Data are analyzed using DataXpress, Clampfit (Molecular Devices, Inc., Sunnyvale) and Origin 7 (Originlab Corp.)

L-Type Calcium Channel Activity Well-Plate Assay:

Cell Culture: IMR-32 (human neuroblastoma) cells were obtained from The American Type Culture Collection. The cells were maintained in MEM supplemented with 10% fetal bovine serum, 2 mM of L-glutamine, 100 IU/ml of penicillin, 50 µg/ml of streptomycin, 1% of sodium pyruvate, 1% of sodium bicarbonate and 1% of non-essential amino acid. The cells were cultured at 37° C. in a humidified 5% CO2/95% air incubator. Culture medium was changed every two days and cells were recultivated when they reached 70-80% confluent.

Assay: IMR-32 cells were seeded on a Microtest 96-well Assay Plate (BD FALCONTM) at a density of 200,000 cells/well in 200 µl culture medium for overnight. The culture medium was removed, and replaced by 120 µl Ca-4 dye (MDS Analytical Technologies, Sunnyvale, Calif.) in HBSS (1× Hank's Balanced Salt solution plus 20 mM HEPES, pH 7.4) containing 2 mM probenecid. Cells were then incubated for 1 hour at 37 in incubator. Testing compounds were diluted from 5 µM-50 µM in HBSS, and 40 µl were added in cells before assay. L-type calcium channel activities (Max Min) were measured after addition of 40 µl of 1 µM (−)Bay K 8644 plus 50 mM KCl (final concentration) using FlexStation (Molecular Devices) immediately after addition of testing compounds. The inhibition of L-type calcium channel activity by compounds was then calculated.

Compounds were tested and found to be effective using the described assay methods at a concentration of 1 µM and 10 µM in the late INa and Peak INa assays, and at 1 µM and 10 µM for the hERG and L-type calcium channel assays. The assay results demonstrated that the compounds tested showed activity as modulators of late sodium current, for example by inhibiting (or reducing) the late sodium current.

Compounds were tested using the described assay methods. Data are obtained obtained by testing the listed compounds at 10 µM and 1 µl concentrations in the late INa assay, and at 1 µM and 10 µM for the hERG and L-type calcium channel assays. Data are shown in Table 1 below for those compounds that inhibit Late Ina by at least 10% at the 10 µM concentration.

TABLE 10

| | Late INa Assay results | | | |
|---|---|---|---|---|
| | Late INa | Late INa | hERG Patch Clamp | |
| ID (PT-nnn) | % blk (10 µM test cmpd) | % blk (1 µM test cmpd) | hERG % blk 1 µm | hERG % blk 10 µm |
| PT-001 | 58.1 | | 10 | 66 |
| PT-002 | 21.8 | | | |
| PT-003 | 58.3 | 11.2 | 10 | 28.3 |
| PT-004 | 42.8 | | | |
| PT-005 | 20.5 | | | |
| PT-006 | 22.7 | | | |
| PT-007 | 34.9 | | | |
| PT-008 | 39.4 | | | |
| PT-009 | 20.9 | | | |
| PT-010 | 48.2 | | | |
| PT-011 | 47.6 | | | |
| PT-012 | 52 | | | |
| PT-013 | 54.1 | | 10.5 | 29 |
| PT-014 | 50.5 | | | |
| PT-015 | 60.8 | | | |
| PT-016 | 45.8 | | | |
| PT-017 | 69.5 | 34.8 | 21 | 80 |
| PT-018 | 50.6 | | 10 | 10 |
| PT-019 | 55 | | | |
| PT-020 | 52.9 | | | |
| PT-021 | 77.5 | 34 | | |
| PT-022 | 54.8 | | 10 | 92 |
| PT-023 | 48.2 | | | |
| PT-024 | 43.5 | | | |
| PT-025 | 60 | | | |
| PT-026 | 78.5 | 33.8 | 10 | 10 |
| PT-027 | 55.5 | | | |
| PT-028 | 62.1 | | | |
| PT-029 | 28.4 | | | |
| PT-030 | 41.4 | | | |
| PT-031 | 17.1 | | | |
| PT-032 | 42 | | | |
| PT-033 | 15.1 | | | |
| PT-034 | 69.7 | 25.9 | 10 | 10 |
| PT-035 | 48.2 | | | |
| PT-036 | 64.1 | | | |
| PT-037 | 40.4 | | | |
| PT-038 | 71 | 28.8 | | |
| PT-039 | 62.9 | | | |
| PT-040 | 68.3 | 32.5 | 10 | 25 |
| PT-041 | 59.3 | 45 | | |
| PT-042 | 25.5 | | | |
| PT-043 | 71.5 | 17.4 | | |
| PT-044 | 50.6 | | | |
| PT-045 | 57.5 | | | |
| PT-046 | 81.1 | 23.5 | 10 | 28.5 |
| PT-047 | 77.7 | 48.6 | 10 | 28.5 |
| PT-048 | 37.9 | | | |
| PT-049 | 60.1 | | 10 | 32 |
| PT-050 | 61 | | 2 | 47.5 |
| PT-051 | 27 | | | |
| PT-052 | 50.1 | | | |
| PT-053 | 72.2 | 29.9 | | |
| PT-054 | 41.3 | | | |
| PT-056 | 40.8 | | | |
| PT-057 | 35.9 | | | |
| PT-058 | 78.5 | 42.5 | | |
| PT-059 | 41.3 | | | |
| PT-060 | 54.4 | | 10 | 35.5 |
| PT-061 | 20.6 | | | |
| PT-062 | 74.8 | 25.7 | | |
| PT-063 | 48.8 | | | |
| PT-064 | 30.5 | | | |
| PT-065 | 85.6 | 27.8 | | |
| PT-066 | 33.8 | | | |
| PT-067 | 70.7 | 13.8 | | |
| PT-068 | 42.2 | | | |
| PT-069 | 63 | | | |
| PT-070 | 69.7 | | | |
| PT-071 | 59.5 | | | |
| PT-072 | 35.6 | | | |
| PT-073 | 64.4 | | | |
| PT-074 | 24.2 | | | |
| PT-075 | 24.4 | | | |
| PT-076 | 18.7 | | | |
| PT-077 | 27.2 | | | |
| PT-078 | 49.1 | | | |
| PT-079 | 53.2 | | | |
| PT-080 | 66 | | | |
| PT-081 | 40.4 | | | |
| PT-082 | 19.9 | | 10 | 10 |
| PT-086 | 9.4 | | | |
| PT-089 | −4.1 | | | |
| PT-092 | −2.4 | | | |
| PT-094 | 5.6 | | | |
| PT-098 | 36.4 | | | |
| PT-099 | 8.9 | | | |
| PT-100 | −0.7 | | | |
| PT-101 | 72.9 | | | |

TABLE 10-continued

Late INa Assay results

| ID (PT-nnn) | Late INa % blk (10 µM test cmpd) | Late INa % blk (1 µM test cmpd) | hERG Patch Clamp hERG % blk 1 µm | hERG Patch Clamp hERG % blk 10 µm |
|---|---|---|---|---|
| PT-102 | 53.6 | | | |
| PT-103 | 21.2 | | | |
| PT-104 | 14.2 | | | |
| PT-105 | 5.8 | | | |
| PT-106 | 42 | | | |
| PT-107 | 21.2 | | | |
| PT-108 | 55.6 | | 10 | 10 |
| PT-109 | 35.1 | | | |
| PT-110 | 39.9 | | | |
| PT-111 | 14.6 | | | |
| PT-112 | 35.5 | | 10 | 21.5 |
| PT-113 | 34 | | | |
| PT-114 | 14.1 | | | |
| PT-115 | 61.8 | | | |
| PT-116 | 11.2 | | | |
| PT-117 | 40.7 | | | |
| PT-118 | 40.8 | | | |
| PT-119 | 6.6 | | | |
| PT-120 | 27 | | | |
| PT-121 | 40.5 | | | |
| PT-122 | 25.4 | | | |
| PT-124 | 32.2 | | | |
| PT-127 | 25 | | | |
| PT-128 | 25.7 | | | |
| PT-129 | 44.4 | | | |
| PT-130 | 26 | | | |
| PT-131 | 20.8 | | | |
| PT-132 | 65.9 | | | |
| PT-133 | 34.1 | | | |
| PT-134 | 3.9 | | | |
| PT-135 | 9.7 | | | |
| PT-136 | 8.8 | | | |
| PT-138 | 12.6 | | | |
| PT-139 | 43.7 | | | |
| PT-140 | 47.4 | | | |
| PT-141 | 23.8 | | | |
| PT-142 | 2.7 | | | |
| PT-143 | 8.7 | | | |
| PT-144 | 44.7 | | | |
| PT-145 | 17.1 | | | |
| PT-146 | 3.65 | | | |
| PT-148 | 36.2 | | | |
| PT-149 | 58 | | | |
| PT-150 | 22.5 | | | |
| PT-151 | 32.6 | | | |
| PT-152 | 29 | | | |
| PT-154 | 7 | | | |
| PT-156 | 7.9 | | | |
| PT-157 | 5.8 | | | |
| PT-158 | 2.8 | | | |
| PT-159 | 36.1 | | | |
| PT-161 | 30.9 | | | |
| PT-162 | −5.3 | | | |
| PT-163 | 54.7 | | | |
| PT-164 | 12.2 | | | |
| PT-165 | −0.3 | | | |

The assay results shown in the above Table 10 establish that compounds tested showed activity as modulators of late sodium current, for example by inhibiting (or reducing) the late sodium current.

In some embodiments the effects of a compound of Formula (IA) or (IB) are specific for the late sodium current and show little or no activity with respect to one or more other ion channels. Thus, in some embodiments, a compound having an activity of reducing late sodium current will also exhibit little or no activity with regard to the peak sodium current. In particular embodiments, a compound having an activity of reducing late sodium current will also exhibit little or no activity with regard to the hERG potassium channel. In some embodiments, a compound having an activity of reducing late sodium current will also exhibit little or no activity with regard to the L-type calcium channel. For example, a given compound may provide a 30% (or greater, e.g. more than 40%, more than 50%, more than 60%, more than 70%, more than 80%) reduction in late sodium current in the assay described herein, and the same compound may exhibit little or no activity for one or more of the peak sodium current, the hERG potassium channel, and the L-type calcium channel. In this regard, a compound having "little" effect will typically show less then a 30% reduction (e.g. less than a 20% reduction, less than a 15% reduction, less than a 10% reduction) in the given activity (e.g. Peak INa, hERG, L-type calcium), when measured using the assay described herein. In this regard, "no" effect means that any activity measured will differ from the control by less than the standard error of the measurement. The assays conducted to measure activities in this regard should be performed as described above, with the compound at a concentration of 10 µM (or at the upper limit of solubility, if less).

L-type Ca2+Channel Assay—ChanTest

Selected compounds were screened for block of the cardiac L-type $Ca^{2+}$ channel (hCav1.2, encoded by the human CACNA1C gene and coexpressed with the beta 2 subunit, encoded by the human CACNB2 gene, and alpha2delta1, encoded by the CACNA2D1 gene). The $Ca^{2+}$ channel is heterologously expressed in a CHO (Chinese Hamster Ovary) cell line. Cells are maintained following standard tissue culture procedures and stable channel expression is maintained with appropriate selection antibiotics in the culture medium. Cells are harvested for testing on the PatchXpress automated patch clamp (Model 7000A, Molecular Devices, Sunnyvale, Calif.) by washing twice with Hank's Balanced Salt Solution, treating the cells with trypsin, and re-suspending cells in culture medium ($4$–$6 \times 10^6$ cells in 20 mL). Cells in suspension are allowed to recover for 10 minutes in a tissue culture incubator set at 37° C. in a humidified 95% air, 5% $CO_2$ atmosphere.

The following solutions are used for electrophysiological recordings. The external solution contains (mM): 137 NaCl, 4 KCl, 1.8 $CaCl_2$, 1 $MgCl_2$, 10 Glucose, 10 HEPES (pH 7.4 with NaOH). The internal solution contains (mM): 130 Cs Aspartate, 5 $MgCl_2$, 5 EGTA, 4 ATP, 0.1 GTP, 10 HEPES, (pH adjusted to 7.2 with N-methyl-D-glucamine).

Vehicle is applied to naïve cells ($n \geq 2$, where n=the number cells), for a 5-10 minute exposure interval. Each solution exchange is performed in quadruplicate. At the end of each experiment, a saturating concentration of nifedipine (10 µM) is added to block hCav1.2 current. Leak current is digitally subtracted from the total membrane current record.

Test compound stock solutions are prepared by addition of dimethyl sulfoxide (DMSO) and stored frozen. Each test compound DMSO stock is sonicated (Model 2510/5510, Branson Ultrasonics, Danbury, Conn.), at ambient room temperature for at least 20 minutes to facilitate dissolution. Test compound concentrations are prepared fresh daily by diluting stock solutions into the standard extracellular physiological saline solution (see above). The maximum percent of DMSO added with compound is 0.1%. All test compound and control solutions are placed in a glass-lined 96-well compound plate before loading on PatchXpress.

One or two concentrations (1, 10 µM) of each test compound is applied at five (5) minute intervals via disposable polyethylene micropipette tips to naïve cells (n≧2, where n=the number cells/concentration). Each test compound concentration is added to the cell in quadruplicate. Total duration of exposure to each test compound concentration is 5 minutes.

Onset and steady state block of hCav1.2 (α1C/β2/α2δ channels is measured using a stimulus voltage pattern consisting of a depolarizing test pulse (duration, 200 ms; amplitude, 10 mV) at 10 s intervals from a −80 mV holding potential. Peak current is measured during a step to 10 mV.

Na$_v$1.7 Screening Assay:

Evidence supports a role for the tetrodotoxin-sensitive Na$_v$1.7 in the pathogenesis of pain. In this assay, whole-cell patch-clamp techniques were used to determine the effects of compounds of Formula (I) on human Nav1.7 (hNav1.7+β1 subunits) channels expressed in HEK293 cells. The Na$_v$1.7 cell line was prepared by stably transfecting HEK293 cells with human Na$_v$1.7α unit and β1 subunit. HEK293 cells stably expressing huNa$_v$1.7 were analysed by patch clamp techniques and were found to have Na$^+$ currents between −400 and −1800 pA (no currents were recorded in untransfected cells). The Na$^+$ current in these cells was blocked by tetrodotoxin (TTX) with an IC$_{50}$ value of 10-74 nmol/L. Similar results were obtained by use of membrane potential-sensitive dyes.

Stock solutions of compounds of Formula (IA) and (IB) ("test compounds") were prepared in DMSO at a concentration of 40 mmol/L just prior to use. Each test compound was tested in duplicate at 100 μM, then a 1 in 4 serial dilution to yield 8 concentrations for testing. TTX was used as a control inhibitor of Na$_v$1.7 current.

The effect of test compounds to reduce Na$_v$1.7 Na$^+$ current was measured using a fluorescent dye-based membrane potential assay kit (#R8123) from Molecular Devices (California, USA). Briefly, cells were seeded into poly-D-lysine pre-coated black-wall, clear-bottom 96-well Biocoat plates in 100 μl growth media 24 h prior to assay. On the day of the assay the membrane potential dye was prepared and pre-warmed with Hepes-HBSS solution to 37° C. To each well, 100 μl dye was added and incubated at 37° C. for 60 min. Veratridine was added to each well to achieve a final concentration of 50 μmol/L. Test compound was then added to each well in the desired concentration, and fluorescence was recorded. For each test compound data set, an IC$_{50}$ value was calculated based on the assay points generated.

In particular embodiments, a compound will exhibit a high selectivity for the late sodium current modulatory activity as compared to the activity in one or more other ion channels. The selectivity of a compound may be determined by determining the percentage reduction in late sodium current due to the compound, as measured by the assay described above. The percentage reduction in one other ion channel activity, such as the hERG potassium channel or L-type calcium channel, due to the compound is determined as described above. The selectivity is determined by taking the ratio of (percentage reduction in late sodium current) to (percentage reduction in one other ion channel activity). The assays conducted to measure activities in this regard should be performed as described above, with the compound at a concentration of 10 μM (or at the upper limit of solubility, if less). In particular embodiments, the selectivity of a compound of the invention will be at least 5:1, e.g. at least 6:1, at least 7:1, at least 8:1, at least 9:1, at least 10:1, at least 12:1, at least 15:1, at least 20:1, or at least 25:1, when comparing the percentage reduction in late sodium current versus percentage reduction of one of the peak sodium current, the hERG potassium channel current, or the L-type calcium channel.

What is claimed is:

1. A method of treating a disease state in a mammal that is alleviable by treatment with an agent capable of reducing late sodium current, comprising administering to a mammal in need thereof a therapeutically effective dose of a compound of Formula (IA) or (IB):

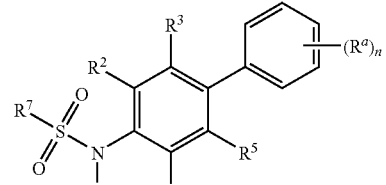

Formula (IA)

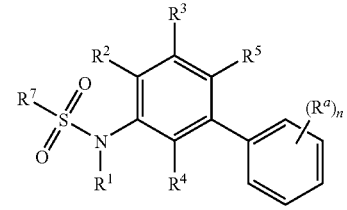

Formula (IB)

wherein:
R$^1$ is hydrogen, C$_{1-4}$ alkyl, —R$^{25}$—O—R$^{20}$, —R$^{25}$—C(O)—O—R$^{20}$, —R$^{25}$—C(O)NHS(O)$_2$R$^{20}$, —R$^{25}$-optionally substituted monocyclic heterocyclyl, —R$^{25}$-optionally substituted monocyclic cycloalkyl, —R$^{25}$-optionally substituted monocyclic heteroaryl, —R$^{25}$-optionally substituted monocyclic aryl;
  wherein the heterocyclyl, cycloalkyl, aryl, and heteroaryl are optionally substituted with one, two, or three substituents independently selected from halo, hydroxyl, alkyl, —R$^{25}$—C(O)—O—R$^{20}$, —R$^{25}$—S(O)$_2$—R$^{20}$, lower alkoxy, —CF$_3$, —CN, amino, —NO$_2$, mono- or dialkylamino, and heteroaryl;
R$^2$ and R$^5$ are each independently selected from the group consisting of hydrogen, C$_{1-4}$alkyl, halo, CN, —CF$_3$, —O—R$^{20}$, —S—R$^{20}$, —C(O)—O—R$^{20)}$—C(O)—N(R$^{20}$)(R$^{22}$), and —P(O)(OR$^{20}$)$_2$;
R$^3$ and R$^4$ are hydrogen;
R$^7$ is C$_{1-4}$ alkyl or cycloalkyl;
R$^a$ are each independently selected from the group consisting of C$_{1-4}$ alkyl, halo, CN,—NO$_2$, —CF$_3$, —O—R$^{20}$, —S—R$^{20}$, —C(O)—O—R$^{20}$,—C(O)—N(R$^{20}$)(R$^{22}$), —N(R$^{20}$)(R$^{22}$)—N(R$^{20}$)—C(O)—R$^{22}$,—P(O)(OR$^{20}$)$_2$, —R$^{25}$-optionally substituted monocyclic heteroaryl, and —R$^{25}$ -optionally substituted monocyclic aryl; provided that the optionally substituted monocyclic heteroaryl is not a 6-membered monocyclic heteroaryl group;
  wherein the aryl and heteroaryl are optionally substituted with one, two, or three substituents independently selected from halo, hydroxyl, alkyl, monoalkylamino, dialkylamino, alkyl, aryl or heteroaryl amide, —CN, lower alkoxy, —CF$_3$, aryl, and heteroaryl;
n is 0, 1, 2, or 3;
R$^{20}$ and R$^{22}$ are in each instance independently selected from the group consisting of hydrogen, C$_1$-C$_{15}$ alkyl, C$_2$-C$_{15}$ alkenyl, C$_2$-C$_{15}$ alkynyl, heterocyclyl, aryl, and heteroaryl;
  wherein the alkyl, alkenyl, alkynyl, heterocyclyl, aryl, and heteroaryl are optionally substituted with one, two, or three substituents independently selected from halo, hydroxyl, alkyl, mono- or dialkylamino, alkyl, aryl or heteroaryl amide, —CN, lower alkoxy, —CF$_3$, aryl, and heteroaryl;

$R^{25}$ is in each instance independently a covalent bond or selected from C$_1$-C$_3$ alkylene optionally substituted with one or two C$_1$-C$_3$ alkyl groups;

or a pharmaceutically acceptable salt or ester thereof.

2. The method of claim 1, wherein the compound has the structure of Formula (IA).

3. The method of claim 2, wherein:

$R^1$ is $R^{25}$—O—$R^{20}$, —$R^{25}$—C(O)—O—$R^{20}$, —$R^{25}$-optionally substituted monocyclic heterocyclyl, —$R^{25}$-optionally substituted monocyclic cycloalkyl —R25-optionally substituted monocyclic heteroaryl, and —$R^{25}$-optionally substituted monocyclic aryl, wherein the heterocyclyl, cycloalkyl, aryl, and heteroaryl are optionally substituted with one, two, or three substituents independently selected from halo, hydroxyl, alkyl, —$R^{25}$-C(O)—O—$R^{20}$, —$R^{25}$—S(O)$_2$—$R^{20}$, lower alkoxy, —CF$_3$, —CN, amino, —NO$_2$, mono- or dialkylamino, and heteroaryl; and $R^{25}$ is C$_1$-C$_3$ alkylene optionally substituted with one or two C$_1$-C$_3$ alkyl groups.

4. The method of claim 2, wherein n is 1; and $R^a$ is phenoxy optionally substituted with one, two, or three substituents independently selected from the group consisting of halo, hydroxyl, alkyl, monoalkylamino, dialkylamino, alkyl, aryl, heteroaryl amide, —CN, lower alkoxy, —CF$_3$, aryl, and heteroaryl.

5. The method of claim 4, wherein the compound is selected from

N-(4'-phenoxybiphenyl-4-yl)methanesulfonamide;

N-(3-chloro-4'-phenoxybiphenyl-4-yl)methanesulfonamide;

N-(2-chloro-5-methyl-4'-phenoxybiphenyl-4-yl)methanesulfonamide;

N-(3-methyl-4'-phenoxybiphenyl-4-yl)methanesulfonamide;

N-(2-methyl-4'-phenoxybiphenyl-4-yl)methanesulfonamide;

N-(3-chloro-4'-phenoxybiphenyl-4-yl)-N-[(2S)-2-hydroxycyclopentyl]methanesulfonamide;

methyl 4-[(methylsulfonyl)amino]-4'-phenoxybiphenyl-3-carboxylate;

N-[4'-phenoxy-3-(trifluoromethoxy)biphenyl-4-yl]methanesulfonamide;

4-[(methylsulfonyl)amino]-4'-phenoxybiphenyl-3-carboxylic acid;

N-methyl-4-(methylsulfonamido)-4'-phenoxybiphenyl-3-carboxamide;

N-(2-ethynyl-4'-phenoxybiphenyl-4-yl)methanesulfonamide;

N-isopropyl-4-(methylsulfonamido)-4'-phenoxybiphenyl-2-carboxamide;

N-(3-chloro-4'-(4-fluorophenoxy)biphenyl-4-yl)methanesulfonamide;

methyl hydrogen 4'-(4-fluorophenoxy)-4-(methylsulfonamido)biphenyl-3-ylphosphonate; and N-(2-amino-4'-phenoxybiphenyl-4-yl)methanesulfonamide.

6. The method of claim 4, wherein $R^1$ is $R^{25}$—O—$R^{20}$, —$R^{25}$—C(O)—O—$R^{20}$, —$R^{25}$-optionally substituted monocyclic heterocyclyl, —$R^{25}$-optionally substituted monocyclic cycloalkyl —$R^{25}$-optionally substituted monocyclic heteroaryl, and —$R^{25}$-optionally substituted monocyclic aryl, wherein the heterocyclyl, cycloalkyl, aryl, and heteroaryl are optionally substituted with one, two, or three substituents independently selected from halo, hydroxyl, alkyl, —$R^{25}$—C(O)O—$R^{20}$, —$R^{25}$—S(O)$_2$—$R^{20}$, lower alkoxy, —CF$_3$, —CN, amino, —NO$_2$, mono- or dialkylamino, and heteroaryl; and $R^{25}$ is C$_1$-C$_3$ alkylene optionally substituted with one or two C$_1$-C$_3$ alkyl groups.

7. The method of claim 6, wherein the compound is selected from

N-(2-methyl-4'-phenoxybiphenyl-4-yl)-N-(methylsulfonyl)glycine;

N-(2-methyl-4'-phenoxybiphenyl-4-yl)-N-(methylsulfonyl)alanine;

N-(2-chloro-5-methyl-4'-phenoxybiphenyl-4-yl)-N-(methylsulfonyl)glycine;

tert-butyl N-(2-methyl-4'-phenoxybiphenyl-4-yl)-N-(methylsulfonyl)glycinate; and tert-butyl 2-(N-(2-methyl-4'-phenoxybiphenyl-4-yl)methylsulfonamido)propanoate.

8. The method of claim 4, wherein $R^1$ is $R^{25}$-phenyl, wherein the phenyl ring is optionally substituted with one, two, or three substituents independently selected from halo, hydroxyl, alkyl, —$R^{25}$—C(O)—O—$R^{20}$, —$R^{25}$—S(O)$_2$—$R^{20}$, lower alkoxy, —CF$_3$, —CN, amino, —NO$_2$, mono- or dialkylamino, and heteroaryl; and $R^{25}$ is C$_1$-C$_3$ alkylene optionally substituted with one or two C$_1$-C$_3$ alkyl groups.

9. The method of claim 8, wherein the compound is selected from tert-butyl 4-{[(2-methyl-4'-phenoxybiphenyl-4-yl)(methylsulfonyl)amino]methyl}benzoate;

4-{[(2-methyl-4'-phenoxybiphenyl-4-yl)(methylsulfonyl)amino]methyl}benzoic acid;

3-{[(2-methyl-4'-phenoxybiphenyl-4-yl)(methylsulfonyl)amino]methyl}benzoic acid;

4-{[(2-chloro-5-methyl-4'-phenoxybiphenyl-4-yl)(methylsulfonyl)amino]methyl}benzoic acid;

4-((N-(2-methoxy-4'-phenoxybiphenyl-4-yl)methylsulfonamido)methyl)benzoic acid;

N-(4-(1H-tetrazol-5-yl)benzyl)-N-(2-chloro-4'-phenoxybiphenyl-4-yl)methanesulfonamide;

4-((N-(4'-(4-fluorophenoxy)-2-methylbiphenyl-4-yl)methylsulfonamido)methyl)benzoic acid;

tert-butyl 4-((N-(4'-(4-fluorophenoxy)-2-methylbiphenyl-4-yl)methylsulfonamido)methyl)benzoate;

N-methyl-4-(N-(4-(methylsulfonyl)benzyl)methylsulfonamido)-4'-phenoxybiphenyl-2-carboxamide;

4((N-(2-fluoro-5-methyl-4'-phenoxybiphenyl-4-yl)methylsulfonamido)methyl)benzoic acid;

N-(2-methyl-4'-phenoxybiphenyl-4-yl)-N-(4-nitrobenzyl)methanesulfonamide;

4((N-(3'-fluoro-2-methyl-4'-phenoxybiphenyl-4-yl)methylsulfonamido)methyl)benzoic acid;

tert-butyl 4((N-(3-chloro-4'-phenoxybiphenyl-4-yl)methylsulfonamido)methyl)benzoate, 4((N-(4'-phenoxybiphenyl-4-yl)methylsulfonamido)methyl)benzoic acid;

tert-butyl 2-(4((N-(2-chloro-4'-phenoxybiphenyl-4-yl)methylsulfonamido)methyl)phenyl)acetate; and 2-(4((N-(2-chloro-4'-phenoxybiphenyl-4-yl)methylsulfonamido)methyl)phenyl)acetic acid.

10. The method of claim 4, wherein $R^7$ is cycloalkyl.

11. The method of claim 10, wherein the compound is selected from
- N-(2-chloro-4'-phenoxybiphenyl-4-yl)cyclopropanesulfonamide;
- N-(4'-phenoxybiphenyl-4-yl)cyclopropanesulfonamide;
- N-[4'-phenoxy-3-(trifluoromethoxy)biphenyl-4-yl]cyclopropanesulfonamide;
- N-(3-cyano-4'-phenoxybiphenyl-4-yl)cyclopropanesulfonamide;
- methyl 4-[(cyclopropylsulfonyl)amino]-4'-phenoxybiphenyl-3-carboxylate;
- 4-[(cyclopropylsulfonyl)amino]-4'-phenoxybiphenyl-3-carboxylic acid;
- N-(2-cyano-4'-phenoxybiphenyl-4-yl)cyclopropanesulfonamide;
- 2-(4((N-(2-methyl-4'-phenoxybiphenyl-4-yl)cyclopropanesulfonamido)methyl)methyl)phenyl)acetic acid; and
- 4-(cyclopropanesulfonamido)-N-methyl-4'-phenoxybiphenyl-2-carboxamide.

12. The method of claim 3, wherein the compound is selected from
- ethyl N-(4'-chloro-3'-fluoro-2-methoxybiphenyl-4-yl)-N-(methylsulfonyl)glycinate;
- ethyl N-[2-methoxy-3'-(trifluoromethoxy)biphenyl-4-yl]-N-(methylsulfonyl)glycinate;
- ethyl N-(2,4'-dichloro-3'-fluorobiphenyl-4-yl)-N-(methylsulfonyl)glycinate;
- ethyl N-[2-chloro-3'-(trifluoromethoxy)biphenyl-4-yl]-N-(methylsulfonyl)glycinate;
- N-[2-chloro-3'-(trifluoromethoxy)biphenyl-4-yl]-N-(methylsulfonyl)glycine;
- N-(2,4'-dichloro-3'-fluorobiphenyl-4-yl)-N-[2-(morpholin-4-yl)ethyl]methanesulfonamide;
- N-(2,4'-dichloro-3'-fluorobiphenyl-4-yl)-N-[2-(piperidin-1-yl)ethyl]methanesulfonamide;
- N-(2,4'-dichloro-3'-fluorobiphenyl-4-yl)-N-[2-(4-methylpiperazin-1-yl)ethyl]methanesulfonamide;
- N-(2,4'-dichloro-3'-fluorobiphenyl-4-yl)-N-(2H-tetrazol-5-ylmethyl)methanesulfonamide;
- N-(2,4'-dichloro-3'-fluorobiphenyl-4-yl)-N-(2-methoxyethyl)methanesulfonamide;
- N-[2-methoxy-3'-(trifluoromethoxy)biphenyl-4-yl]-N-(methylsulfonyl)glycine;
- N-(2,4'-dichloro-3'-fluorobiphenyl-4-yl)-N-(methylsulfonyl)glycine;
- tert-butyl N-[2-fluoro-3'-(trifluoromethoxy)biphenyl-4-yl]-N-(methylsulfonyl)glycinate;
- tert-butyl N-(2,3'-dichloro-4'-fluorobiphenyl-4-yl)-N-(methylsulfonyl)glycinate;
- N-[2--fluoro-3'-(trifluoromethoxy)biphenyl-4-yl]-N-(methylsulfonyl)glycine;
- N-(2,3'-dichloro-4'-fluorobiphenyl-4-yl)-N-(methylsulfonyl)glycine;
- N-[2--chloro-4'-(trifluoromethyl)biphenyl-4-yl]-N-(methylsulfonyl)glycine;
- tert-butyl 2-(N-(2-chloro-4'-(trifluoromethyl)biphenyl-4-yl)methylsulfonamido)acetate; and
- N-((2H-tetrazol-5-yl)methyl)-N-(2,4'-dichloro-3'-fluorobiphenyl-4-yl)methanesulfonamide.

13. The method of claim 2, wherein:
$R^1$ is $R^{25}$-phenyl,
wherein the phenyl ring is optionally substituted with one, two, or three substituents independently selected from halo, hydroxyl, alkyl, —$R^{25}$—C(O)—O—$R^{20}$, —$R^{25}$—S(O)$_2$—$R^{20}$, lower alkoxy, —CF$_3$, —CN, amino, —NO$_2$, mono- or dialkylamino, and heteroaryl; and
$R^{25}$ is $C_1$-$C_3$ alkylene optionally substituted with one or two $C_1$-$C_3$ alkyl groups.

14. The method of claim 3, wherein the compound is selected from
- ethyl 4-((N-(4'-isopropoxy-2-methylbiphenyl-4-yl)methylsulfonamido)methyl)benzoate; and
- 4-((N-(4'-isopropoxy-2-methylbiphenyl-4-yl)methylsulfonamido)methyl)benzoic acid.

15. The method of claim 2, wherein the compound is selected from
- N-[2-chloro-3'-(trifluoromethoxy)biphenyl-4-yl]cyclopropanesulfonamide;
- N-(2,3'-dichloro-4'-fluorobiphenyl-4-yl)cyclopropanesulfonamide;
- N-[2-chloro-4'-(trifluoromethoxy)biphenyl-4-yl]cyclopropanesulfonamide;
- N-[3'-(trifluoromethoxy)biphenyl-4-yl]cyclopropanesulfonamide;
- N-(2-cyano-4'-(trifluoromethyl)biphenyl-4-yl)cyclopropanesulfonamide;
- N-(4'-cyano-2-methylbiphenyl-4-yl)cyclopropanesulfonamide;
- N-(4'-isopropoxy-2-methylbiphenyl-4-yl)cyclopropanesulfonamide;
- N-(3-cyano-4'-isopropoxybiphenyl-4-yl)cyclopropanesulfonamide;
- N-(4'-isopropoxy-3-(2H-tetrazol-5-yl)biphenyl-4-yl)cyclopropanesulfonamide,
- N-(2-methyl-4'-(2H-tetrazol-5-yl)biphenyl-4-yl)cyclopropanesulfonamide; and
- 4-(cyclopropanesulfonamido)-N-(2-hydroxyethyl)-4'-(trifluoromethyl)biphenyl-3-carboxamide.

16. The method of claim 2, wherein
$R^1$ is $R^{25}$—O—$R^{20}$, —$R^{25}$—C(O)—O—$R^{20}$, —$R^{25}$-optionally substituted monocyclic heterocyclyl, —$R^{25}$-optionally substituted monocyclic cycloalkyl —$R^{25}$-optionally substituted monocyclic heteroaryl, and —$R^{25}$-optionally substituted monocyclic aryl,
wherein the heterocyclyl, cycloalkyl, aryl, and heteroaryl are optionally substituted with one, two, or three substituents independently selected from halo, hydroxyl, alkyl, —R25—C(O)—O—$R^{20,}$ $^{-R25}$—S(O)$_2$—$R^{20}$, lower alkoxy, —CF$_3$, —CN, amino, —NO$_2$, mono- or dialkylamino, and heteroaryl;
$R^{25}$ is $C_1$-$C_3$ alkylene optionally substituted with one or two $C_1$-$C_3$ alkyl groups; and
$R^7$ is cycloalkyl.

17. The method of claim 2, wherein
$R^1$ is $R^{25}$-phenyl optionally substituted with one, two, or three substituents independently selected from halo, hydroxyl, alkyl, —$R^{25}$—C(O)—O—$R^{20}$, —$R^{25}$—S(O)$_2$—$R^{20}$, lower alkoxy, —CF$_3$, —CN, amino, —NO$_2$, mono-or dialkylamino, and heteroaryl;
$R^{25}$ is $C_1$-$C_3$ alkylene optionally substituted with one or two $C_1$-$C_3$ alkyl groups; and
$R^7$ is cycloalkyl.

18. The method of claim 1, wherein the compound has the structure of Formula (IB).

19. The method of claim 18, wherein the compound is selected from
- N-[6-methoxy-3'-(trifluoromethoxy)biphenyl-3-yl]methanesulfonamide;
- N-(4'-chloro-3'-fluoro-6-methoxybiphenyl-3-yl)methanesulfonamide;

N-(4'-chlorobiphenyl-3-yl)-3-methoxybenzenesulfonamide;
N-(3'-fluoro-4'-(trifluoromethyl)biphenyl-3-yl)methanesulfonamide;
4-(3'-(methylsulfonamido)biphenyl-4-yloxy)benzoic acid;
4-((N-(3'-fluoro-4'-(trifluoromethyl)biphenyl-3-yl)methylsulfonamido)methyl)benzoic acid; and
tert-butyl 4-((N-(3'-fluoro-4'-(trifluoromethyl)biphenyl-3-yl)methylsulfonamido)methyl)benzoate.

20. The method of claim 1, wherein the compound is selected from

N-[3'-(trifluoromethyl)biphenyl-4-yl]methanesulfonamide;
N-(3',4'-difluorobiphenyl-4-yl)methanesulfonamide;
N-(4'-chloro-3'-fluoro-2-methoxybiphenyl-4-yl)methanesulfonamide;
N-[2-methoxy-4'-(trifluoromethyl)biphenyl-4-yl]methanesulfonamide;
N-(4'-chloro-3'-fluorobiphenyl-4-yl)methanesulfonamide,
N-[4'-(trifluoromethyl)biphenyl-4-yl]methanesulfonamide;
N-(3'-chloro-4'-fluorobiphenyl-4-yl)methanesulfonamide;
N-[3'-(trifluoromethoxy)biphenyl-4-yl]methanesulfonamide;
N-[2-methoxy-4'-(trifluoromethoxy)biphenyl-4-yl]methanesulfonamide;
N-[2-methoxy-3'-(trifluoromethoxy)biphenyl-4-yl]methanesulfonamide;
N-[2-methoxy-2'-(trifluoromethoxy)biphenyl-4-yl]methanesulfonamide;
N-[4'-chloro-3'-fluoro-2-(trifluoromethyl)biphenyl-4-yl]methanesulfonamide;
N-[2,4'-bis(trifluoromethyl)biphenyl-4-yl]methanesulfonamide;
N-[4'-(trifluoromethoxy)-2-(trifluoromethyl)biphenyl-4-yl]methanesulfonamide;
N-[3'-(trifluoromethoxy)-2-(trifluoromethyl)biphenyl-4-yl]methanesulfonamide;
N-[2-'-(trifluoronnethoxy)-2-(trifluoromethyl)biphenyl-4-yl]methanesulfonamide;
N-(2,4'-dichloro-3'-fluorobiphenyl-4-yl)methanesulfonamide;
N-[2-chloro-4'-(trifluoromethyl)biphenyl-4-yl]methanesulfonamide;
N-[2-chloro-3'-(trifluoromethoxy)biphenyl-4-yl]methanesulfonamide;
N-[2-chloro-2'-(trifluoromethoxy)biphenyl-4-yl]methanesulfonamide,
N-(2-chloro-3',4'-difluorobiphenyl-4-yl)methanesulfonamide;
N-(2-chloro-2',4'-difluorobiphenyl-4-yl)methanesulfonamide,
N-(2,4'-dichloro-3'- -fluorobiphenyl-4-yl)ethanesulfonamide,
N-(2,4'-dichloro-3'-fluorobiphenyl-4-yl)propane-1-sulfonamide;
N-(3,3'-dichloro-4'-fluorobiphenyl-4-yl)methanesulfonamide;
N-(4'-fluoro-2-methoxybiphenyl-4-yl)methanesulfonamide;
N-(4'-chloro-2-methoxybiphenyl-4-yl)methanesulfonamide;
N-(2-chloro-2'-fluorobiphenyl-4-yl)methanesulfonamide;
N-[2-chloro-3'-(trifluoromethyl)biphenyl-4-yl]methanesulfonamide;
N-(2-chloro-4'-fluorobiphenyl-4-yl)methanesulfonamide;
N-(2,3'-dichloro-4'-fluorobiphenyl-4-yl)methanesulfonamide;
N-(3'-chloro-4'-fluoro-2-methylbiphenyl-4-yl)methanesulfonamide;
N-[2-methyl-3'-(trifluoromethoxy)biphenyl-4-yl]methanesulfonamide;
N-(2,4'-dichlorobiphenyl-4-yl)methanesulfonamide;
methyl 2'-chloro-4'-[(methylsulfonyl)amino]biphenyl-4-carboxylate;
N-(2,2'-dichloro-4'-fluorobiphenyl-4-yl)methanesulfonamide;
N-(2-chloro-4'-methoxybiphenyl-4-yl)methanesulfonamide;
N-(2-chloro-3'-fluorobiphenyl-4-yl)methanesulfonamide;
N-(2,3'-dichlorobiphenyl-4-yl)methanesulfonamide;
N-(2-chloro-3'-nitrobiphenyl-4-yl)methanesulfonamide;
N-(4'-fluoro-2-methylbiphenyl-4-yl)methanesulfonamide;
N-(3',4'-difluoro-2-methylbiphenyl-4-yl)methanesulfonamide;
N-[2,4'-dichloro-3'-(trifluoromethyl)biphenyl-4-yl]methanesulfonamide;
N-(4'-chloro-2,3'-difluorobiphenyl-4-yl)methanesulfonamide;
N-[2-chloro-3',5'-bis(trifluoromethyl)biphenyl-4-yl]methanesulfonamide;
N-[2-fluoro-3'-(trifluoromethoxy)biphenyl-4-yl]methanesulfonamide;
N-(2-chloro-3',5'-difluorobiphenyl-4-yl)methanesulfonamide;
N-[2-chloro-4'-fluoro-3'-(trifluoromethyl)biphenyl-4-yl]methanesulfonamide;
N-[2-chloro-2'-fluoro-5'-(trifluoromethyl)biphenyl-4-yl]methanesulfonamide;
N-(2-chloro-3',4',5'-trifluorobiphenyl-4-yl)methanesulfonamide;
N-[4'-chloro-3'-fluoro-3-(trifluoromethoxy)biphenyl-4-yl]methanesulfonamide;
N-[3-(trifluoromethoxy)-4'-(trifluoromethyl)biphenyl-4-yl]methanesulfonamide,
N-[3-(trifluoromethoxy)-3'-(trifluoromethyl)biphenyl-4-yl]methanesulfonamide;
N-[2-fluoro-4'-(trifluoromethoxy)biphenyl-4-yl]methanesulfonamide;
N-[2-fluoro-3'-(trifluoromethyl)biphenyl-4-yl]methanesulfonamide,
N-[2-fluoro-4'-(trifluoromethyl)biphenyl-4-yl]methanesulfonamide;
N-[4'-(trifluoromethoxy)biphenyl-4-yl]methanesulfonamide;
N-[2-chloro-4'-(trifluoromethoxy)biphenyl-4-yl]methanesulfonamide;
N-(2',3-dichloro-4'-fluorobiphenyl-4-yl)methanesulfonamide;
N[3,4'-bis(trifluoromethoxy)biphenyl-4-yl]methanesulfonamide,
N-[3,3'-bis(trifluoromethoxy)biphenyl-4-yl]methanesulfonamide;
methyl 4-[(methylsulfonyl)amino]-4'-(trifluoromethyl)biphenyl-3-carboxylate;
4-[(methylsulfonyl)amino]-4'-(trifluoromethyl)biphenyl-3-carboxylic acid;
N-(4'-isopropoxy-2-methylbiphenyl-4-yl)methanesulfonamide;

N-(3-chloro-4'-isopropoxybiphenyl-4-yl)methane-sulfonamide; and

N-(2-amino-4'-(trifluoromethyl)biphenyl-4-yl)methane-sulfonamide.

21. The method of claim 1, wherein the disease state is a cardiovascular disease selected from one or more of atrial and ventricular arrhythmias, heart failure (including congestive heart failure, diastolic heart failure, systolic heart failure, acute heart failure), Prinzmetal's (variant) angina, stable and unstable angina, exercise induced angina, congestive heart disease, ischemia, recurrent ischemia, reperfusion injury, myocardial infarction, acute coronary syndrome, peripheral arterial disease, and intermittent claudication.

22. The method of claim 1, wherein the disease state is diabetes or diabetic peripheral neuropathy.

23. The method of claim 1, wherein the disease state results in one or more of neuropathic pain, seizures, or paralysis.

24. The method of claim 1 comprising administering to a patient in need thereof a pharmaceutically acceptable excipient and a therapeutically effective amount of a compound of the Formula (1A) or (1B) or a pharmaceutically acceptable, salt or ester thereof.

* * * * *